US006861419B2

(12) United States Patent
Drewe et al.

(10) Patent No.: US 6,861,419 B2
(45) Date of Patent: Mar. 1, 2005

(54) SUBSTITUTED 1, 4-THIAZEPINE AND ANALOGS AS ACTIVATORS OF CASPASES AND INDUCERS OF APOPTOSIS AND THE USE THEREOF

(75) Inventors: John A. Drewe, Carlsbad, CA (US); Sui Xiong Cai, San Diego, CA (US); Emma Jane Shelton, Menlo Park, CA (US); Joane Litvak, Oakland, CA (US); David Sperandio, Mountain View, CA (US); Jeffrey R. Spencer, South San Francisco, CA (US); Martin Sendzik, San Mateo, CA (US)

(73) Assignee: Cytovia, Inc., San Diego, CA (US)

( * ) Notice: Subject to any disclaimer, the term of this patent is extended or adjusted under 35 U.S.C. 154(b) by 317 days.

(21) Appl. No.: 09/836,548

(22) Filed: Apr. 18, 2001

(65) Prior Publication Data

US 2002/0010169 A1 Jan. 24, 2002

Related U.S. Application Data
(60) Provisional application No. 60/197,599, filed on Apr. 18, 2000.

(51) Int. Cl.$^7$ .......................... A61K 31/55; A61P 35/00; C07D 281/02

(52) U.S. Cl. .............................. 514/211.01; 514/211.15; 540/544

(58) Field of Search ..................... 540/544; 514/211.01, 514/211.15

(56) References Cited

FOREIGN PATENT DOCUMENTS

| WO | WO 96/20721 A1 | 7/1996 |
| WO | WO 98/56785 A1 | 12/1998 |
| WO | WO 99/18856 A1 | 4/1999 |
| WO | WO 99/56736 A2 | 11/1999 |
| WO | WO 00/04901 | 2/2000 |
| WO | WO 00/07017 A2 | 2/2000 |

OTHER PUBLICATIONS

Vaux et al., Cell Death in Development, Cell, Jan. 22, 1999, vol. 96, pp. 245–254, especially 248.*
Balasubramanian et al., Recent Developments in Cancer Cytotoxics, Annual Reports in Medicinal Chemistry, vol. 33, pp. 151–159, 1996.*
Draetta et al., Cell Cycle Control and Cancer, Annual Reports in Medicinal Chemistry, vol. 31, pp. 241–248, 1996.*
Salmon et al., Principles of Cancer Therapy, Cecil Textbook of Medicine, 20th ED., vol. 1, pp. 1036–1049, 1996.*
CAPLUS printout for WO 00/07017, Feb. 10, 2000.*
Attia, A.E–H., and Michael, M., "Azachalcones. IV⁺. Reactions of Azachalcones with O–Phenylenediamine," *Gazz. Chim. Ital.* 112:387–390, Wiley–VCH Verlag GmbH (1982).

Barot, V.M., et al., "New 7–(2'–Hydroxy–4'Methoxy–5'–Bromophenyl)–5–Substituted Phenyl-2,3,6,7 Tetrahydro–1, 4–Oxazapine," *J. Inst. Chemists (India)* 71:70–71, Calcutta: The Institution (1999).
Batteux, F., et al., "Gene Therapy of Experimental Autoimmune Thyroiditis by In Vivo Administration of Plasmid DNA Coding for Fas Ligand," *J. Immunol.* 162:603–608, American Association of Immunologists (Jan. 1999).
Bharucha, P.B. and Naik, H.B., "Synthesis and Antibacterial Activity of Some Chalcones and 1,4–Oxazipine Derivatives," *Asian J. Chem.* 12:318–320, M.R.S. Pushpa Agarwal (Jan.–Mar. 2000).
Boirivant, M., et al., "Lamina Propria T Cells in Crohn's Disease and Other Gastrointestinal Inflammation Show Defective CD2 Pathway–Induced Apoptosis," *Gastrointerology* 116:557–565, WB Saunders Company (Mar. 1999).
Coven, T.R., et al., "PUVA–induced lymphocyte apoptosis: Mechanism of action in psoriasis," *Photodermatol. Photoimmunol. Photomed.* 15:22–27, Munksgaard (Feb. 1999).
Curtze, J. and Thomas, K., "RingschluBreaktionen an heterocyclischen Sechs– und Siebenringsystemen," *Liebigs Ann. Chem.* 328–333, Verlag Chemie (1974).
de Sarro, G., et al., "5H–[1,2,4]Oxadiazolo[5,4–d] [1,5] benzothiazepines as anticonvulsant agents in DBA/2 mice," *Eur. J. Med. Chem.* 30:925–929, Elsevier Science (1995).
Djudjić, R. and Trkovnik, M., "Syntheses of new Coumarinic Benzothiazepines, Benzodiazepines, and Benzopyranodiazepines," *Croatica Chemica Acta* 63:13–18, Nolit Publishing House (1990).
Ellis, R.E., and Horvitz, H.R., "Two *C. elegans* genes control the programmed deaths of specific cells in the pharynx," *Development* 112:591–603, Company of Biologists, Ltd. (1991).

(List continued on next page.)

Primary Examiner—Brenda Coleman
(74) Attorney, Agent, or Firm—Sterne, Kessler, Goldstein & Fox P.L.L.C.

(57) ABSTRACT

The present invention is directed to substituted 1,4-thiazepine and analogs thereof, represented by the general Formula I:

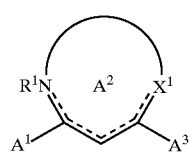

I wherein the dashed lines, $A^1$, $A^2$, $A^3$, $X^1$ and $R^1$ are defined herein. The present invention also relates to the discovery that compounds having Formula I are activators of capases and inducers of apoptosis. Therefore, the activators of caspases and inducers of apoptosis of this invention can be used to induce cell death in a variety of clinical conditions in which uncontrolled growth and spread of abnormal cells occurs.

40 Claims, No Drawings

OTHER PUBLICATIONS

Ellis R.E., et al., "Mechanisms and Functions of Cell Death," *Annu. Rev. Cell Biol.* 7:663–698, Annual Reviews, Inc. (1991).

Fodili, M., et al., "An Efficient Synthesis of New 2–Pyronyl–1,5–Benzodiazepine Derivatives," *Synthsis* 5:811–814, Thieme Stuttgart (May 1999).

Friesen, C., et al., Involvement of the CD95 (APO–1/Fas) receptor/ligand system in drug–induced apoptosis in leukemia cells, *Nat. Med.* 2:574–577, Nature America, Inc. (1996).

Glücksmann, A., "Cell deaths in normal vertebrate ontogeny," *Biol. Rev. Camb. Philos. Soc.* 26:59–86, Cambridge University Press (1951).

Glücksmann, A., "Cell death in normal development," *Arch Biol (Liège)* 76:419–437, Vaillant Germanne SA (1965).

Gupta, A.K., et al., "Syntheses & Spectral Studies of Some 2–(Substituted phenyl)–4–phenyl–1,5–benzothiazepines," *Indian J. Chem.* 22B:1057–1059, Publications and Information Directorate (CSIR) (1983).

Heenen, M., et al., "Methotrexate induces apoptotic cell death in human keratonicytes," *Arch. Dermatol. Res.* 290:240–245, Springer–Verlage (1998).

Ibrahim, S.S., et al., "Synthesis of New 3–Acryloyl–1, 2–dihydro–4–hydroxy–1–methyl–2–oxoquinoline. Derivatives and their Behavior towards Some Nucleophiles," *Chem. Papers* 51:33–42, Slovak Academic Press, Ltd. (1997).

Ibrahim, S.S., et al., "New Quinolones and Naphthyridinones Bearing Heterocyclic Rings," *Chem. Papers* 53:53–64, Slovak Academic Press, Ltd. (Jan./Feb. 1999).

Infante, A.J., et al., "The clinical spectrum in a large kindred with autoimmune lymphoproliferative syndrome caused by a Fas mutation that impairs lymphocyte apoptosis," *J. Pediatr.* 133:629–633, Mosby, Inc. (1998).

Jadhav, K.P. and Ingle, D.B., "Synthesis of 2,4–Diaryl–2, 3–dihydro–1,5–benzothiazepines and Their 1,1–Dioxides as Antibacterial Agents," *Indian J. Chem.* 22B:180–182, Publications & Information Directorate(CSIR) (1983).

Khanna, M.S., et al., "A novel approach to tetrahysrobenzothiazepines from chalcones using o–aminothiophenol," *Indian J. of Chem.* 34B:333–335, Publications and Information Directorate (CSIR) (1995).

Lévai, A. and Bognár, R., "Oxazepines and Thiazepines, II. Synthesis of 2,3–Dihydro–2,4–Diphenyl–1,5–Benzothiazepines by the Reaction of 2–Aminothiophenol with Chalcones Substituted in Ring B," *Acta Chim. (Budapest)* 88:293–300, Budapest: Akademiai Kiado (1976).

Lévai, A., "Oxazepines and Thiazepines 38* Synthesis of 2,4–Diaryl–2,3–Dihydro–1,5–Benzothiazepines by the Reaction od 2–Hydropxychalcones with 2–Aminothiophenol," *Heterocyclic Comm.* 5:359–364, Freund Publishing (1999).

Lévai, A., "Synthesis and Chemical Transformation of 1,5–Benzothiazepines," *J. Heterocyclic Chem.* 37:199–214, Hetero Corporation (Mar.–Apr. 2000).

López–Hoyos, M., et al., "Regulation of B cell apoptosis by Bcl–2 and Bcl–$X_L$ and its role in the development of autoimmune disease (Review)," *Int. J. Mol. Med.* 1:475–483, Professor DA Spandidos (1998).

Los, M., et al., Cross–Resistance of CD95—and Drug–Induced Apoptosis as a Consequence of Deficient Activation of Caspases (ICE/Ced–3 Proteases) *Blood* 90:3118–3129, American Society of Hematology (1997).

Mohamed, H.A., et al., "Synthesis of 3–Heteroaryl–4–hydroxybenzocarbostyrils," *J. Indian Chem. Soc.* 69:82–84, Calcutta: The Society (1992).

Naik, V.R. and Naik, H.B., "Synthesis and Antibacterial Activity of 2,3–Dihydro–4–(2'–Hydroxy–3'–Bromo–5'–Ethylphen–1'–yl)–2–Substitutedphenyl–1,5–Benzothiazepine Derivatives," *Asian J. Chem.* 11:661–662, M.R.S. Pushpa Agarwal (Apr.–Jun. 1999).

Ohsako, S., and Elkon, K.B., "Apoptosis in the effector phase of autoimmune diabetes, multiple sclerosis and thyroiditis," *Cell Death Differ.* 6:13–21, Stockton Press (Jan. 1999).

Ohta, S., et al., "Inhibition of P–selectin specific cell adhesion by a low molecular weight, non–carbohydrate compound, KF38789," *Inflamm. Res.* 50:544–551, Birkhäuser Verlag, Basel (Nov. 2001).

O'Reilly, L.A., and Strasser, A., "Apoptosis and autoimmune disease," *Inflamm. Res.* 48:5–21, Birkhäuser Verlag AG (Jan. 1999).

Orlov, V.D., et al., "2,4–Diaryl–2,3–Dihydrobenzo[b][1,4] Thiazepines," *Translation from Khim. Getero. Soed.* 12:1638–1642, Plenum Publishing Corp. (1983).

Orrenius, S., "Apoptosis: molecular mechanisms and implications for human disease," *J. Intern. Med.* 237:529–536, Blackwell Science, Ltd. (1995).

Ozawa, M., et al., "312–nanometer Ultraviolet B Light (Narrow–Band UVB) Induces Apoptosis of T Cells within Psoriatic Lesions," *J. Exp. Med.* 189:711–718, Rockefeller University Press (Feb. 1999).

Savill, J., "Apoptosis in resolution of inflammation," *J. Leukoc. Biol.* 61:375–380, Society for Leukocyte Biology (1997).

Sayed, A.A., et al. "The Behavior of some 3–Substituted 4–Hydroxy–1–alkyl (or phenyl) Carbostyrils towards Amines and Hydrazines," *Eygpt. J. Chem.* 19: 811–826, National Information & Documentation Centre (1976).

Schmitt, E., et al., "The Bcl–xL and Bax–α control points: modulation of apoptosis induced by cancer chemotherapy and relation to TPCK–sensitive protease and capsase activation," *Biochem. Cell Biol.* 75:301–314, NRC Research Press (1997).

Srivastava, V.K., et al., "2–(2'–Hydroxyphenyl)–4–aryl–1, 5–benzodiazepines as CNS Active Agents," *Arzneimittelforschung* 32:1512–1514, Editio Cantor Verlag GmBH ECV (1982).

Srivastava, Y.K., et al., "Synthesis and spectral studies of some 2,3,6,7 tetrahydro–5,7–diphenyl–1H–1,4–diazepines," *Nat. Acad. Sci. Letters* 11:387–389, National Academy of Sciences (1988).

Sucheta, K., et al., "Synthesis of some new 1,5–benzothiazepine derivatives," *Indian J. Chem.* 34B:893–894, Publications & Information Directorate (1995).

Thornberry, N.A., "Caspases: key mediators of apoptosis," *Chem. Biol.* 5:R97–R103, Current Biology, Ltd. (1998).

Thornberry, N.A., "The caspase family of cysteine proteases," *Br. Med. Bull.* 53:478–490, Royal Society of Medicine Press, Ltd. (1996).

Vaishnaw, A.K., et al., "The molecular basis for apoptotic defects in patients with CD95 (Fas/Apo–1) mutations," *J. Clin. Invest.* 103:355–363, Rockefeller University Press (Feb. 1999).

Vaux, D.L., et al., "An Evolutionary Perspective on Apoptosis," *Cell* 76:777–779, Cell Press (1994).

Wakisaka, S., et al., "Modulation by proinflammatory cytokines of Fas/Fas ligand–mediated apoptotic cell death of synovial cells in patients with rheumatoid arthritis (RA)," *Clin. Exp. Immunol.* 114:119–128, Blackwell Science, Ltd. (1998).

Wyllie, A.H., et al., "Cell Death: The Significance of Apoptosis," *Int. Rev. Cytol.* 68:251–306, Academic Press, Inc. (1980).

Wyllie, A.H., "Cell death: a new classification separating apoptosis from necrosis," in *Cell death in biology and pathology*, Bowen, I.D. and Lockshin, R.A., eds., Chapman and Hall, London, pp. 9–34 (1981).

Zhelyazkov, L. and Bizhev, A., "Diazepine derivatives with probable pharmacological activity," *God. Vissh. Khim.–Tekhnol. Inst.* 20:251–258, Tekhnolocigal Institut and Jahrbuch der Hochschule for Cmhische Technologie, Burgas (1974).

Zhou, T., et al., "Bisindolylmaleimide VIII facilitates Fas–mediated apoptosis and inhibits T Cell–mediated autoimmune diseases," *Nat. Med.* 5:42–48, Nature America, Inc. (Jan. 1999).

International Search Report for International Application No. PCT/US01/12581, mailed Nov. 5, 2001.

Dialog File 351, Accession No. 12274767, Derwent WPI English language abstract for WO 98/56785 (Document AM1), 1998.

STNEasy Database, Accession No. 1975:579016, English language abstract of Zhelyazkov, L. and Bizhev, A. (1975) (Document AR17).

STNEasy Database, Accession No. 1974:403902, English language abstract of Curtze, J. and Thomas, K. (1974) (Document AR3).

U.S. Provisional Appl. No. 60/197,599, Cai et al., filed Apr. 18, 2000.

Haggarty, S.J., et al., "Dissecting cellular processes using small molecules: identification of colchicine–like, taxol–like and other small molecules that perturb mitosis," *Chem. & Biol.* 7:275–286, Elsevier Science Ltd (Mar. 2000).

Ruddon, R.W., "Biochemistry of Cancer," in *Cancer Medicine*, available at www.ncbi.nlm.nih.gov/books, Bast, R.C., et al., eds., B.C. Decker, Inc., Hamilton, Ontario, section 1.7, (May 2000).

* cited by examiner

US 6,861,419 B2

SUBSTITUTED 1,4-THIAZEPINE AND ANALOGS AS ACTIVATORS OF CASPASES AND INDUCERS OF APOPTOSIS AND THE USE THEREOF

CROSS-REFERENCE TO RELATED APPLICATION

This application claims the benefit under 35 U.S.C. § 119(e)1 of prior filed U.S. Provisional Application No. 60/197,599, filed on Apr. 18, 2000, the contents of which are entirely incorporated by reference herein.

BACKGROUND OF THE INVENTION

1. Field of the Invention

This invention is in the field of medicinal chemistry. In particular, the invention relates to substituted 1,4-thiazepine and analogs, and the discovery that these compounds are activators of caspases and inducers of apoptosis. The invention also relates to the use of these compounds as therapeutically effective anti-cancer agents.

2. Related Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis, et al., *Dev.* 112:591–603 (1991); Vaux, et al. *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529–536 (1995).

Apoptosis is achieved through an endogenous mechanism of cellular suicide (Wyllie, A. H., in *Cell Death in Biology and Pathology*, Bowen and Lockshin, eds., Chapman and Hall (1991), pp. 9–34). A cell activates its internally encoded suicide program as a result of either internal or external signals. The suicide program is executed through the activation of a carefully regulated genetic program (Wyllie, et al., *Int Rev. Cyt.* 68:251 (1980); Ellis, et al., *Ann Rev. Cell Bio.* 7:663 (1991). Apoptotic cells and bodies are usually recognized and cleared by neighboring cells or macrophages before lysis. Because of this clearance mechanism, inflammation is not induced despite the clearance of great numbers of cells (Orrenius, S., *J Internal Medicine* 237:529–536 (1995)).

A group of proteases are a key element in apoptosis (see, e.g., Thorneberry, *Chemistry and Biology* 5:R97–R103 (1998); Thornberry, *British Med. Bull.* 53:478–490 (1996)). Genetic studies in the nematode *Caenorhabditis elegans* revealed that apoptotic cell death involves at least 14 genes, two of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. Further extensive research revealed that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activate the caspase cascade. This makes the cancer cells lose their capacity to undergo cellular suicide and the cells become immortal, i.e., they become cancerous. Control points are known to exist in the apoptosis process that represent points for intervention leading to activation. These control points include the CED-9-BCL-like and CED-3-ICE-like gene family products, which are intrinsic proteins regulating the fate of a cell to survive or die, respectively, and executing part of the cell death process itself (see, Schmitt, et al., *Biochem. Cell. Biol.* 75:301–314 (1997)). BCL-like proteins include BCL-XL and BAX-alpha, which appear to function upstream of caspase activation. BCL-xL appears to prevent activation of the apoptotic protease cascade, whereas BAX-alpha accelerates activation of the apoptotic protease cascade.

Chemotherapeutic (anti-cancer) drugs can trigger cancer cells to undergo suicide by activation of the dormant caspase cascade. This may be a crucial aspect of the mode of action of most, if not all, known anticancer drugs (Los, et al., *Blood* 90:3118–3129 (1997); Friesen, et al., *Nat. Med.* 2:574 (1996)). The mechanism of action of current antineoplastic drugs frequently involves an attack at specific phases of the cell cycle. The cell cycle refers to the stages through which cells normally progress during their lifetimes. Normally, cells exist in a resting phase termed $G_0$. During multiplication, cells progress to a stage in which DNA synthesis occurs, termed S. Later, cell division, or mitosis, occurs in a phase called M. Antineoplastic drugs such as cytosine arabinoside, hydroxyurea, 6-mercaptopurine, and methotrexate are S phase specific, whereas antineoplastic drugs such as vincristine, vinblastine, and paclitaxel are M phase specific. Many slow growing tumors, for example colon cancers, exist primarily in the $G_0$ phase, whereas rapidly proliferating normal tissues, for example bone marrow, exist primarily in the S or M phase. Thus, the possibility exists for the activation of the caspase cascade, although the exact mechanisms for doing so presently are not clear. Furthermore, insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could be effected by enhancement of the apoptotic process through the administration of appropriate caspase cascade activators and inducers of apoptosis.

Sucheta et al., (*Indian J. Chem. Sect. B*: 34B:893–4 (1995)) reported the synthesis of 1,4-benzothiazepine derivatives by reaction of 2-aminothiophenol with 3-cinnamoyl-2-pyrones (R=2-OMe, 2-, 4-OH, 2-, 4-NO$_2$, 2,6-Cl$_2$, 2-Cl):

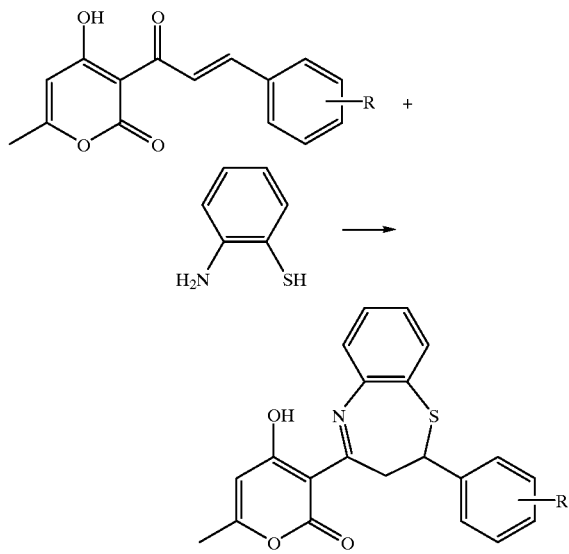

SUMMARY OF THE INVENTION

The present invention is related to novel compounds of Formula I and the use of such compounds for treating, preventing or ameliorating neoplasia and cancer.

A second aspect of the present invention is related to the discovery that substituted 1,4-thiazepine and analogs are activators of the caspase cascade and inducers of apoptosis. Thus, an aspect of the present invention is directed to substituted 1,4-thiazepine and analogs as inducers of apoptosis.

A third aspect of the present invention is to provide a method for treating, preventing or ameliorating neoplasia and cancer by administering a compound of Formula I to a mammal in need of such treatment.

A fourth aspect of the present invention is to provide a pharmaceutical composition useful for treating disorders responsive to the induction of apoptosis, containing an effective amount of a compound of Formula I in admixture with one or more pharmaceutically acceptable carriers or diluents.

A fifth aspect of the present invention is directed to methods for the preparation of compounds of Formula I.

DETAILED DESCRIPTION OF THE PREFERRED EMBODIMENTS

The present invention arises out of the discovery that substituted 1,4-thiazepine and analogs, as represented in Formula I, are potent and highly efficacious activators of the caspase cascade and inducers of apoptosis. Therefore compounds of Formula I are useful for treating disorders responsive to induction of apoptosis.

Specifically, compounds useful in this aspect of the present invention are represented by Formula I:

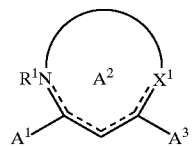

in which:
the dashed lines indicate optional unsaturation without violating valency rules;
R$^1$ is hydrogen, (C$_{1-6}$)alkyl or —C(O)R$^6$, wherein R$^6$ is as defined below, or R$^1$ is absent when a double bond exists between the nitrogen atom to which R$^1$ is attached and an adjacent ring atom or R$^1$ is as defined below;
X$^1$ is —NR$^2$—, —S—, —S(O)—, —S(O)$_2$— or —O—, wherein R$^2$ is hydrogen or (C$_{1-6}$)alkyl or is absent when a double bond exists between the nitrogen atom to which R$^2$ is attached and an adjacent ring atom;
A$^1$ is a monocyclic or fused polycyclic ring system selected from aryl containing a total of 6 to 14 ring atoms, heteroaryl containing a total of 5 to 14 ring atoms and unsaturated, partially unsaturated or saturated carbocycloalkyl or heterocycloalkyl each containing a total of 3 to 14 ring atoms, or A$^1$ together with R$^1$ and the atoms to which A$^1$ and R$^1$ are attached forms a fused polycyclic ring system selected from heteroaryl and unsaturated, partially unsaturated or saturated heterocycloalkyl in any case containing a total of 10 to 15 ring atoms, wherein A$^1$ may be substituted with a group selected from —X$^2$R$^3$, —X$^2$OR$^3$, —X$^2$C(O)R$^3$, —X$^2$OC(O)R$^3$, —X$^2$C(O)OR$^3$, —X$^2$SR$^3$, —X$^2$S(O)R$^3$, —X$^2$S(O)$_2$R$^3$, —X$^{2NR3}$R$^4$, —X$^2$NR$^4$C(O)R$^3$, —X$^2$NR$^4$C(O)OR$^3$, —X$^2$C(O)NR$^3$R$^4$, —X$^2$NR$^4$C(O)NR$^3$R$^4$, —X$^2$NR$^4$C(NR$^4$)NR$^3$R$^4$, —X$^2$NR$^4$S(O)$_2$R$^3$ and —X$^2$S(O)$_2$NR$^3$R$^4$, wherein X$^2$ is a bond or (C$_{1-6}$) alkylene, R$^3$ is —X$^2$R$^5$ wherein X$^2$ is as defined above and R$^5$ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and R$^4$ at each occurrence independently is hydrogen, (C$_{1-6}$)alkyl or halo-substituted (C$_{1-6}$)alkyl, wherein each ring within A$^1$ and R$^5$ contains from 3 to 8 ring atoms and may be substituted with 1 to 3 groups independently selected from (C$_{1-6}$) alkyl, cyano, halo, nitro, halo-substituted (C$_{1-6}$)alkyl, —X$^2$OR$^4$, —X$^2$C(O)R$^6$, —X$^2$OC(O)R$^6$, —X$^2$C(O) OR$^4$, —X$^2$SR$^4$, —X$^2$S(O)R$^6$, —X$^2$S(O)$_2$R$^6$, —X$^2$NR$^4$R$^4$, —X$^2$NR$^4$C(O)R$^6$, —X$^2$NR$^4$C(O)OR$^4$, —X$^2$C(O)NR$^4$R$^4$, —X$^2$NR$^4$C(O)NR$^4$R$^4$, —X$^2$NR$^4$C (NR$^4$)NR$^4$R$^4$, —X$^2$NR$^4$S(O)$_2$R$^6$ and —X$^2$S(O)$_2$ NR$^4$R$^4$, wherein X$^2$ and R$^4$ are as defined above and R$^6$ is (C$_{1-6}$)alkyl or halo-substituted (C$_{1-6}$)alkyl, and wherein any said carbocycloalkyl and heterocycloalkyl rings within A$^1$ and R$^5$ may be substituted further with 1 to 2 groups independently selected from (C$_{1-6}$) alkylidene, oxo, imino and thioxo, with the proviso that only one of A$^1$ and R$^5$ is a fused polycyclic ring system;
A$^2$ is a monocyclic or fused bicyclic ring selected from heteroarylene or unsaturated, partially unsaturated or saturated heterocycloalkylene containing a total of 5 to 11 ring atoms, wherein A$^2$ may be substituted with a group selected from —X$^2$R$^8$, —X$^2$OR$^8$, —X$^2$C(O)R$^8$, —X²OC(O)R⁸, —X²C(O)OR⁸, —X²SR⁸, —X²S(O)R⁸, —X²S(O)₂R⁸, —X²NR⁴R⁸, —X²NR⁴C(O)R⁸, —X²NR⁴C(O)OR⁸, —X²C(O)NR⁴R⁸, —X²NR⁴C(O)NR⁴R⁸, —X²NR⁴C(NR⁴)NR⁴R⁸, —X²NR⁴S(O)₂R⁸ and —X²S(O)₂NR⁴R⁸, wherein X² is a bond or (C₁₋₆) alkylene, R⁸ is —X²R⁹ wherein X² is as defined above and R⁹ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and R⁴ at each occurrence independently is hydrogen, (C₁₋₆)alkyl or halo-substituted (C₁₋₆)alkyl, wherein each ring within A² and R⁸ contains from 3 to 8 ring atoms and may be substituted with 1 to 3 groups independently selected from (C₁₋₆) alkyl, cyano, halo, nitro, halo-substituted (C₁₋₆)alkyl, —X²OR⁴, —X²C(O)R⁶, —X²OC(O)R⁶, —X²C(O)OR⁴, —X²SR⁴, —X²S(O)R⁶, —X²S(O)₂R⁶, —X²NR⁴R⁴, —X²NR⁴C(O)R⁶, —X²NR⁴C(O)OR⁴, —X²C(O)NR⁴R⁴, —X²NR⁴C(O)NR⁴R⁴, —X²NR⁴C(NR⁴)NR⁴R⁴, —X²C(O)NR⁴X²C(O)OR⁴, —X²NR⁴S(O)₂R⁶ and —X²S(O)₂NR⁴R⁴, wherein X² and R⁴ are as defined above and R⁶ is (C₁₋₆)alkyl or halo-substituted (C₁₋₆)alkyl, and wherein any said heterocycloalkylene, carbocycloalkyl and heterocycloalkyl rings within A² and R⁸ may be substituted further with 1 to 2 groups independently selected from (C₁₋₆)alkylidene, oxo, imino and thioxo, with the proviso that only one of A² and R⁸ is a fused polycyclic ring system; and A³ is a monocyclic or fused polycyclic ring system selected from aryl containing a total of 6 to 14 ring atoms, heteroaryl containing a total of 5 to 14 ring atoms and unsaturated, partially unsaturated or saturated carbocycloalkyl or heterocycloalkyl each containing a total of 3 to 14 ring atoms, wherein A³ may be substituted with a group selected from —X²R⁹, —X²OR⁹, —X²C(O)R⁹, —X²OC(O)R⁹, —X²C(O)OR⁹, —X²SR⁹, —X²S(O)R⁹, —X²S(O)₂R⁹, —X²NR⁴R⁹, —X²NR⁴C(O)R⁹, —X²NR⁴C(O)OR⁹, —X²C(O)NR⁴R⁹, —X²NR⁴C(O)NR⁴R⁹, —X²NR⁴C(NR⁴)NR⁴R⁹, —X²NR⁴S(O)₂R⁹ and —X²S(O)₂NR⁴R⁹, wherein X² is a bond or (C₁₋₆)alkylene, R⁹ is —X²R¹⁰ wherein X² is as defined above and R¹⁰ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and R⁴ at each occurrence independently is hydrogen, (C₁₋₆)alkyl or halo-substituted (C₁₋₆)alkyl, wherein each ring within A³ and R¹⁰ contains from 3 to 8 ring atoms and may be substituted with 1 to 3 groups independently selected from (C₁₋₆)alkyl, cyano, halo, nitro, halo-substituted (C₁₋₆)alkyl, —X²OR⁴, —X²C(O)R⁶, —X²OC(O)R⁶, —X²C(O)OR⁴, —X²SR⁴, —X²S(O)R⁶, —X²S(O)₂R⁶, —X²NR⁴R⁴, —X²NR⁴C(O)R⁶, —X²NR⁴C(O)OR⁴, —X²C(O)NR⁴R⁴, —X²NR⁴C(O)NR⁴R⁴, —X²NR⁴C(NR⁴)NR⁴R⁴, —X²NR⁴S(O)₂R⁶ and —X²S(O)₂NR⁴R⁴, wherein X² and R⁴ are as defined above and R⁶ is (C₁₋₆)alkyl or halo-substituted (C₁₋₆)alkyl, and wherein any said carbocycloalkyl and heterocycloalkyl rings within A³ and R¹⁰ may be substituted further with 1 to 2 groups independently selected from (C₁₋₆)alkylidene, oxo, imino and thioxo, with the proviso that only one of A³ and R¹⁰ is a fused polycyclic ring system; and the N-oxide derivatives, prodrug derivatives, protected derivatives, individual stereoisomers and mixtures of stereoisomers; and the pharmaceutically acceptable salts thereof;

with the proviso that when said compound is selected from the group consisting of Formulae II(a), II(b) and II(c):

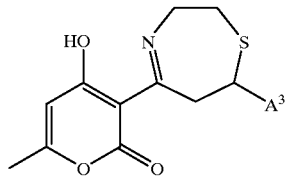

II(a)

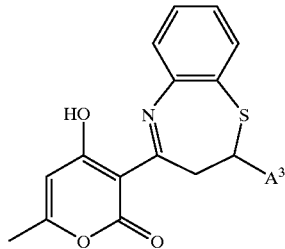

II(b)

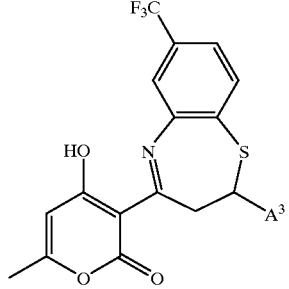

II(c)

then A³ is other than:
unsubstituted pyridyl;
unsubstituted thienyl;
unsubstituted indolyl;
unsubstituted phenyl;
benzo[1,3]dioxolyl;
2,3-dihydro-benzo[1,4]dioxinyl;
phenyl which is mono-substituted by fluoro, bromo, iodo, methyl, isopropyl, ethoxy or methylsulfanyl; and
phenyl which is substituted by at least one of chloro, hydroxy or methoxy. Alternatively, compounds useful for treating disorders responsive to induction of apoptosis are represented by Formula II:

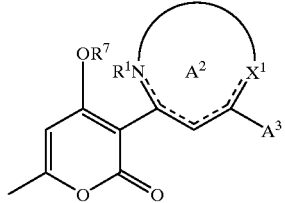

II in which:
the dashed lines indicate optional unsaturation without violating valency rules;

R¹ is hydrogen, $(C_{1-6})$alkyl or —C(O)R⁶, wherein R⁶ is asdefined below, or is absent when a double bond exists between the nitrogen atom to which R¹ is attached and an adjacent ring atom or R¹ is as defined below;

R⁷ is hydrogen;

X¹ is —NR²—, —S—, —S(O)—, —S(O)₂— or —O—, wherein R² is hydrogen or $(C_{1-6})$alkyl or is absent when a double bond exists between the nitrogen atom to which R² is attached and an adjacent ring atom;

A² is a monocyclic or fused bicyclic ring selected from heteroarylene or unsaturated, partially unsaturated or saturated heterocycloalkylene containing a total of 5 to 11 ring atoms, wherein A² may be substituted with a group selected from —R⁸, —X²OR⁸, —X²C(O)R⁸, —X²OC(O)R⁸, —X²C(O)OR⁸, —X²SR⁸, —X²S(O)R⁸, —X²S(O)₂R⁸, —X²NR⁴R⁸, —X²NR⁴C(O)R⁸, —X²NR⁴C(O)OR⁸, —X²C(O)NR⁴R⁸, —X²NR⁴C(O)NR⁴R⁸, —X²NR⁴C(NR⁴)NR⁴R⁸, —X²NR⁴S(O)₂R⁸ and —X²S(O)²NR⁴R⁸, wherein X² is a bond or $(C_{1-6})$alkylene, R⁸ is —X²R⁹ wherein X² is as defined above and R⁹ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and R⁴ at each occurrence independently is hydrogen, $(C_{1-6})$alkyl or halo-substituted $(C_{1-6})$alkyl, wherein each ring within A² and R⁸ contains from 3 to 8 ring atoms and may be substituted with 1 to 3 groups independently selected from $(C_{1-6})$alkyl, cyano, halo, nitro, halo-substituted $(C_{1-6})$alkyl, —X²OR⁴, —X²C(O)R⁶, —X²OC(O)R⁶, —X²C(O)OR⁴, —X²SR⁴, —X²S(O)R⁶, —X²S(O)₂R⁶, —X²NR⁴R⁴, —X²NR⁴C(O)R⁶, —X²C(O)NR⁴R⁴, —X²NR⁴C(O)NR⁴R⁴, —X²NR⁴C(NR)⁴NR⁴R⁴, —X²C(O)NR⁴X²C(O)OR⁴, —X²NR⁴S(O)₂R⁶ and —X²S(O)₂NR⁴R⁴, wherein X² and R⁴ are as defined above and R⁶ is $(C_{1-6})$alkyl or halo-substituted $(C_{1-6})$alkyl, and wherein any said heteroalkylene, carbocycloalkyl and heterocycloalkyl rings within A² and R⁸ may be substituted further with 1 to 2 groups independently selected from $(C_{1-6})$alkylidene, oxo, imino and thioxo with the proviso that only one of A² and R⁸ is a fused polycyclic ring system; and A³ is a monocyclic or fused polycyclic ring system selected from aryl containing a total of 6 to 14 ring atoms, heteroaryl containing a total of 5 to 14 ring atoms and unsaturated, partially unsaturated or saturated carbocycloalkyl or heterocycloalkyl each containing a total of 3 to 14 ring atoms, wherein A³ may be substituted with a group selected from —R⁹, —X²OR⁹, —X²C(O)R⁹, —X²OC(O)R⁹, —X²C(O)OR⁹, —X²SR⁹, —X²S(O)R⁹, —X²S(O)₂R⁹, —X²NR⁴R⁹, —X²NR⁴C(O)R⁹, —X²NR⁴C(O)OR⁹, —X²C(O)NR⁴R⁹, —X²NR⁴C(O)NR⁴R⁹, —X²NR⁴C(NR⁴)NR⁴R⁹, —X²NR⁴S(O)₂R⁹ and —X²S(O)₂NR⁴R⁹, wherein X² is a bond or $(C_{1-6})$alkylene, R⁹ is —X²R¹⁰ wherein X² is as defined above and R¹⁰ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and R⁴ at each occurrence independently is hydrogen, $(C_{1-6})$alkyl or halo-substituted $(C_{1-6})$alkyl, wherein each ring within A³ and R¹⁰ contains from 3 to 8 ring atoms and may be substituted with 1 to 3 groups independently selected from $(C_{1-6})$alkyl, cyano, halo, nitro, halo-substituted $(C_{1-6})$alkyl, —X²OR⁴, —X²C(O)R⁶, —X²OC(O)R⁶, —X²C(O)OR⁴, —X²SR⁴, —X²S(O)R⁶, —X²S(O)₂R⁶, —X²NR⁴R⁴, —X²NR⁴C(O)R⁶, —X²NR⁴C(O)OR⁴, —X²C(O)NR⁴R⁴, —X²NR⁴C(O)NR⁴R⁴, —X²NR⁴C(NR⁴)NR⁴R⁴, —X²NR⁴S(O)₂R⁶ and —X²S(O)₂NR⁴R⁴, wherein X² and R⁴ are as defined above and R⁶ is $(C_{1-6})$alkyl or halo-substituted $(C_{1-6})$alkyl, and wherein any said carbocycloalkyl and heterocycloalkyl rings within A³ and R¹⁰ may be substituted further with 1 to 2 groups independently selected from $(C_{1-6})$alkylidene, oxo, imino and thioxo with the proviso that only one of A³ and R¹⁰ is a fused polycyclic ring system; and the N-oxide derivatives, prodrug derivatives, protected derivatives, individual stereoisomers and mixtures of stereoisomers; and the pharmaceutically acceptable salts thereof;

provided, however, Formula II does not represent a compound wherein A² is 2,3,6,7-tetrahydro-[1,4]thiazepinylene, 2,3-dihydro-benzo[b][1,4]thiazepinylene or 7-trifluoromethyl-2,3-dihydro-benzo[b][1,4]thiazepinylene when A³ is benzo[1,3]dioxolyl, indolyl, phenyl, pyridyl or thienyl, wherein said phenyl may be substituted with 1 to 3 groups independently selected from halo, nitro, hydroxy, $(C_{1-4})$alkyl, $(C_{1-4})$alkylsulfanyl and $(C_{1-4})$alkyloxy; or any N-oxide derivative, protected derivative, individual stereoisomer or mixture of stereoisomers, or pharmaceutically acceptable salt thereof.

Preferred are compounds of Formula I in which A³ is other than unsubstituted pyridyl; unsubstituted thienyl; unsubstituted indolyl; unsubstituted phenyl; benzo[1,3]dioxol-5-yl; 2,3-dihydro-benzo[1,4]dioxinyl; orphenyl which is substituted by at least one of halogen, nitro, hydroxy, $(C_{1-3})$alkyl, methoxy, ethoxy and methylsulfanyl; and more preferred wherein A¹ is other than 4-hydroxy-6-methyl-2-oxo-2H-pyran-3-yl.

Preferred are compounds of Formula I(A):

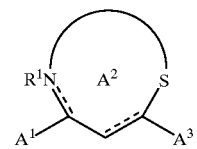

I(A)

wherein R¹, A¹, A² and A³ are as in the Detailed Description of the Invention for Formula I; and more preferred are compounds of Formula I(B):

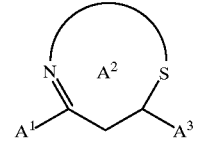

I(B)

wherein A¹, A² and A³ are as in the Detailed Description of the Invention for Formula I; and most preferred are compounds of Formula I in which A² is that is 2,3,6,7-tetrahydro-[1,4]thiazepin-5,7-ylene, that is a compound of Formula I(C):

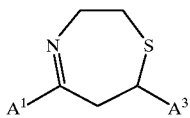

wherein A¹ and A³ are as in the Detailed Description of the Invention for Formula I and said 2,3,6,7-tetrahydro-[1,4] thiazepin-5,7-ylene maybe substituted with 1 to 3 groups independently selected from $(C_{1-6})$alkyl, cyano, halo, nitro, halo-substituted $(C_{1-6})$alkyl, $-X^2OR^4$, $-X^2C(O)R^6$, $-X^2OC(O)R^6$, $-X^2C(O)OR^4$, $-X^2SR^4$, $-X^2S(O)R^6$, $-X^2S(O)_2R^6$, $-X^2NR^4R^4$, $-X^2NR^4C(O)R^6$, $-X^2NR^4C(O)OR^4$, $-X^2C(O)NR^4R^4$, $-X^2NR^4C(O)NR^4R^4$, $-X^2NR^4C(NR^4)NR^4R^4$, $-X^2C(O)NR^4X^2C(O)OR^4$, $-X^2NR^4S(O)_2R^6$ and $-X^2S(O)_2NR^4R^4$, wherein $X^2$ is a bond or $(C_{1-6})$alkylene, $R^4$ at each occurrence independently is hydrogen, $(C_{1-6})$alkyl or halo-substituted $(C_{1-6})$alkyl, and $R^6$ is $(C_{1-6})$alkyl or halo-substituted $(C_{1-6})$alkyl.

Preferred are compounds of Formula I(C) in which A¹ is 4-hydroxy-6-methyl-2-oxo-2H-pyran-3-yl or 4-methoxy-6-methyl-2-oxo-2H-pyran-3-yl; and more preferred wherein said compound is selected from the group consisting of:

4-hydroxy-6-methyl-3-[7-(3-phenyl-1H-pyrazol-4-yl)-2,3,6,7-tetrahydro-[1,4]thiazepin-5-yl]-pyran-2-one;
3-[7-(5-ethyl-thien-2-yl)-2,3,6,7-tetrahydro-[1,4]thiazepin-5-yl]-4-hydroxy-6-methyl-pyran-2-one;
3-[7-(1-benzyl-1H-indol-3-yl)-2,3,6,7-tetrahydro-[1,4]thiazepin-5-yl]-4-hydroxy-6-methyl-pyran-2-one;
4-hydroxy-6-methyl-3[7-(2-trifluoromethylsulfanyl-phenyl)-2,3,6,7-tetrahydro-[1,4]thiazepin-5-yl]-pyran-2-one;
4-hydroxy-6-methyl-3[7-(3-trifluoromethylsulfanyl-phenyl)-2,3,6,7-tetrahydro-[1,4]thiazepin-5-yl]-pyran-2-one;
4-hydroxy-6-methyl-3[7-(4-trifluoromethylsulfanyl-phenyl)-2,3,6,7-tetrahydro-[1,4]thiazepin-5-yl]-pyran-2-one;
4-hydroxy-6-methyl-3-[7-[3-(3-trifluoromethyl-phenoxy)-phenyl]-2,3,6,7-tetrahydro-[1,4]thiazepin-5-yl]-pyran-2-one;
3-[7-[3-(3,4-dichloro-phenoxy)-phenyl]-2,3,6,7-tetrahydro-[1,4]thiazepin-5-yl]-4-hydroxy-6-methyl-pyran-2-one;
3-[7-[3-(3,5-dichloro-phenoxy)-phenyl]-2,3,6,7-tetrahydro-[1,4]thiazepin-5-yl]-4-hydroxy-6-methyl-pyran-2-one;
4-hydroxy-6-methyl-3-{7-[5-(3-trifluoromethyl-phenyl)-furan-2-yl]-2,3,6,7-tetrahydro-[1,4]thiazepin-5-yl}-pyran-2-one;
3-{7-[5-(2-chloro-phenyl)-furan-2-yl]-2,3,6,7-tetrahydro-[1,4]thiazepin-5-yl}-4-hydroxy-6-methyl-pyran-2-one;
3-{7-[5-(3-chloro-phenyl)-furan-2-yl]-2,3,6,7-tetrahydro-[1,4]thiazepin-5-yl}-4-hydroxy-6-methyl-pyran-2-one;
3-{7-[5-(4-chloro-phenyl)-furan-2-yl]-2,3,6,7-tetrahydro-[1,4]thiazepin-5-yl}-4-hydroxy-6-methyl-pyran-2-one;
4-hydroxy-6-methyl-3-{7-[5-(chloro-trifluoromethyl-phenyl)-furan-2-yl]-2,3,6,7-tetrahydro-[1,4]thiazepin-5-yl}-pyran-2-one;
3-[7-(4-bromo-thien-2-yl)-2,3,6,7-tetrahydro-[1,4]thiazepin-5-yl]-4-hydroxy-6-methyl-pyran-2-one;
3-[7-(5-bromo-thien-2-yl)-2,3,6,7-tetrahydro-[1,4]thiazepin-5-yl]-4-hydroxy-6-methyl-pyran-2-one;
3-[7-(1-benzenesulfonyl-1H-pyrrol-2-yl)-2,3,6,7-tetrahydro-[1,4]thiazepin-5-yl]-4-hydroxy-6-methyl-pyran-2-one;
4-hydroxy-6-methyl-3-[7-(3-methyl-thien-2-yl)-2,3,6,7-tetrahydro-[1,4]thiazepin-5-yl]-pyran-2-one;
4-hydroxy-6-methyl-3-[7-(5-methyl-thien-2-yl)-2,3,6,7-tetrahydro-[1,4]thiazepin-5-yl]-pyran-2-one;
4-hydroxy-6-methyl-3-[7-(1-methyl-1H-indol-3-yl)-2,3,6,7-tetrahydro-[1,4]thiazepin-5-yl]-pyran-2-one;
3-[7-(chloro-methyl-trifluoromethyl-1H-pyrazol-4-yl)-2,3,6,7-tetrahydro-[1,4]thiazepin-5-yl]-4-hydroxy-6-methyl-pyran-2-one;
3-{7-[1-(2,4-difluoro-benzenesulfonyl)-1H-pyrrrol-2-yl]-2,3,6,7-tetrahydro-[1,4]thiazepin-5-yl}-4-hydroxy-6-methyl-pyran-2-one;
3-(7-[2,2']bithienyl-5-yl-2,3,6,7-tetrahydro-[1,4]thiazepin-5-yl)-4-hydroxy-6-methyl-pyran-2-one;
3-{7-[1-(3,5-dichloro-phenyl)-1H-pyrrrol-2-yl]-2,3,6,7-tetrahydro-[1,4]thiazepin-5-yl}-4-hydroxy-6-methyl-pyran-2-one;
3-{7-[1-(4-chloro-phenyl)-1H-pyrrrol-2-yl]-2,3,6,7-tetrahydro-[1,4]thiazepin-5-yl }-4-hydroxy-6-methyl-pyran-2-one;
3-[7-(5-chloro-1H-indol-3-yl)-2,3,6,7-tetrahydro-[1,4]thiazepin-5-yl]-4-hydroxy-6-methyl-pyran-2-one;
4-hydroxy-6-methyl-3-[7-(6-p-tolylsulfanyl-imidazo[2,1-b]thiazol-5-yl)-2,3,6,7-tetrahydro-[1,4]thiazepin-5-yl]-pyran-2-one;
3-[7-(4,5-dibromo-thien-2-yl)-2,3,6,7-tetrahydro-[1,4]thiazepin-5-yl]-4-hydroxy-6-methyl-pyran-2-one;
4-hydroxy-6-methyl-3-[7-(5-methylsulfanyl-thien-2-yl)-2,3,6,7-tetrahydro-[1,4]thiazepin-5-yl]-pyran-2-one;
3-[7-(5-chloro-1-methyl-3-phenyl-1H-pyrazol-4-yl)-2,3,6,7-tetrahydro-[1,4]thiazepin-5-yl]-4-hydroxy-6-methyl-pyran-2-one;
3-[7-(4-dimethylamino-phenyl)-2,3,6,7-tetrahydro-[1,4]thiazepin-5-yl]-4-hydroxy-6-methyl-pyran-2-one;
4-hydroxy-6-methyl-3-[7-(4-trifluoromethoxy-phenyl)-2,3,6,7-tetrahydro-[1,4]thiazepin-5-yl]-pyran-2-one;
3-[7-(bis-trifluoromethyl-phenyl)-2,3,6,7-tetrahydro-[1,4]thiazepin-5-yl]-4-hydroxy-6-methyl-pyran-2-one;
4-hydroxy-3-[7-(4-methanesulfonyl-phenyl)-2,3,6,7-tetrahydro-[1,4]thiazepin-5-yl]-6-methyl-pyran-2-one; and
3-[7-(2,4-dimethoxy-phenyl)-2,3,6,7-tetrahydro-[1,4]thiazepin-5-yl]-4-methoxy-6-methyl-pyran-2-one.

Preferred are compounds of Formula I(C) in which A¹ is A¹ is 4-hydroxy-6-methyl-2-oxo-5,6-dihydro-2H-pyran-3-yl or 4-methoxy-6-methyl-2-oxo-5,6-dihydro-2H-pyran-3-yl; and more preferred wherein said compound is selected from the group consisting of:

3-[7-(2,4-dimethoxy-phenyl)-2,3,6,7-tetrahydro-[1,4]thiazepin-5-yl]-4-hydroxy-6-methyl-5,6-dihydro-pyran-2-one;
3-[7-(2,4-diethoxy-phenyl)-2,3,6,7-tetrahydro-[1,4]thiazepin-5-yl]-4-hydroxy-6-methyl-5,6-dihydro-pyran-2-one;
3-[7-(4-dimethylamino-phenyl)-2,3,6,7-tetrahydro-1,4]thiazepin-5-yl]-4-hydroxy-6-methyl-5,6-dihydro-pyran-2-one; and
3-[7-(2,3,4-trimethoxy-phenyl)-2,3,6,7-tetrahydro-1,4]thiazepin-5-yl]-4-hydroxy-6-methyl-5,6-dihydro-pyran-2-one.

Preferred are compounds of Formula I(C) in which A¹ is 2-hydroxy-6-oxo-cyclohex-1-enyl or 2-methoxy-6-oxo-cyclohex-1-enyl; and more preferred wherein said compound is selected from the group consisting of:

2-[7-(2,4-dimethoxy-phenyl)-2,3,6,7-tetrahydro-[1,4]thiazepin-5-yl]-3-hydroxy-cyclohex-2-enone;

2-[7-(2,4-diethoxy-phenyl)-2,3,6,7-tetrahydro-[1,4]thiazepin-5-yl]-3-hydroxy-cyclohex-2-enone; and 3-hydroxy-2-[7-(2,3,4-trimethoxy-phenyl)-2,3,6,7-tetrahydro-[1,4]thiazepin-5-yl]-cyclohex-2-enone.

Preferred are compounds of Formula I(C) in which A¹ is a group of Formula (c):

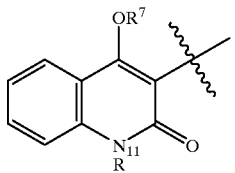

(c)

in which $R^7$ is hydrogen or methyl, $R^{11}$ is hydrogen or $(C_{1-6})$alkyl and the free valence is attached to $A^2$; and in particular the compound of Formula I(C) which is 3-[7-2,4-dimethoxy-phenyl)-2,3,6,7-tetrahydro-[1,4]thiazepin-5-yl]-4-hydroxy-1H-quinolin-2-one.

Preferred are compounds of Formula I in which $A^2$ is 2,3-dihydro-benzo[b][1,4]thiazepin-5,7-ylene, that is a compound of Formula I(D):

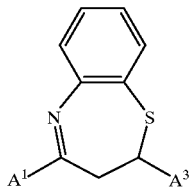

I(D)

in which $A^1$ and $A^3$ are defined as in the Detailed Description of the Invention for Formula I, and said 2,3-dihydro-benzo[b][1,4]thiazepin-5,7-ylene may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2C(O)NR^4R^4$, —$X^2NR^4C(O)NR^4R^4$, —$X^2NR^4C(NR^4)NR^4R^4$, —$X^2NR^4S(O)_2R^6$ and —$X^2S(O)_2NR^4R^4$, wherein $X^2$ is a bond or $(C_{1-6})$alkylene, $R^4$ at each occurrence independently is hydrogen, $(C_{1-6})$alkyl or halo-substituted $(C_{1-6})$alkyl, and $R^6$ is $(C_{1-6})$alkyl or halo-substituted $(C_{1-6})$alkyl.

Preferred are compounds of Formula I(D) in which $A^1$ is 4-hydroxy-6-methyl-2-oxo-2H-pyran-3-yl or 4-methoxy-6-methyl-2-oxo-2H-pyran-3-yl; and more preferred wherein said compound is 3-[2-(2,4-diethoxy-phenyl)-2,3-dihydro-benzo[b][1,4]thiazepin-4-yl]-4-hydroxy-6-methyl-pyran-2-one.

Preferred are compounds of Formula I(D) in which $A^1$ is 4-hydroxy-6-methyl-2-oxo-5,6-dihydro-2H-pyran-3-yl or 4-methoxy-6-methyl-2-oxo-5,6-dihydro-2H-pyran-3-yl; and more preferred wherein said compound is 4-hydroxy-6-methyl-3-[2-(2,3,4-trimethoxy-phenyl)-2,3-dihydro-benzo[b][1,4]thiazepin-4-yl]-5,6-dihydro-pyran-2-one.

Preferred are compounds of Formula I(D) in which $A^1$ is 2-hydroxy-6-oxo-cyclohex-1-enyl or 2-methoxy-6-oxo-cyclohex-1-enyl; and more preferred wherein said compound is selected from the group consisting of:

3-hydroxy-2-[2-(2,4-diethoxy-phenyl)-2,3-dihydro-benzo[b][1,4]thiazepin-4-yl]-cyclohex-2-enone; and 3-hydroxy-2-[2-(2,3,4-trimethoxy-phenyl)-2,3-dihydro-benzo[b][1,4]thiazepin-4-yl]-cyclohex-2-enone.

Preferred are compounds of Formula I in which $A^2$ is a group of Formula (k):

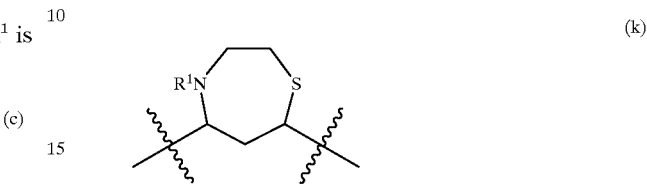

(k)

in which $R^1$ is defined as in the Detailed Description of the Invention for Formula I and said group of Formula (k) may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR^4C(O)NR^4R^4$, —$X^2NR^4C(NR^4)NR^4R^4$, —$X^2C(O)NR^4X^2C(O)OR^4$, —$X^2NR^4S(O)_2R^6$ and —$X^2S(O)_2NR^4R^4$, wherein $X^2$ is a bond or $(C_{1-6})$alkylene, $R^4$ at each occurrence independently is hydrogen, $(C_{1-6})$alkyl or halo-substituted $(C_{1-6})$alkyl, and $R^6$ is $(C_{1-6})$alkyl or halo-substituted $(C_{1-6})$alkyl; preferably wherein $R^1$ is hydrogen.

Preferred are compounds of Formula I in which in which $A^2$ is a group of Formula (k) and $A^1$ is 4-hydroxy-6-methyl-2-oxo-5,6-dihydro-2H-pyran-3-yl or 4-methoxy-6-methyl-2-oxo-5,6-dihydro-2H-pyran-3-yl; and more preferred wherein said compound is selected from the group consisting of:

3-[4-acetyl-7-(2,4-dimethoxy-phenyl)-[1,4]thiazepan-5-yl]-4-hydroxy-6-methyl-pyran-2-one; and 3-[7-(2,4-dimethoxy-phenyl)-4-(2,2,2-trifluoro-ethanoyl)-[1,4]thiazepan-5-yl]-4-hydroxy-6-methyl-pyran-2-one.

Preferred are compounds of Formula I in which in which $A^2$ is a group of Formula (k) and $A^1$ is optionally substituted phenyl; and more preferred wherein said compound is 1-[7-(2,4-dimethoxy-phenyl)-5-(3-fluoro-4-methoxyphenyl)-[1,4]thiazepan-4-yl]-ethanone.

Preferred are compounds of Formula I in which $A^2$ is 2,3-dihydro-[1,4]thiazepin-5,7-ylene, that is the compound of Formula I(F):

I(F)

in which $A^1$ and $A^3$ are defined as in claim 1, and said 2,3-dihydro-[1,4]thiazepin-5,7-ylene may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR C(O)NR^4R^4$, —$X^2NR^4C(NR^4)NR^4R^4$, —$X^2C(O)NR^4X^2C(O)OR^4$, —$X^2NR^4S(O)_2R^6$ and —$X^2S(O)_2NR^4R^4$, wherein $X^2$ is a bond or $(C_{1-6})$alkylene, $R^4$ at each occurrence independently is hydrogen, $(C_{1-6})$alkyl or halo-substituted $(C_{1-6})$alkyl, and $R^6$ is $(C_{1-6})$alkyl or halo-substituted $(C_{1-6})$alkyl.

Preferred are compounds of Formula I(F) in which $A^1$ is 4-hydroxy-6-methyl-2-oxo-2H-pyran-3-yl or 4-methoxy-6-methyl-2-oxo-2H-pyran-3-yl; and more preferred wherein said compound is selected from the group consisting of:

3-[7-(2,4-dimethoxy-phenyl)-2,3-dihydro-[1,4]thiazepin-5-yl]-4-hydroxy-6-methyl-pyran-2-one;

3-[7-(2,4-diethoxy-phenyl)-2,3-dihydro-[1,4]thiazepin-5-yl]4-hydroxy-6-methyl-pyran-2-one; and 3-(7-[2,2']bithienyl-5-yl-2,3-dihydro-[1,4]thiazepin-5-yl)-4-hydroxy-6-methyl-pyran-2-one.

Preferred are compounds of Formula I(F) in which $A^1$ is 4-hydroxy-6-methyl-2-oxo-5,6-dihydro-2H-pyran-3-yl or 4-methoxy-6-methyl-2-oxo-5,6-dihydro-2H-pyran-3-yl; and more preferred wherein said compound is 3-[7-(2,4-diethoxy-phenyl)-2,3-dihydro-[1,4]thiazepin-5-yl]-4-hydroxy-6-methyl-5,6-dihydro-pyran-2-one.

Preferred are compounds of Formula I(F) in which $A^1$ is 2-hydroxy-6-oxo-cyclohex-1-enyl or 2-methoxy-6-oxo-cyclohex-1-enyl; and more preferred wherein said compound is 2-[7-(2,4-diethoxy-phenyl)-2,3-dihydro-[1,4]thiazepin-5-yl]-3-hydroxy-cyclohex-2-enone.

Preferred are compounds of Formula I(G):

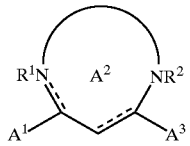

I(G)

wherein n, $R^1$, $A^1$, $A^2$ and $A^3$ are as in the Detailed Description of the Invention for Formula I; and more preferred are compounds of Formula I(G) in which $A^2$ is is a group of Formula (1):

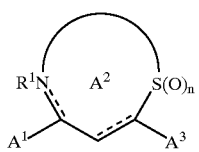

(l)

wherein n is 1 or 2; and said group of Formula (1) may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR^4C(O)NR^4R^4$, —$X^2NR^4C(NR^4)NR^4R^4$, —$X^2C(O)NR^4X^2C(O)OR^4$, —$X^2NR^4S(O)_2R^6$ and —$X^2S(O)_2NR^4R^4$, wherein $X^2$ is a bond or $(C_{1-6})$alkylene, $R^4$ at each occurrence independently is hydrogen, $(C_{1-6})$alkyl or halo-substituted $(C_{1-6})$alkyl, and $R^6$ is $(C_{1-6})$alkyl or halo-substituted $(C_{1-6})$alkyl.

Preferred are compounds of Formula I(G) in which $A^2$ is is a group of Formula (1) wherein n is 1 and $A^1$ is 4-hydroxy-6-methyl-2-oxo-2H-pyran-3-yl or 4-methoxy-6-methyl-2-oxo-2H-pyran-3-yl; in particular the compound which is 3-[7-(2,4-dimethoxy-phenyl)-1-oxo-2,3,6,7-tetrahydro-1H-1$\lambda^4$-[1,4]thiazepin-5-yl]-4-hydroxy-6-methoxy-pyran-2-one.

Preferred are compounds of Formula I(G) in which $A^2$ is is a group of Formula (1) wherein n is 2 and $A^1$ is 4-hydroxy-6-methyl-2-oxo-2H-pyran-3-yl or 4-methoxy-6-methyl-2-oxo-2H-pyran-3-yl; in particular the compound which is 3-[7-(2,4-dimethoxy-phenyl)-1,1-dioxo-2,3,6,7-tetrahydro-1H-1$\lambda^6$-[1,4]thiazepin-5-yl]-4-hydroxy-6-methyl-pyran-2-one.

Preferred are compounds of Formula I(I):

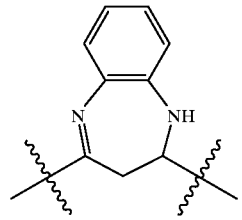

I(I)

wherein $R^1$, $R^2$, $A^1$, $A^2$ and $A^3$ are as in the Detailed Description of the Invention for Formula I; and more preferred are compounds of Formula I(I) in which $A^2$ is is a group of Formula (j):

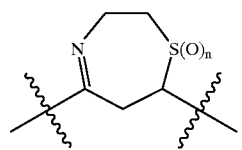

(j)

wherein said group of Formula (1) may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR^4C(O)NR^4R^4$, —$X^2NR^4C(NR^4)NR^4R^4$, —$X^2C(O)NR^4X^2C(O)OR^4$, —$X^2NR^4S(O)_2R^6$ and —$X^2S(O)_2NR^4R^4$, wherein $X^2$ is a bond or $(C_{1-6})$alkylene, $R^4$ at each occurrence independently is hydrogen, $(C_{1-6})$alkyl or halo-substituted $(C_{1-6})$alkyl, and $R^6$ is $(C_{1-6})$alkyl or halo-substituted $(C_{1-6})$alkyl.

Preferred are compounds of Formula I(I) in which $A^2$ is is a group of Formula (j) wherein $A^1$ is 4-hydroxy-6-methyl-2-oxo-2H-pyran-3-yl or 4-methoxy-6-methyl-2-oxo-2H-pyran-3-yl; in particular the compound which is 3-[4-(2,4-dimethoxy-phenyl)-4,5-dihydro-3H-benzo[b][1,4]diazepin-2-yl]-4-hydroxy-6-methylpyran-2-one.

Preferred are compounds of Formula I(K):

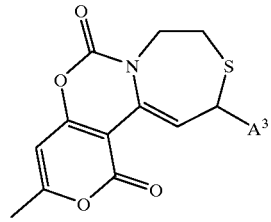

I(K)

in which $A^3$ is defined as in the Detailed Description of the Invention for Formula I.; and preferably the compound of Formula I(K) which is 10-(2,4-dimethoxy-phenyl)-3-methyl-7,8-dihydro-10H-2,5-dioxa-9-thia-6a-aza-cyclohepta[a]naphthalene-1,6-dione.

Preferred are compounds selected from the group consisting of:

4-hydroxy-3-[7-(2-methoxy-4-methylsulfanyl-phenyl)-2,3,6,7-tetrahydro-[1,4]thiazepin-5-yl]-6-methyl-pyran-2-one;

3-[7-(2-chloro-5-trifluoromethyl-phenyl)-2,3,6,7-tetrahydro-[1,4]thiazepin-5-yl]-4-hydroxy-6-methyl-pyran-2-one;

3-[7-(4-dimethylamino-2-methoxy-phenyl)-2,3,6,7-tetrahydro-[1,4]thiazepin-5-yl]-4-hydroxy-6-methyl-pyran-2-one;

7-(2,4-dimethoxy-phenyl)-5-(4-hydroxy-6-methyl-2-oxo-2H-pyran-3-yl)-2,2-dimethyl-2,3,6,7-tetrahydro-[1,4]thiazepine-3-carboxylic acid; and 2-({1-[7-(2,4-dimethoxy-phenyl)-5-(4-hydroxy-6-methyl-2-oxo-2H-pyran-3-yl)-2,2-dimethyl-2,3,6,7-tetrahydro-[1,4]thiazepin-3-yl]-methanoyl}-amino)-propionic acid tert-butyl ester.

Preferred are compounds of Formula I in which $A^1$ is a group selected from Formulae (b), (c), (d), (e) and (f):

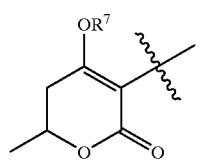

(b)

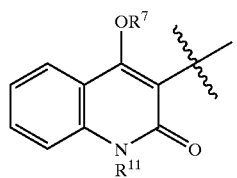

(c)

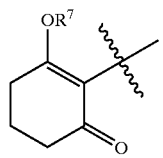

(d)

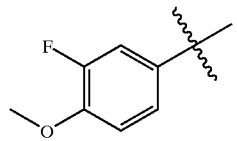

(e)

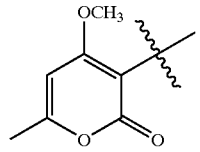

(f)

in which $R^7$ is hydrogen or methyl, $R^{11}$ is hydrogen or $(C_{1-6})$alkyl and the free valance is attached to $A^2$, or $A^2$ and $A^1$ together with $R^1$ and the atoms to which $A^1$ and $R^1$ are attached form a group of Formula (g):

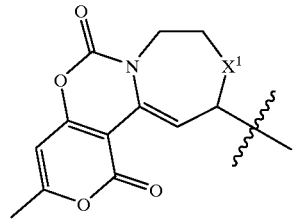

(g)

wherein $X^1$ is —S— and the free valance is attached to $A^3$; and $A^2$ is as defined above or is a monocyclic or fused bicyclic ring selected from heteroarylene or unsaturated, partially unsaturated or saturated heterocycloalkylene containing a total of 5 to 11 ring atoms, wherein $A^2$ may be substituted with a group selected from —$R^8$, —$X^2OR^8$, —$X^2C(O)R^8$, —$X^2OC(O)R^8$, —$X^2C(O)OR^8$, —$X^2SR^8$, —$X^2S(O)R^8$, —$X^2S(O)_2R^8$, —$X^2NR^4R^8$, —$X^2NR^4C(O)R^8$, —$X^2NR^4C(O)OR^8$, —$X^2C(O)NR^4R^8$, —$X^2NR^4C(O)NR^4R^8$, —$X^2NR^4C(NR^4)NR^4R^8$, —$X^2NR^4S(O)_2R^8$ and —$X^2S(O)_2NR^4R^8$, wherein $X^2$ is a bond or $(C_{1-6})$alkylene, $R^8$ is —$X^2R^9$ wherein $X^2$ is as defined above and $R^9$ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and $R^4$ at each occurrence independently is hydrogen, $(C_{1-6})$alkyl or halo-substituted $(C_{1-6})$alkyl, wherein each ring within $A^2$ and $R^8$ contains from 3 to 8 ring atoms and may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR^4C(O)NR^4R^4$, —$X^2NR^4C(NR^4)NR^4R^4$, —$X^2C(O)NR^4X^2C(O)OR^4$, —$X^2NR^4S(O)_2R^6$ and —$X^2S(O)_2NR^4R^4$, wherein $X^2$ and $R^4$ are as defined above and $R^6$ is $(C_{1-6})$alkyl or halo-substituted $(C_{1-6})$alkyl, and wherein any said heteroalkylene, carbocycloalkyl and heterocycloalkyl rings within $A^2$ and $R^8$ may be substituted further with 1 to 2 groups independently selected from $(C_{1-6})$alkylidene, oxo, imino and thioxo, with the proviso that only one of $A^2$ and $R^8$ is a fused polycyclic ring system.

Preferred are compounds of Formula I or II in which $A^2$ is a group selected from Formulae (h), (i), (j), (k), (l) and (m):

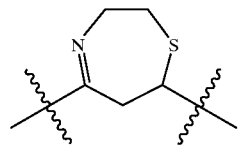

(h)

-continued

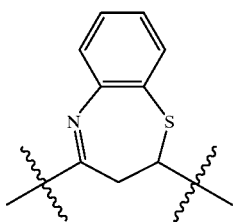
(i)

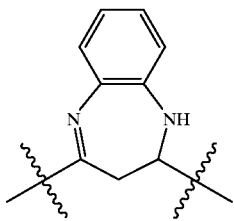
(j)

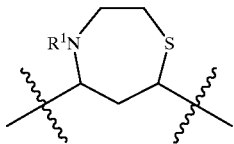
(k)

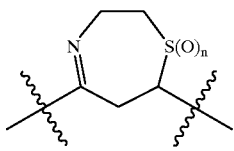
(l)

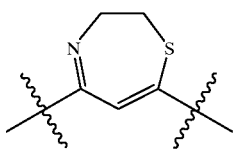
(m)

in which n is 1 or 2 and $R^1$ is acetyl or trifluoroacetyl or $A^2$ and $A^1$ together with $R^1$ and the atoms to which $A^1$ and $R^1$ are attached form a group of Formula (g):

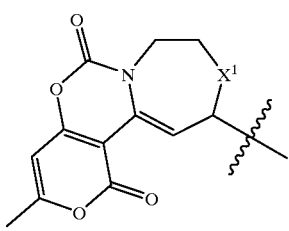
(g)

wherein $X^1$ is —S— and the free valance is attached to $A^3$

Preferred are compounds of Formula I in which $A^1$ is selected from Formulae (b) and (d), wherein $R^7$ is hydrogen, and $A^2$ is selected from Formulae (h) and (i).

Particularly preferred compounds of the invention include:

4-hydroxy-3-[7-(2-methoxy-4-methylsulfanyl-phenyl)-2,3,6,7-tetrahydro-[1,4]thiazepin-5-yl]-6-methyl-pyran-2-one;

4-hydroxy-3-[7-(4-methanesulfonyl-phenyl)-2,3,6,7-tetrahydro-[1,4]thiazepin-5-yl]-6-methyl-pyran-2-one;

3-[2-(2,4-diethoxy-phenyl)-2,3-dihydro-benzo[b][1,4]thiazepin-4-yl]-4-hydroxy-6-methyl-pyran-2-one;

3-[7-(2,4-diethoxy-phenyl)-2,3,6,7-tetrahydro-[1,4]thiazepin-5-yl]-4-hydroxy-6-methyl-5,6-dihydropyran-2-one;

2-[7-(2,4-diethoxy-phenyl)-2,3,6,7-tetrahydro-[1,4]thiazepin-5-yl]-3-hydroxy-cyclohex-2-enone;

3-hydroxy-2-[7-(2,3,4-trimethoxy-phenyl)-2,3,6,7-tetrahydro-[1,4]thiazepin-5-yl]-cyclohex-2-enone; and 3-hydroxy-2-[2-(2,3,4-trimethoxy-phenyl)-2,3-dihydrobenzo[b][1,4]thiazepin-4-yl]-cyclohex-2-enone.

Definitions

Unless otherwise stated, the following terms used in the specification and claims are defined for the purposes of this Application and have the following meanings.

"Alkyl" represented by itself means a straight or branched, saturated or unsaturated, aliphatic radical having the number of carbon atoms indicated (e.g., $(C_{1-6})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl) means a straight or branched, saturated or unsaturated aliphatic divalent radical having the number of atoms indicated or when no atoms are indicated means abond (e.g., $(C_{6-10})$aryl$(C_{0-3})$ alkyl includes phenyl, benzyl, phenethyl, 1-phenylethyl 3-phenylpropyl, and the like).

"Alkylene", unless indicated otherwise, means a straight or branched, saturated or unsaturated, aliphatic, divalent radical having the number of carbon atoms indicated (e.g., $(C_{1-6})$alkylene includes methylene (—$CH_2$—), ethylene (—$CH_2CH_2$—), trimethylene (—$CH_2CH_2CH_2$—), tetramethylene (—$CH_2CH_2CH_2CH_2$—), 2-butenylene (—$CH_2CH=CHCH_2$—), 2-methyltetramethylene (—$CH_2CH(CH_3)CH_2CH_2$—), pentamethylene (—$CH_2CH_2CH_2CH_2CH_2$—) and the like).

"Alkylidene" means a straight or branched saturated or unsaturated, aliphatic, divalent radical having the number of carbon atoms indicated (e.g. $(C_{1-6})$alkylidene includes methylene (=$CH_2$), ethylidene (=$CHCH_3$), isopropylidene (=$C(CH_3)_2$), propylidene (=$CHCH_2CH_3$), allylidene (=CH—CH=$CH_2$), and the like).

"Amino" means the radical —$NH_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are $sp^2$ hybridized and the total number of pi electrons is equal to 4n+2.

"Aryl" means an aromatic, monocyclic or fused bicyclic ring or ring assembly containing the total number of ring carbon atoms indicated, wherein each ring is comprised of 6 ring carbon atoms. Typical aryl groups containing a total of 6 to 14 ring atoms include phenyl, naphthyl, phenanthrenyl, anthracentyl, and the like. By further example, optionally substituted heteroaryl in defining $A^3$ includes 2,4-dimethoxyphenyl, 2-trifluoromethylsulfanylphenyl, 3-trifluoromethylsulfanylphenyl, 4-trifluoromethylsulfanylphenyl, 3-(3-trifluoromethylphenyloxy)phenyl, 3-(3,4-dichlorophenoxy)phenyl, 3-(3,5-dichlorophenoxy)phenyl, 2-chloro-5-trifluoromethylphenyl, 2,4-difluorophenyl, 4-dimethylaminophenyl, 4-trifluoromethoxyphenyl, 2,4-di(trifluoromethyl)phenyl, 4-dimethylamino-2-methoxyphenyl, 4-methylsulfonylphenyl, 2,4-diethoxyphenyl, 2,3,4-trimethoxyphenyl, 2-methoxy-4-methylsulfanylphenyl, and the like.

"Carbocycloalkyl" means a monocyclic, fused bicyclic or bridged polycyclic ring or ring assembly containing the number of ring carbon atoms indicated. "Unsaturated, partially unsaturated or saturated" used in connection with the term carbocycloalkyl refers to instances where the ring or ring assembly is unsaturated and non-aromatic (e.g., cyclooctatetraenyl and the like), partially saturated (e.g., azulenyl, fluorenyl, indenyl,1,2,3,4-tetrahydronaphthyl, and the like) or saturated (e.g, cyclohexyl and the like), respectively.

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted ($C_{1-3}$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom moiety" includes —N=, —NR—, —O—, —S— or —S(O)$_2$—, wherein R is hydrogen, ($C_{1-6}$)alkyl or a protecting group.

"Heteroaryl" means an aromatic, monocyclic or fused bicyclic ring or ring assembly containing the total number of ring atoms indicated, wherein each ring is comprised of 5 or 6 ring atoms and one or more of the ring atoms is a heteroatom moiety selected from —N=, —NR—, —O— or —S—, wherein R is hydrogen, ($C_{1-6}$)alkyl, a protecting group or represents the free valence serving as the point of attachment. For example, aryl containing a total of 5 to 14 ring atoms includes, but is not limited to acridine, benzo[b] thienyl, benzimidazolyl, benzoisoxazolyl, carbazolyl, β-carbolinyl, cinnolinyl, furazanyl, furyl, imidazolyl, indolizinyl, 3H-indolyl, isobenzofuranyl, isoindolyl, isothiazolyl, isoquinolyl, isoxazolyl, naphtho[2,3]thienyl, naphthyridinyl, 2-oxobenzimidaxolyl, perimidinyl, phenanthridinyl, phenazinyl, pteridinyl, purinyl, pyrazolyl, pyridyl, pyrazinyl, pyrimidinyl, pyridazinyl, 2H-pyrrolyl, pyrroyl, quinolyl, quinoxalinyl, thienyl, and the like. By further example, optionally substituted heteroaryl in defining $A^3$ includes 3-phenyl-1H-pyrazol-4-yl, 5-ethylthien-2-yl, 1-benzyl-1H-indol-3-yl, 5-(3-trifluoromethylphenyl)fur-2-yl, 5-(2-chlorophenyl)fur-2-yl, 5-(3-chlorophenyl)fur-2-yl, 5-(4-chlorophenyl)fur-2-yl, 5-(2-chloro-5-trifluoromethylphenyl)fur-2-yl, 4-bromothien-2-yl, 5-bromothien-2-yl, 1-phenylsulfonyl-1H-pyrrol-2-yl, 3-methylfur-2-yl, 5-methylfur-2-yl, 1-methyl-1H-indol-3-yl, 5-chloro-1-methyl-3-trifluoromethyl-1H-pyrrol-5-yl, 4[2,2']bithienyl-5-yl, 1-(3,5-dichloro)pyrrol-2-yl, 1-(4-chloro)pyrrol-2-yl, 5-chloro-1H-indol-3-yl, 6-(4-methylphenylsulfanyl)imidazo[2,1-b]thiazol-5-yl, 4,5-dibromothien-2-yl, 5-methylsulfanylthien-2-yl, 5-chloro-1-methyl-3-phenyl-1H-pyrrol-4-yl, and the like.

"Heteroarylene" means a divalent, aromatic, monocyclic or fused bicyclic ring or ring assembly containing the total number of ring atoms indicated, wherein each ring is comprised of 5 or 6 ring atoms and two or more of the ring atoms are a heteroatom moiety selected from —N=, —NR—, —O— or —S—, wherein R is hydrogen, ($C_{1-6}$)alkyl or a protecting group. For example, aryl containing a total of 5 to 14 ring atoms includes, but is not limited to pyrimidin-2,4-ylene, pyrrolo[1,2-α]pyrimidin-2,4-ylene, and the like.

"Heterocycloalkylene" means a divalent, monocyclic, fused bicyclic or bridged polycyclic ring or ring assembly containing the number of ring atoms indicated, wherein two or more of the ring atoms are a heteroatom moiety selected from —N=, —NR—, —O— or —S—, wherein R is hydrogen, ($C_{1-6}$)alkyl or a protecting group. "Unsaturated, partially unsaturated or saturated" used in connection with the term heterocycloalkylene refers to instances where the ring or ring assembly is unsaturated and non-aromatic (e.g., 1,4-thiazepin-5,7-ylene and the like), partially saturated (e.g., 2,3-dihydro-1,4-thiazepin-5,7-ylene, 2,3-dihydrobenzo[b][1,4]thiazepin-5,7-ylene, 2,3-dihydrobenzo[b][1,4]diazepin-5,7-ylene, and the like) or saturated (e.g, 1,4-thiazepan-5,7-ylene and the like), respectively. For example, optionally substituted heterocycloalkylene used in defining $A^2$ includes 2,3,6,7-tetrahydro[1,4]thiazepin-5,7-ylene, 2,3-dihydrobenzo[b][1,4]thiazepin-5,7-ylene, 4-acetyl[1,4]thiazepan-5,7-ylene, 4-trifluoroacetyl[1,4]thiazepan-5,7-ylene, 2,3-dihydrobenzo[b][1,4]diazepin-5,7-ylene, 2,3-dihydro-1,4-thiazepin-5,7-ylene, 1-oxo-2,3,6,7-tetrahydro[1,4]thiazepin-5,7-ylene, 1,1-dioxo-2,3,6,7-tetrahydro[1,4]thiazepin-5,7-ylene, 3-(1-tert-butoxycarbonylethylcarbamoyl)-2,3,6,7-tetrahydro[1,4]thiazepin-5,7-ylene, and the like.

"Heterocycloalkyl" means a monocyclic, fused bicyclic or bridged polycyclic ring or ring assembly containing the number of ring atoms indicated. wherein one or more of the ring atoms is a heteroatom moiety selected from —N=, —NR—, —O— or —S—, wherein R is hydrogen, ($C_{1-6}$) alkyl or a protecting group. "Unsaturated, partially unsaturated or saturated" used in connection with the term heterocycloalkyl refers to instances where the ring or ring assembly is unsaturated and non-aromatic (e.g., oxepinyl, thiepinyl, and the like), partially saturated (e.g., 2H-pyranyl, 3,6-dihydro-2H-pyran, 1,2-dihydroquinolyl, and the like) or saturated (e.g, tetrahydropyranyl, and the like), respectively. By further example, optionally substituted heterocycloalkyl used in defining $A^1$ includes 4-hydroxy-6-methyl-2-oxo-2H-pyran-3-yl, 4-methoxy-6-methyl-2-oxo-2H-pyran-3-yl, 4-hydroxy-6-methyl-2-oxo-5,6-dihydro-2H-pyran-3-yl, 2-hydroxy-6-oxo-cyclohex-1-enyl, 4-hydroxy-2-oxo-1,2-dihydro-quinolin-3-yl, 7-amino-1-oxo-1H-isochromen-8-yl, 2,3-dioxo-3,4-dihydro-2H-quinoxalin-1-yl, 2-oxo-2,3-dihydro-indol-1-yl, 4-oxo-4H-pyrido[1,2-α]pyrimidin-3-yl, and the like.

"Imino" means the moiety =NR, wherein R is hydrogen or ($C_{1-6}$)alkyl.

"Isomers" mean compounds of Formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula I are meant to be encompassed all possible stereoisomers.

"Nitro" means the radical —$NO_2$.

"Oxo" means the moiety =O.

"Optional" or "optionally" means that the subsequently described event or circumstance may or may not occur, and that the description includes instances where the event or circumstance occurs and instances in which it does not.

"N-Oxide derivatives" means derivatives of compounds of Formula I in which nitrogens are in an oxidized state (i.e., O—N) and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound which is convertible in vivo by metabolic means (e.g. by hydrolysis) to a compound of the invention. For example an ester of a compound of the invention containing a hydroxy group may be convertible by hydrolysis in vivo to the parent molecule. Alternatively an ester of a compound of the invention containing a carboxy group may be convertible by hydrolysis in vivo to the parent molecule. Suitable esters of compounds of the invention containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulphonates, ethanesulphonates, benzenesulphonates, p-toluenesulphonates, cyclohexylsulphamates and quinates. Suitable esters of compounds of the invention containing a carboxy group, are for example those described by F. J. Leinweber, Drug Metab. Res., 1987, 18, page 379. An especially useful class of esters of compounds of the invention containing a hydroxy group, may be formed from acid moieties selected from those described by Bundgaard et al., J. Med. Chem., 1989, 32, page 2503–2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of the invention in which a reactive site or sites are blocked with protecting groups. Protected derivatives of compounds of the invention are useful in the preparation of compounds of the invention or in themselves may be active as activators of the caspase cascade and inducers of apoptosis. A comprehensive list of suitable protecting groups can be found in T. W. Greene, *Protecting Groups in Organic Synthesis*, 3rd edition, John Wiley & Sons, Inc. 1999.

"Therapeutically effective amount" means that amount which, when administered to an animal for treating a disease, is sufficient to effect such treatment for the disease.

"Thioxo" means the moiety=S.

"Treatment" or "treating" means any administration of acompound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

Nomenclature

The compounds of Formulae I and II and the intermediates and starting materials used in their preparation are named in accordance with IUPAC rules of nomenclature in which the characteristic groups have decreasing priority for citation as the principle group, e.g., acids, esters, amides, etc, as determined by AutoNom 4.0 (Beilstein Information Systems, Inc.). For example, a compound of Formula II wherein $A^1$ is 4-hydroxy-6-methyl-2-oxopyran-3-yl, $A^2$ is 2,3,6,7-tetrahydro[1,4]thiazepin-5,7-ylene and $A^3$ is 3-(3,5-dichloro-phenoxy)-phenyl is named 3-{7-[3-(3,5-dichlorophenoxy)-phenyl]-2,3,6,7-tetrahydro-[1,4]thiazepin-5-yl}-4-hydroxy-6-methyl-pyran-2-one. Alternatively, the compound may be referred to as 5-(4-hydroxy-6-methyl-2H-pyran-2-one-3-yl)-7-[3-(3,5-dichloro -phenoxy)-phenyl]-2,3,6,7-tetrahydro-[1,4]thiazepine.

Utility and Pharmacology

Another important aspect of the present invention is the discovery that substituted 1,4-thiazepines and analogs thereof are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, substituted 1,4-thiazepines and analogs thereof are useful for the treatment of drug resistant cancer in animals.

The present invention includes a therapeutic method useful to modulate in vivo apoptosis or in vivo neoplastic disease, comprising administering to a subject in need of such treatment an effective amount of a substituted 1,4-thiazepines or analog thereof, or a pharmaceutically acceptable salt or prodrug thereof, which functions as a caspase cascade activator and inducer of apoptosis.

The present invention also includes a therapeutic method comprising administering to an animal an effective amount of a substituted 1,4-thiazepines or analog thereof, or a pharmaceutically acceptable salt or prodrug thereof, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute and chronic lymphocytic leukemias, multiple myeloma, neuroblastoma, breast carcinomas, ovarian carcinomas, lung carcinomas, Wilms' tumor, cervical carcinomas, testicular carcinomas, soft tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyo sarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms.

In another embodiment, a pharmaceutical composition comprising a substituted 1,4-thiazepines or analog thereof, or a pharmaceutically acceptable salt thereof, which functions as a caspase cascade activator and inducer of apoptosis in combination with a pharmaceutically acceptable vehicle is provided.

Another embodiment of the present invention is directed to a composition effective to inhibit neoplasia comprising a substituted 1,4-thiazepines or analog thereof, or a pharmaceutically acceptable salt or prodrug thereof, which functions as a caspase cascade activator and inducer of apoptosis, in combination with at least one known cancer chemotherapeutic agent, or a pharmaceutically acceptable salt of said agent. Examples of known anticancer agents which can be used for combination therapy include, but are not limit to alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; and antibodies such as Herceptin® and Rituxan®. Other known anti-cancer agents which can be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the substituted 1,4-thiazepines or analog thereof may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in the blood at the same time. In another embodiment, the compound of the invention and at least one known cancer chemotherapeutic agent are administered according to their individual dose schedule, so long as the compounds reach therapeutic levels in the blood.

Another embodiment of the present invention is directed to a composition effective to inhibit neoplasia comprising a bioconjugates of the substituted 1,4-thiazepines or analogs thereof, which functions as a caspase cascade activator and inducer of apoptosis, in bioconjugation with at least one known therapeutically useful antibody, such as Herceptin® or Rituxan®, growth factor such as DGF or NGF, cytokines such as IL-2 or IL-4, or any other molecule that binds to a cell surface receptor. These conjugates can be made using functional groups of the substituted 1,4-thiazepines or analogs thereof. For example. when one of the R groups is a carboxylic acid, it can be used to modify the amino group on the proteins, to produced a drug-protein conjugate. For example, the N-hydroxysuccinamide ester of the carboxy-containing compound may be prepared which may be condensed with the protein. See *Anal. Biochem* 87:218 (1994)

and *Polycyclic Aromat. Compd* 3:781 (1993). The antibodies and other molecules will deliver the substituted 1,4-thiazepine or analog thereof to its targets and make them more effective anticancer agents. The bioconjugates also may enhance the anticancer effect of therapeutically useful antibodies, such as Herceptin® or Rituxan®.

Similarly, another embodiment of the present invention is directed to a composition effective to inhibit neoplasia comprising a substituted 1,4-thiazepine or analog thereof, or a pharmaceutically acceptable salt or prodrug thereof, which functions as a caspase cascade activator and inducer of apoptosis, in combination with radiation therapy. In this embodiment, the substituted 1,4-thiazepine or analog thereof may be administered at the same time as the radiation therapy is administered or at a different time.

Yet another embodiment of the present invention is directed to a composition effective for post-surgical treatment of cancer, comprising a substituted 1,4-thiazepine or analog thereof, or a pharmaceutically acceptable salt or prodrug thereof, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cell has been shown to be regulated by a phenomenon known as apoptosis. Autoimmune diseases have been lately identified as a consequence of deregulated cell death. In certain autoimmune diseases, the immune system directs its powerful cytotoxic effector mechanisms against specialized cells such as oligodendrocytes in multiple sclerosis, the beta cells of the pancreas in diabetes mellitus, and thyrocytes in Hashimoto's thyroiditis (Ohsako. S. & Elkon, K. B., *Cell Death Differ.* 6:13–21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation (Infante, A. J., et al., *J Pediatr.* 133:629–633 (1998) and Vaishnaw, A. K., et al., *J Clin. Invest.* 103:355–3)63 (1999)). Overexpression of Bcl-2, which is a member of the bcl-2 gene family of programmed cell death regulators with anti-apoptotic activity in developing B cells of transgenic mice, in the presence of T cell dependent co-stimulatory signals, results in the generation of a modified B cell repertoire and in the production of pathogenic autoantibodies (Lopez-Hoyos, M., et al., *Int. J MoL Med.* 1:475–483 (1998)). Accordingly, many types of autoimmune disease may be caused by defects of the apoptotic process, and one treatment strategy would be to turn on apoptosis in the lymphocytes that are causing autoimmune disease (O'Reilly, L. A. & Strasser, A., *Inflamm. Res.* 48:5–21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J Immunol.* 162:603–608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321NI cells and in Molt-4T cells, and both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., el al., (*Nat. Med* 5:42–49 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore the application of a Fas-dependent apoptosis enhancer such as bisindolylmaleimide VIII may be therapeutically useful for the more effective elimination of detrimental cells and inhibition of T cell-mediated autoimmune diseases. Therefore an effective amount of a substituted 1,4-thiazepines or analog thereof, or a pharmaceutically acceptable salt or prodrug thereof, which functions as a caspase cascade activator and inducer of apoptosis, should be an effective treatment for autoimmune disease Psoriasis is a chronic skin disease that is characterized by scaly red patches. Psoralen plus ultraviolet A (PUVA) is a widely used and effective treatment for psoriasis vulgaris and Coven, et al., *Photodermatol. Photoimmunol. Photomed* 15:22–27 (1999), reported that lymphocytes treated with psoralen 8-MOP or TMP plus UVA displayed DNA degradation patterns typical of apoptotic cell death. Ozawa, et al., *J Exp. Med* 189:711–718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240–245 (1998), reported that low doses of methotrexate may induce apoptosis and this mode of action could explain the reduction in epidermal hyperplasia during treatment of psoriasis with methotrexate. Therefore an effective amount of a substituted 1,4-thiazepine or analog thereof, or a pharmaceutically acceptable salt or prodrug thereof, which functions as a caspase cascade activator and inducer of apoptosis, should be an effective treatment for psoriasis.

Synovial cell hyperplasia is a characteristic of patients with rheumatoid arthritis (RA). Excessive proliferation of RA synovial cells as well as defects in synovial cell death might be responsible for the synovial cell hyperplasia. Wakisaka, et al., *Clin. Exp. Immunol.* 114:119–128 (1998), found that although RA synovial cells could die via apoptosis through Fas/FasL pathway, apoptosis of synovial cells was inhibited by proinflammatory cytokines present within the synovium, and suggested that inhibition of apoptosis by the proinflammatory cytokines may contribute to the outgrowth of synovial cells, and lead to pannus formation and the destruction of joints in patients with RA. Therefore an effective amount of a substituted 1,4-thiazepine or analog thereof, or a pharmaceutically acceptable salt or prodrug thereof, which functions as a caspase cascade activator and inducer of apoptosis, should be an effective treatment for rheumatoid arthritis.

An accumulation of convincing evidence suggests that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J Leukoc. Biol.* 61:375–380 (1997)). Boirivant, et al., *Gastroenterology* 116:557–565 (1999), reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue indicate that this defect is accompanied by elevated Bcl-2 levels. Therefore an effective amount of a substituted 1,4-thiazepines or analog thereof, or a pharmaceutically acceptable salt or prodrug thereof, which functions as a caspase cascade activator and inducer of apoptosis, should be an effective treatment for inflammation and inflammatory bowel disease.

Compositions within the scope of this invention include all compositions wherein the caspase cascade activators are contained in an amount that is effective to achieve its intended purpose. While individual needs vary, determination of optimal ranges of effective amounts of each component is within the skill of the art. Typically, the active compounds may be administered to mammals, e.g., humans, orally at a dose of 0.0025 to 50 mg/kg, or an equivalent amount of the pharmaceutically acceptable salt thereof, per day of the body weight of the mammal being treated for apoptosis mediated disorders. Preferably, about 0.01 to about 10 mg/kg is orally administered to treat or prevent such disorders. For intramuscular injection, the dose is generally about one-half of the oral dose. For example, a suitable intramuscular dose would be about 0.0025 to about 25 mg/kg, and most preferably, from about 0.01 to about 5 mg/kg. If a known cancer chemotherapeutic agent is also administered, it is administered in an amount with is effective to achieve its intended purpose. The amounts of such known cancer chemotherapeutic agents effective for cancer are well known to those of skill in the art.

The unit oral dose may comprise from about 0.01 to about 50 mg, preferably about 0.1 to about 10 mg of the caspase cascade activator. The unit dose may be administered one or more times daily as one or more tablets each containing from about 0.1 to about 10, conveniently about 0.25 to 50 mg of the compound or its solvates. In a topical formulation, the caspase cascade activator may be present at a concentration of about 0.01 to 100 mg per gram of carrier.

In addition to administering the caspase cascade activator as a raw chemical, the caspase cascade activator may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the nontoxic pharmaceutically acceptable salts of the compounds of the present invention. Acid addition salts are formed by mixing a solution of the particular apoptosis inducer with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base such as sodium hydroxide, potassium hydroxide, choline hydroxide, sodium carbonate, Tris, N-methyl-glucamine and the like.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastricjuices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses. Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added. Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons. Suitable formulations for parenteral administration include aqueous solutions of the active compounds in water-soluble form, for example, water soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension, and include, for example, sodium carboxymethyl cellulose, sorbitol, and/or dextran. Optionally, the suspension may also contain stabilizers. In accordance with one aspect of the present invention, substituted 1,4-thiazepines or analogs thereof, or a pharmaceutically acceptable salt or prodrug thereof, are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Accordingly, an aspect of the present invention is a method of treating a disorder responsive to the induction of apoptosis in an animal suffering from said disorder, which method comprises administering to the animal an effective amount of a compound of Formula I:

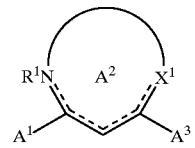

in which:
the dashed lines indicate optional unsaturation without violating valency rules;
$R^1$ is hydrogen, $(C_{1-6})$alkyl or $—C(O)R^6$, wherein $R^6$ is as defined below, or is absent when a double bond exists between the nitrogen atom to which $R^1$ is attached and an adjacent ring atom or $R^1$ is as defined below;
$X^1$ is $—NR^2—$, $—S—$, $—S(O)—$, $—S(O)_2—$ or $—O—$, wherein $R^2$ is hydrogen or $(C_{1-6})$alkyl or is absent when a double bond exists between the nitrogen atom to which $R^2$ is attached and an adjacent ring atom;
$A^1$ is a monocyclic or fused polycyclic ring system selected from aryl containing a total of 6 to 14 ring atoms, heteroaryl containing a total of 5 to 14 ring atoms and unsaturated, partially unsaturated or saturated carbocycloalkyl or heterocycloalkyl each containing a total of 3 to 14 ring atoms, or $A^1$ together with $R^1$ and the atoms to which $A^1$ and $R^1$ are attached forms a fused polycyclic ring system selected from heteroaryl and unsaturated, partially unsaturated or saturated heterocycloalkyl in any case containing a total of 10 to 15 ring atoms, wherein $A^1$ may be substituted with a group selected from $—R^3$, $—X^2OR^3$, $—X^2C(O)R^3$, $—X^2OC(O)R^3$, $—X^2C(O)OR^3$, $—X^2SR^3$, $—X^2S(O)R^3$, $—X^2S(O)_2R^3$, $—X^2NR^3R^4$, $—X^2NR^4C(O)R^3$, $—X^2NR^4C(O)OR^3$, $—X^2C(O)NR^3R^4$, $—X^2NR^4C(O)NR^3R^4$, $—X^2NR^4C(NR^4)NR^3R^4$, $—X^2NR^4S(O)_2R^3$ and $—X^2S(O)_2NR^3R^4$, wherein $X^2$ is a bond or $(C_{1-6})$alkylene, $R^3$ is $—X^2R^5$ wherein $X^2$ is as defined above and $R^5$ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and $R^4$ at each occurrence independently is hydrogen, $(C_{1-6})$alkyl or halo-substituted $(C_{1-6})$alkyl, wherein each ring within $A^1$ and $R^5$ contains from 3 to 8 ring atoms and may be substituted with 1 to 3 groups independently selected from $(C_{1-6})$alkyl, cyano, halo, nitro, halo-substituted $(C_{1-6})$alkyl, $—X^2OR^4$, $—X^2C(O)R^6$, $—X^2OC(O)R^6$, $—X^2C(O)OR^4$, $—X^2SR^4$, $—X^2S(O)R^6$, $—X^2S(O)_2R^6$, $—X^2NR^4R^4$, $—X^2NR^4C(O)R^6$, $—X^2NR^4C(O)OR^4$, $—X^2C(O)NR^4R^4$, $—X^2NR^4C(O)NR^4R^4$, $—X^2NR^4C(NR^4)NR^4R^4$, $—X^2NR^4S(O)_2R^6$ and $—X^2S(O)_2NR^4R^4$, wherein $X^2$ and $R^4$ are as defined above and $R^6$ is $(C_{1-6})$alkyl or halo-substituted $(C_{1-6})$alkyl, and wherein any said carbocycloalkyl and heterocycloalkyl rings within $A^1$ and $R^5$ may be substituted further with 1 to 2 groups independently selected from $(C_{1-6})$alkylidene, oxo, imino and thioxo, with the provisos that only one of $A^1$ and $R^5$ is a fused polycyclic ring system;

$A^2$ is a monocyclic or fused bicyclic ring selected from heteroarylene or unsaturated, partially unsaturated or saturated heterocycloalkylene containing a total of 5 to 11 ring atoms, wherein $A^2$ may be substituted with a group selected from $—R^8$, $—X^2OR^8$, $—X^2C(O)R^8$, $—X^2OC(O)R^8$, $—X^2C(O)OR^8$, $—X^2SR^8$, $—X^2S(O)R^8$, $—X^2S(O)_2R^8$, $—X^2NR^4R^8$, $—X^2NR^4C(O)R^8$, $—X^2NR^4C(O)OR^8$, $—X^2C(O)NR^4R^8$, $—X^2NR^4C(O)NR^4R^8$, $—X^2NR^4C(NR^4)NR^4R^8$, $—X^2NR^4S(O)_2R^8$ and $—X^2S(O)_2NR^4R^8$, wherein $X^2$ is a bond or $(C_{1-6})$ alkylene, $R^8$ is —$X^2R^9$ wherein $X^2$ is as defined above and $R^9$ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and $R^4$ at each occurrence independently is hydrogen, (C1-6)alkyl or halo-substituted $(C_{1-6})$alkyl, wherein each ring within $A^2$ and $R^8$ contains from 3 to 8 ring atoms and may be substituted with 1 to 3 groups independently selected from $(C_{1-6})$ alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR^4C(O)NR^4R^4$, —$X^2NR^4C(NR^4)NR^4R^4$, —$X^2C(O)NR^4X^2C(O)OR^4$, —$X^2NR^4S(O)_2R^6$ and —$X^2S(O)_2NR^4R^4$, wherein $x^2$ and $R^4$ are as defined above and $R^6$ is $(C_{1-6})$alkyl or halo-substituted $(C_{1-6})$alkyl, and wherein any said heterocycloalkylene, carbocycloalkyl and heterocycloalkyl rings within $A^2$ and $R^8$ may be substituted further with 1 to 2 groups independently selected from $(C_{1-6})$alkylidene, oxo, imino and thioxo, with the proviso that only one of $A^2$ and $R^8$ is a fused polycyclic ring system; and $A^3$ is a monocyclic or fused polycyclic ring system selected from aryl containing a total of 6 to 14 ring atoms, heteroaryl containing a total of 5 to 14 ring atoms and unsaturated, partially unsaturated or saturated carbocycloalkyl or heterocycloalkyl each containing a total of 3 to 14 ring atoms, wherein $A^3$ may be substituted with a group selected from —$R^9$, —$X^2R^9$, —$X^2C(O)R^9$, —$X^2C(O)R^9$, —$X^2C(O)OR^9$, —$X^2SR^9$, —$X^2S(O)R^9$, —$X^2S(O)_2R^9$, —$X^2NR^4R^9$, —$X^2NR^4C(O)R^9$, —$X^2NR^4C(O)OR^9$, —$X^2C(O)NR^4R^9$, —$X^2NR^4C(O)NR^4R^9$, —$X^2NR^4C(NR^4)NR^4R^9$, —$X^2NR^4S(O)_2R^9$ and —$X^2S(O)_2NR^4R^9$, wherein $X^2$ is a bond or $(C_{1-6})$alkylene, $R^9$ is —$X^2R^{10}$ wherein $X^2$ is as defined above and $R^{10}$ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and $R^4$ at each occurrence independently is hydrogen, $(C_{1-6})$alkyl or halo-substituted $(C_{1-6})$alkyl, wherein each ring within $A^3$ and $R^{10}$ contains from 3 to 8 ring atoms and may be substituted with 1 to 3 groups independently selected from $(C^{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR^4C(O)NR^4R^4$, —$X^2NR^4C(NR^4)NR^4R^4$, —$X^2NR^4S(O)_2R^6$ and —$X^2S(O)_2NR^4R^4$, wherein $X^2$ and $R^4$ are as defined above and $R^6$ is $(C_{1-6})$alkyl or halo-substituted $(C_{1-6})$alkyl, and wherein any said carbocycloalkyl and heterocycloalkyl rings within $A^3$ and $R^{10}$ may be substituted further with 1 to 2 groups independently selected from $(C_{1-4})$ alkylidene, oxo, imino and thioxo, with the proviso that only one of $A^3$ and $R^{10}$ is a fused polycyclic ring system; or an N-oxide derivative, prodrug derivative, protected derivative, individual stereoisomer or mixture of stereoisomers, or a pharmaceutically acceptable salt thereof; with the proviso that when said compound is of Formula II(a):

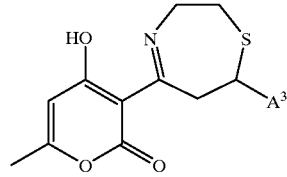

II(a)

then $A^3$ is other than:
(a) benzo[1,3]dioxolyl;
(b) phenyl which is mono-substituted by bromo, hydroxy, methyl or isopropyl; and
(c) phenyl which is substituted by at least one of chloro and methoxy and not substituted by methylsulfanyl, amino, methylamino or dimethylamino; preferably wherein said disorder is an autoimmune disease, in particular rheumatoid arthritis, or inflammation or inflammatory bowel disease, in particular, wherein said disorder is psoriasis or a skin disease.

Another aspect of the present invention is a method for treating or preventing cancer, comprising administering to an animal in need of such treatment an effective amount of a compound of Formula I as defined immediately above; particularly wherein said cancer is selected from the group consisting of Hodgkin's disease, non-Hodgkin's lymphoma, acute and chronic lymphocytic leukemias, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head and neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer and prostatic carcinoma.

Another aspect of the present invention is a method for the treatment of drug resistant cancer, comprising administering to an animal in need of such treatment an effective amount of a compound of compound of Formula I as defined immediately above.

Preferred means for practicing any of the above methods comprises further administering to said animal at least one known cancer chemotherapeutic agent, or a pharmaceutically acceptable salt of said agent; preferably wherein said known cancer therapeutic agent is selected from the group consisting of busulfan, cis-platin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, imitoxantrone, elliptinium, fludarabine, octreotide, retinoic acid, tamoxifen, Herceptin®, Rituxan® and alanosine.

Preferred means for practicing any of the above methods comprises further treating said animal with radiation-therapy.

Preferred means for practicing any of the above methods comprises administering the compound of Formula I after surgical treatment for cancer.

Preferred means for practicing any of the above methods comprises administering a compound of Formula I which when said compound is selected from the group consisting of Formula II(a) and II(b):

II(a)

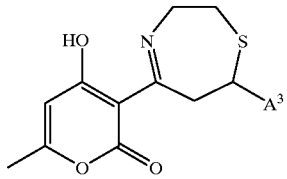

II(b)

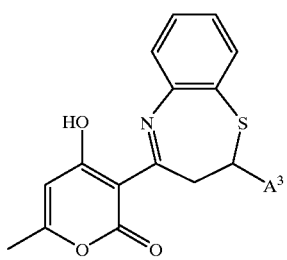

then $A^3$ is other than:

(a) benzo[1,3]dioxolyl;
(b) phenyl which is mono-substituted by bromo, nitro, hydroxy, methyl or isopropyl; and
(c) phenyl which is substituted by at least one of Cl and methoxy and not substituted by methylsulfanyl, amino, methylamino and dimethylamino A further preferred means for practicing any of the above methods comprises administering a compound of Formula I which when said compound is selected from the group consisting of Formula II(a) and II(b), then $A^3$ is other than benzo[1,3]dioxol-5-yl, 2,3-dihydro-benzo[1,4]dioxinyl or phenyl which is substituted by at least one of bromo, chloro, hydroxy, nitro, methoxy and $(C_{1-3})$ alkyl A further preferred means for practicing any of the above methods comprises administering a compound of Formula I in which $A^1$ of said compound is a group selected from Formulae (a), (b), (c), (d) and (e):

(a)

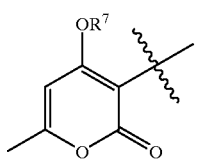

(b)

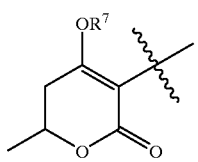

(c)

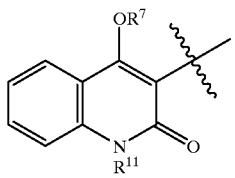

(d)

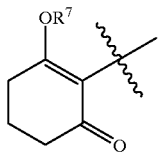

(e)

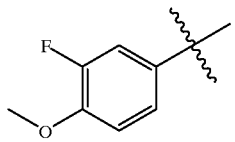

in which $R^7$ is hydrogen or methyl, $R^{11}$ is hydrogen or $(C_{1-6})$alkyl and the free valance is attached to $A^2$, or $A^2$ and $A^1$ together with $R^1$ and the atoms to which $A^1$ and $R^1$ are attached forms a group of Formula (g):

(g)

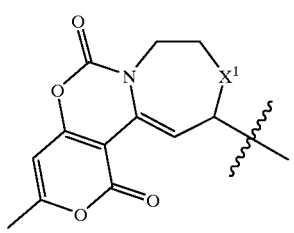

wherein $X^1$ is —S— and the free valance is attached to $A^3$; and $A^2$ of said compound is as defined above or is a group selected from Formulae (h), (i), (j), (k), (l) and (m):

(h)

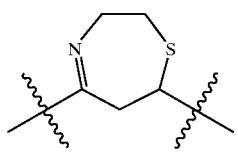

(i)

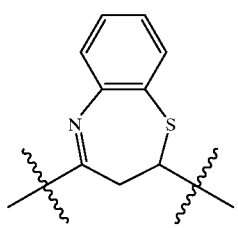

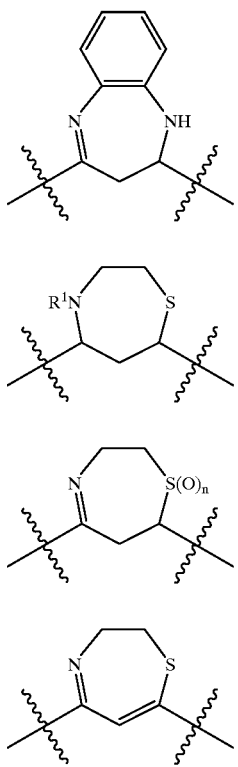

(j)

(k)

(l)

(m)

in which n is 1 or 2 and $R^1$ is acetyl or trifluoroacetyl.

A further preferred means for practicing any of the above methods comprises administering a compound of Formula I in which $A^3$ is phenyl or heteroaryl containing a total of 5 to 9 ring atoms, wherein $A^3$ may be substituted with a group selected from —$R^9$, —$X^2OR^9$, —$X^2SR^9$ and —$X^2S(O)_2R^9$, wherein $R^9$ is —$X^2R^{10}$, $X^2$ is a bond or ($C_{1-6}$alkylene and $R^{10}$ is phenyl or heteroaryl containing a total of 5 to 6 ring atoms, wherein each ring within $A^3$ and $R^{10}$ may be substituted with 1 to 3 groups independently selected from ($C_{1-6}$)alkyl, halo, halo-substituted ($C_{1-6}$)alkyl, —$X^2OR^4$, —$X^2SR^4$, —$X^2S(O)_2R^6$ and —$X^2NR^4R^4$, wherein $R^4$ at each occurrence independently is hydrogen, ($C_{1-6}$)alkyl or halo-substituted ($C_{1-6}$)alkyl and $R^6$ is ($C_{1-6}$)alkyl or halo-substituted ($C_{1-6}$)alkyl.

A further preferred means for practicing any of the above methods comprises administering a compound of Formula I, wherein said compound is selected from the group consisting of:

4-hydroxy-3-[7-(2-methoxy4-methyl sulfanyl-phenyl)-2,3,6,7-tetrahydro-[1,4]thiazepin-5-yl]-6-methyl-pyran-2-one;
2-[7-(2,4-dimethoxy-phenyl)-2,3,6,7-tetrahydro-[1,4]thiazepin-5-yl]-3-hydroxy-cyclohex-2-enone;
4-hydroxy-3-[7-(4-methanesulfonyl-phenyl)-2,3,6,7-tetrahydro-[1,4]thiazepin-5-yl]-6-methyl-pyran-2-one;
3-[2-(2,4-diethoxy-phenyl)-2,3-dihydro-benzo[b][1,4]thiazepin-4-yl]-4-hydroxy-6-methyl-pyran-2-one;
3-[7-(2,4-diethoxy-phenyl)-2,3,6,7-tetrahydro-[1,4]thiazepin-5-yl]-4-hydroxy-6-methyl-5 ,6-dihydro-pyran-2-one;
3-[7-(4-dimethylamino-phenyl)-2,3,6,7-tetrahydro-1,4]thiazepin-5-yl]-4-hydroxy-6-methyl-5,6-dihydro-pyran-2-one;
2-[7-(2,4-diethoxy-phenyl)-2,3,6,7-tetrahydro-[1,4]thiazepin-5-yl]-3-hydroxy-cyclohex-2-enone;
3-hydroxy-2-[7-(2,3,4-trimethoxy-phenyl)-2,3,6,7-tetrahydro-[1,4]thiazepin-5-yl]-cyclohex-2-enone;
3-hydroxy-2-[2-(2,3,4-trimethoxy-phenyl)-2,3-dihydro-benzo[b][1,4]thiazepin-4-yl]-cyclohex-2-enone;
4-hydroxy-6-methyl-3-[2-(2,3,4-trimethoxy-phenyl)-2,3-dihydro-benzo[b][1,4]thiazepin-4-yl]-5,6-dihydro-pyran-2-one;
4-hydroxy-6-methyl-3-[7-(2,3,4-trimethoxy-phenyl)-2,3,6,7-tetrahydro-[1,4]thiazepin-5-yl]-5,6-dihydro-pyran-2-one; and
3-[7-(2,4-dimethoxy-phenyl)-2,3-dihydro-[1,4]thiazepin-5-yl]4-hydroxy-6-methyl-pyran-2-one;

A further preferred means for practicing any of the above methods comprises administering a compound of Formula I, wherein said compound is selected from the group consisting of:

3-[4-acetyl-7-(2,4-dimethoxy-phenyl)-[1,4]thiazepan-5-yl]-4-hydroxy-6-methyl-pyran-2-one;
3-[7-(2,4-dimethoxy-phenyl)-4-(2,2,2-trifluoro-ethanoyl)-[1,4]thiazepan-5-yl]-4-hydroxy-6-methyl-pyran-2-one;
1-[7-(2,4-dimethoxy-phenyl)-5-(3-fluoro-4-methoxyphenyl)-[1,4]thizepan-4-yl]-ethanone;
4-hydroxy-6-methyl-3-[7-(3-phenyl-1H-pyrazol4-yl)-2,3,6,7-tetrahydro-[1,4]thiazepin-5-yl]-pyran-2-one;
3-[7-(5-ethyl-thien-2-yl)-2,3,6,7-tetrahydro-[1,4]thiazepin-5-yl]-4-hydroxy-6-methyl-pyran-2-one;
3-[7-(1-benzyl-1H-indol-3-yl)-2,3,6,7-tetrahydro-[1,4]thiazepin-5-yl]-4-hydroxy-6-methyl-pyran-2-one;
4-hydroxy-6-methyl-3[7-(2-trifluoromethylsulfanyl-phenyl)-2,3,6,7-tetrahydro-[1,4]thiazepin-5-yl]-pyran-2-one;
4-hydroxy-6-methyl-3[7-(3-trifluoromethylsulfanyl-phenyl)-2,3,6,7-tetrahydro-[1,4]thiazepin-5-yl]-pyran-2-one;
4-hydroxy-6-methyl-3[7-(4-trifluoromethylsulfanyl-phenyl)-2,3,6,7-tetrahydro-[1,4]thiazepin-5-yl]-pyran-2-one;
4-hydroxy-6-methyl-3-[7-[3-(3-trifluoromethyl-phenoxy)-phenyl]-2,3,6,7-tetrahydro-[1,4]thiazepin-5-yl]-pyran-2-one;
3-[7-[3-(3,4-dichloro-phenoxy)-phenyl]-2,3,6,7-tetrahydro-[1,4]thiazepin-5-yl]-4-hydroxy-6-methyl-pyran-2-one;
3-[7-[3-(3,5-dichloro-phenoxy)-phenyl]-2,3,6,7-tetrahydro-[1,4]thiazepin-5-yl]-4-hydroxy-6-methyl-pyran-2-one;
4-hydroxy-6-methyl-3-{7-[5-(3-trifluoromethyl-phenyl)-furan-2-yl]-2,3,6,7-tetrahydro-[1,4]thiazepin-5-yl}-pyran-2-one;
3-{7-[5-(2-chloro-phenyl)-furan-2-yl]-2,3,6,7-tetrahydro-[1,4]thiazepin-5-yl}-4-hydroxy-6-methyl-pyran-2-one;
3-{7-[5-(3-chloro-phenyl)-furan-2-yl]-2,3,6,7-tetrahydro-[1,4]thiazepin-5-yl}-4-hydroxy-6-methyl-pyran-2-one;
3-{7-[5-(4-chloro-phenyl)-furan-2-yl]-2,3,6,7-tetrahydro-[1,4]thiazepin-5-yl}-4-hydroxy-6-methyl-pyran-2-one;
4-hydroxy-6-methyl-3-{7-[5-(chloro-trifluoromethyl-phenyl)-furan-2-yl]-2,3,6,7-tetrahydro-[1,4]thiazepin-5-yl}-pyran-2-one;
3-[7-(4-bromo-thien-2-yl)-2,3,6,7-tetrahydro-[1,4]thiazepin-5-yl]-4-hydroxy-6-methyl-pyran-2-one;

3-[7-(5-bromo-thien-2-yl)-2,3,6,7-tetrahydro-[1,4]
thiazepin-5-yl]-4-hydroxy-6-methyl-pyran-2-one;

3-[7-(1-benzenesulfonyl-1H-pyrrol-2-yl)-2,3,6,7-
tetrahydro-[1,4]thiazepin-5-yl]-4-hydroxy-6-methyl-
pyran-2-one;

4-hydroxy-6-methyl-3-[7-(3-methyl-thien-2-yl)-2,3,6,7-
tetrahydro-[1,4]thiazepin-5-yl]-pyran-2-one;

4-hydroxy-6-methyl-3-[7-(5-methyl-thien-2-yl)-2,3,6,7-
tetrahydro-[1,4]thiazepin-5-yl]-pyran-2-one;

4-hydroxy-6-methyl-3-[7-(1-methyl-1H-indol-3-yl)-2,3,
6,7-tetrahydro-[1,4]thiazepin-5-yl]-pyran-2-one;

3-[7-(chloro-methyl-trifluoromethyl-1H-pyrazol-4-yl)-2,
3,6,7-tetrahydro-[1,4]thiazepin-5-yl]-4-hydroxy-6-
methyl-pyran-2-one;

3-{7-[1-(2,4-difluoro-benzenesulfonyl)-1H-pyrrrol-2-yl]-
2,3,6,7-tetrahydro-[1,4]thiazepin-5-yl }4-hydroxy-6-
methyl-pyran-2-one;

3-(7-[2,2']bithienyl-5-yl-2,3,6,7-tetrahydro-[1,4]
thiazepin-5-yl)-4-hydroxy-6-methyl-pyran-2-one;

3-{7-[1-(3,5-dichloro-phenyl)-1H-pyrrrol-2-yl]-2,3,6,7-
tetrahydro-[1,4]thiazepin-5-yl }-4-hydroxy-6-methyl-
pyran-2-one;

3-{7-[1-(4-chloro-phenyl)-1H-pyrrrol-2-yl]-2,3,6,7-
tetrahydro-[1,4]thiazepin-5-yl }-4-hydroxy-6-methyl-
pyran-2-one;

3-[7-(5-chloro-1H-indol-3-yl)-2,3,6,7-tetrahydro-[1,4]
thiazepin-5-yl]-4-hydroxy-6-methyl-pyran-2-one;

4-hydroxy-6-methyl-3-[7-(6-p-tolylsulfanyl-imidazo[2,1-
b]thiazol-5-yl)-2,3,6,7-tetrahydro-[1,4]thiazepin-5-yl]-
pyran-2-one;

3-[7-(4,5-dibromo-thien-2-yl)-2,3,6,7-tetrahydro-[1,4]
thiazepin-5-yl]-4-hydroxy-6-methyl-pyran-2-one;

3-[7-(2-chloro-5-trifluoromethyl-phenyl)-2,3,6,7-
tetrahydro-[1,4]thiazepin-5-yl]-4-hydroxy-6-methyl-
pyran-2-one;

3-[7-(2,4-dimethoxy-phenyl)-2,3,6,7-tetrahydro-[1,4]
thiazepin-5-yl]-4-hydroxy-6-methyl-5,6-dihydro-
pyran-2-one;

4-hydroxy-6-methyl-3-[7-(5-methylsulfanyl-thien-2-yl)-
2,3,6,7-tetrahydro-[1,4]thiazepin-5-yl]-pyran-2-one;

3-[7-(5-chloro-1-methyl-3-phenyl-1H-pyrazol-4-yl)-2,3,
6,7-tetrahydro-[1,4]thiazepin-5-yl]-4-hydroxy-6-
methyl-pyran-2-one;

3-[4-(2,4-dimethoxy-phenyl)-4,5-dihydro-3H-benzo[b]
[1,4]diazepin-2-yl]-4-hydroxy-6-methyl-pyran-2-one;

3-[7-(4-dimethylamino-phenyl)-2,3,6,7-tetrahydro-[1,4]
thiazepin-5-yl]4-hydroxy-6-methyl-pyran-2-one;

3-[7–2,4-dimethoxy-phenyl)-2,3,6,7-tetrahydro-[1,4]
thiazepin-5-yl]-4-hydroxy-1H-quinolin-2-one;

4-hydroxy-6-methyl-3-[7-(4-trifluoromethoxy-phenyl)-2,
3,6,7-tetrahydro-[1,4]thiazepin-5-yl]-pyran-2-one;

3-[7-(bis-trifluoromethyl-phenyl)-2,3,6,7-tetrahydro-[1,
4]thiazepin-5-yl]-4-hydroxy-6-methyl-pyran-2-one;

3-[7-(4-dimethylamino-2-methoxy-phenyl)-2,3,6,7-
tetrahydro-[1,4]thiazepin-5-yl]-4-hydroxy-6-methyl-
pyran-2-one;

3-hydroxy-2-[2-(2,4-diethoxy-phenyl)-2,3-dihydro-
benzo[b][1,4]thiazepin-4-yl]-cyclohex-2-enone;

3-[7-(2,4-dimethoxy-phenyl)-1-oxo-2,3,6,7-tetrahydro-
1H-1λ⁴-[1,4]thiazepin-5-yl]-4-hydroxy-6-methoxy-
pyran-2-one;

10-(2,4-dimethoxy-phenyl)-3-methyl-7,8-dihydro-10H-
2,5-dioxa-9-thia-6a-aza-cyclohepta[a]naphthalene-1,6-
dione;

3-[7-(2,4-dimethoxy-phenyl)-1,1-dioxo-2,3,6,7-
tetrahydro-1H-1λ⁶-[1,4]thiazepin-5-yl]-4-hydroxy-6-
methyl-pyran-2-one;

3-[7-(2,4-diethoxy-phenyl)-2,3-dihydro-[1,4]thiazepin-5-
yl]4-hydroxy-6-methyl-pyran-2-one;

3-(7-[2,2']bithienyl-5-yl-2,3-dihydro-[1,4]thiazepin-5-
yl)-4-hydroxy-6-methyl-pyran-2-one;

2-[7-(2,4-diethoxy-phenyl)-2,3-dihydro-[1,4]thiazepin-5-
yl]-3-hydroxy-cyclohex-2-enone; and 3-[7-(2,4-diethoxy-phenyl)-2,3-dihydro-[1,4]thiazepin-5-
yl]4-hydroxy-6-methyl-5,6-dihydro-pyran-2-one.

A further preferred means for practicing any of the above
methods comprises administering a compound of Formula I,
wherein said compound is selected from the group consist-
ing of:

4-hydroxy-6-methyl-3-[7-(4-methylsulfanyl-phenyl)-2,3,
6,7-tetrahydro-[1,4]thiazepin-5-yl]-pyran-2-one;

3-[7-(4-ethoxy-phenyl)-2,3,6,7-tetrahydro-[1,4]
thiazepin-5-yl]-4-hydroxy-6-methyl-pyran-2-one;

3-[7-(3-methoxy-phenyl)-2,3,6,7-tetrahydro-[1,4]
thiazepin-5-yl]-6-methyl-pyran-2-one;

3-[7-(2-bromo-phenyl)-2,3,6,7-tetrahydro-[1,4]thiazepin-
5-yl]4-hydroxy-6-methyl-pyran-2-one;

3-[7-(2,3-dichloro-phenyl)-2,3,6,7-tetrahydro-[1,4]
thiazepin-5-yl]4-hydroxy-6-methyl-pyran-2-one;

3-[7-(3,4-dichloro-phenyl)-2,3,6,7-tetrahydro-[1,4]
thiazepin-5-yl]-4-hydroxy-6-methyl-pyran-2-one;

6-methyl-3-[7-(2,3,4-trimethoxy-phenyl)-2,3,6,7-
tetrahydro-[1,4]thiazepin-5-yl]-pyran-2-one;

6-methyl-3-(2-p-tolyl-2,3-dihydro-benzo[b][1,4]
thiazepin4-yl)-pyran-2-one;

4-hydroxy-6-methyl-3-[2-(4-methylsulfanyl-phenyl)-2,3-
dihydro-benzo[b][1,4]thiazepin-4-yl]-pyran-2-one.

A further preferred means for practicing any of the above
methods comprises administering a compound of Formula I,
wherein said compound is selected from the group consist-
ing of:

4-hydroxy-6-methyl-3-[7-(4-methylsulfanyl-phenyl)-2,3,
6,7-tetrahydro-[1,4]thiazepin-5-yl]-pyran-2-one;

3-[7-(3,4-dichloro-phenyl)-2,3,6,7-tetrahydro-[1,4]
thiazepin-5-yl]-4-hydroxy-6-methyl-pyran-2-one;

6-methyl-3-[7-(2,3,4-trimethoxy-phenyl)-2,3,6,7-
tetrahydro-[1,4]thiazepin-5-yl]-pyran-2-one;

4-hydroxy-3-[7-(4-chloro-2-methoxy-phenyl)-2,3,6,7-
tetrahydro-[1,4]thiazepin-5-yl]-6-methylpyran-2-one;
and 4-hydroxy-3-[7-(2,4-dimethoxy-phenyl)-2,3,6,7-
tetrahydro-[1,4]thiazepin-5-yl]-6-methyl-pyran-2-one.

Chemistry

Processes for Making Compounds of the Invention

Compounds of the invention may be prepared by pro-
ceeding as in Scheme 1.

Scheme 1

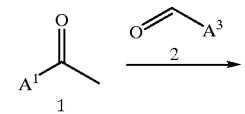

-continued

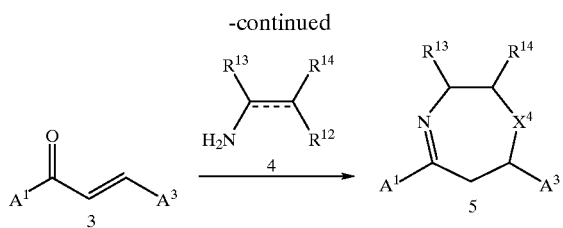

in which the dashed line indicates optional unsaturation, $X^4$ is —$NR^2$ or SH, $R^{12}$ is —$NHR^2$ or —SH, $R^{13}$ and $R^{14}$ independently are hydrogen or any of the optional substituents defined for $A^2$ in the Summary of the Invention or $R^{13}$ and $R^{14}$ together with the atoms to which $R^{13}$ and $R^{14}$ are attached form a monocyclic or fused polycyclic ring system selected from aryl containing a total of 6 to 9 ring atoms, heteroaryl containing a total of 5 to 9 ring atoms and unsaturated, partially unsaturated or saturated carbocycloalkyl or heterocycloalkyl each containing a total of 3 to 9 ring atoms and the compound of Formula 4 may be optionally substituted.

Compounds of the invention may be prepared by reacting a compound of Formula 3 with a compound of Formula 4. The reaction is carried out in a suitable solvent (e.g., ethanol) at between 60 and 80° C. and requires 10 minutes to 20 hours to complete. A detailed description for the preparation of a compound of Formula I by the methods described above is set forth in Example 2, infra.

Compounds of Formula 3 can be prepared by reacting a ketone of Formula I with an aldehyde of Formula 2. The reaction is carried out in an appropriate solvent (e.g., ethanol) and in the presence of a suitable base (e.g., piperidine) at between 80 to 85° C. and requires 8 to 24 hours to complete. A detailed description for the preparation of a compound of Formula I by the methods described above is set forth in Reference 5.1, infra.

Compounds of Formula I in which $A^2$ is [1,4] thiazepanylene wherein $R^1$ is —$C(O)R^6$ can be prepared by reducing a compound of Formula I in which $A^2$ is 2,3,6,7-tetrahydro-[1,4]thiazepinylene to the corresponding thiazepane and then condensing the thiazepane with an anhydride of the Formula $O[C(O)R^6]_2$. The reduction is carried out in a suitable solvent (e.g., ethanol) and in the presence of a suitable reducing agent (e.g., sodium borohydride) at 35 and 50° C. and requires 0.5 to 6 hours to complete. The condensation reaction is carried out in the presence of suitable base (e.g., diisopropylethylamine (DIPEA)) and requires 0.5 to 14 hours to complete. A detailed description for the preparation of a compound of Formula I by the methods described above is set forth in Example 1, infra.

Compounds of Formula I in which $A^2$ is 1-oxo-2,3,6,7-tetrahydro-1H-1H1$\lambda^4$-[1,4]thiazepinylene can be prepared by oxidizing a compound of Formula I in which $A^2$ is 2,3,6,7-tetrahydro-[1,4]thiazepinylene. The oxidation is carried out in a suitable solvent (e.g., acetic acid) and in the presence of a suitable oxidizing agent (e.g., hydrogen peroxide) at ambient temperature and requires 2 to 3 hours to complete. Compounds of Formula I in which $A^2$ is 1,1-dioxo-2,3,6,7-tetrahydro-1H-1$\lambda^4$-[1,4]thiazepinylene can be prepared by proceeding as described above, but heating the reaction at approximately 70° C. for 2 to 3 hours. Detailed descriptions for the preparation of a compound of Formula I by the methods described above are set forth in Examples 3 and 5, infra.

Compounds of Formula I in which $A^2$ is [1,4] thiazepanylene wherein $R^1$ and $A^1$ and the atoms to which $A^1$ and $R^1$ are attached together with $A^2$ form a group of Formula (h) can be prepared by reacting a corresponding compound of Formula I in which $A^2$ is 2,3,6,7-tetrahydro-[1,4]thiazepinylene and $A^1$ is 4-hydroxy-6-methyl-2-oxo-2H-pyran-3-yl with phosgene. The reaction is carried out in a suitable solvent (e.g., ethylene dichloride) and in the presence of a suitable acylation catalyst (e.g., 4-(dimethylamino)pyridine) and in the presence of suitable base (e.g., DIPEA) at ambient temperature and requires 0.5 to 1 hours to complete. A detailed description for the preparation of a compound of Formula I by the methods described above is set forth in Example 4, infra.

Compounds of Formula I in which $A^2$ is 2,3-dihydro-[1,4]thiazepinylene can be prepared by dehydrogenation of a corresponding compound of Formula I in which $A^2$ is 2,3,6,7-tetrahydro-[1,4]thiazepinylene. The reaction is carried out in a appropriate solvent (e.g., toluene) and in the presence of a suitable catalyst (e.g., 2,3-dichloro-5,6-dicyano-1,4-benzoquinone) at 60 to 80° C. and requires 20 to 30 minutes to complete. A detailed description for the preparation of a compound of Formula I by the methods described above is set forth in Example 5, infra.

EXPERIMENTALS

Reference 1

3-Acetyl-4-hydroxy-6-methyl-5,6-dihydro-pyran-2-one

4-Hydroxy-6-methyl-5,6-dihydro-pyran-2-one (2 g, 15.6 mmol) was combined with methylene chloride (50 mL) in a 250 mL flask and then acetic acid (17.5 M, 2 eq, 31 mmol, 1.77 mL) was added to the mixture. The mixture was cooled in an ice bath and then dicyclohexylcarbodiimide (1.3 eq, 20.3 mmol, 4.19 g) was added portionwise, followed by the addition of 4-(dimethylamino)pyridine (0.05 eq, 0.78 mmol, 88 mg) to the mixture. A sufficient amount of methylene chloride was added to ensure easy stirring and the reaction was monitored by TLC (silica gel, hexane-ethyl acetate-methylene chloride-acetone (3:3:3:1 v/v)), HPLC and LCMS as the intermediate acetic acid 2-methyl-6-oxo-3,6-dihydro-2H-pyran-4-yl ester was formed. The mixture was stirred overnight at room temperature and then toluene (20 ml) was added. The mixture was heated to 60° C. and after 48 hours the mixture was filtered, concentrated and purified by flash column chromatography to provide 3-acetyl-4-hydroxy-6-methyl-5,6-dihydro-pyran-2-one (1.02 g, 38%) as a white solid, mp 96–98° C. (lit., mp 97–98° C.). LCMS: $MH^+$ 171.0.

Reference 2

2-Acetyl-3-hydroxy-cyclohex-2-enone

3-Hydroxy-cyclohex-2-enone (1.08 g, 9.64 mmol) was combined with methylene chloride (10 mL) in a 250 mL flask and acetic acid (1.4 eq, 13.75 mmol, 0.78 mL) was added to the mixture. The mixture was cooled in an ice bath and dicyclohexylcarbodiimide (1.3 eq, 12 mmol, 2.5 g) was added portionwise, followed by the addition of 4-(dimethylamino)pyridine (0.05 eq, 0.45 mmol, 50 mg). A sufficient amount of methylene chloride was added to ensure easy stirring and the reaction was monitored by TLC (silica gel, hexane-ethyl acetate-methylene chloride-acetone (3:3:3:1 v/v)), HPLC and LCMS and the intermediate acetic acid 3-oxo-cyclohex-1-enyl ester was formed. The mixture was stirred overnight at room temperature and then toluene (20 mL) was added. The mixture heated to 60° C. and after 72 hours the mixture was filtered, concentrated and purified by flash column chromatography to provide 2-acetyl-3-hydroxy-cyclohex-2-enone (1.19 g, 80%) as a colorless liquid. LCMS: MH$^+$ 154.8.

Reference 3

3-Acetyl-4-hydroxy-1H-quinolin-2-one

A solution of 2-amino-benzoic acid methyl ester (1.51 g, 10 mmol) and triethylamine (97.2 mmol/ml, 0.0194 mL, 0.14 mmol, 0.014 eq) in toluene (4 mL) was heated to 60° C. and then a solution of 4-methylene-oxetan-2-one (0.84 g, 10 mmol) in toluene (2 ml) was added to the solution over 15 minutes. The reaction was heated at 80° C. for 6 hours and then at 50° C. for 16 hours. Progress of the reaction was monitored by TLC (silica gel, hexane-ethyl acetate (7:3 v/v)), analytical HPLC and LCMS and upon its completion the mixture was partitioned between ethyl acetate and aqueous hydrochloric acid (1 N). The organic layer was washed with water, saturated sodium bicarbonate, water and then brine, dried over Na$_2$SO$_4$ and concentrated to give an orange solid. The solid was crystalized from methylene chloride/ethyl acetate and hexane to provide 2-(3-oxo-butanoylamino)-benzoic acid methyl ester (1.83 g, 78%) as large colorless prisms, mp 81–83° C. (lit., mp 79–80° C.). LCMS MH$^+$ 235.6.

2-(3-Oxo-butanoylamino)-benzoic acid methyl ester (383 mg, 1.63 mmol) was combined with diethyl ether (10 mL) and methanol (5 mL) and the mixture was stirred rapidly while a solution of sodium methoxide (25% solution, 1.63 mmol, 0.45 mL) in methanol (3 mL) was added over 10 minutes. The reaction then was heated at 40° C. overnight. Progress of the reaction was monitored by TLC (silica gel, hexane:EtOAc:CH$_2$Cl$_2$:acetone (3:3:3:1)) and analytical HPLC and upon its completion the mixture was acidified with 1 N sulfuric acid to form a solid. The solid was collected by filtration and then crystallized from hot acetic acid/acetonitrile/water to provide 3-acetyl-4-hydroxy-1H-quinolin-2-one (250 mg, 76%) as small colorless prisms, mp 258–262° C. (dec) (lit., 259° C.). LCMS MH$^+$ 204.2.

Reference 4

2-Methoxy4-methylsulfanyl-benzaldehyde

2-Methoxy-4-methylsulfanyl-benzoic acid (2 g, 10.09 mmol) was dissolved in dry THF (20 mL) and the solution was stirred while heated to 60° C. under nitrogen and then borane-methylsulfide complex (1.7 eq, 1.7 mL, 17.5 mmol) was added very slowly dropwise via a syringe. The progress of the reaction was followed by both TLC and analytical HPLC and when complete (3 hours) the mixture was allowed to cool to room temperature, diluted with water (10 mL) added extremely slowly dropwise under nitrogen. Potassium carbonate (1 g) was added and after stirring the mixture for 30 minutes ethyl acetate (50 ml) was added. The organic layer was separated, washed with water, 2 N hydrochloric acid, water and brine, dried over Na$_2$SO$_4$ and then concentrated to a near colorless oil. The residue was triturated with hexane and product was purified from the resulting crystals by flash column chromatography to provide (2-methoxy-4-methylsulfanyl-phenyl)-methanol (934 mg, 51%) as colorless crystals. LCMS: M$^-$182.8.

Pyridine (4.8 mL, 60 mmol, 12 eq) was added under nitrogen to a mixture of chromium trioxide (fresh, 2 g, 20 mmol) in dry methylene chloride (15 mL) cooled over an ice bath. The mixture was stirred at 0° C. for 1 hour and Celite powder (1 g) and a solution of (2-methoxy-4-methylsulfanyl-phenyl)-methanol (934 mg, 5.07 mmol) in methylene chloride (10 mL) was added. The progress of the reaction was followed by TLC (silica gel, hexane-EtOAc-CH$_2$Cl$_2$-acetone (3:3:3:1 v/v) and hexane-ethyl acetate (7:3 v/v)) and analytical HPLC and when complete, the mixture was applied to a silica gel column (made up in hexane) and the column eluted with methylene chloride. Pure fractions were combined and concentrated to provide 2-methoxy-4-methylsulfanyl-benzaldehyde (730 mg, 79%). LCMS: MH$^+$ 183.2.

Reference 5

3-[7-(2,4-Dimethoxyphenyl)-2,3,6,7-tetrahydro-[1,4] thiazepin-5-yl]-4-hydroxy-6-methyl-pyran-2-one Step 5.1

3-Acetyl-4-hydroxy-6-methyl-pyran-2-one (5.07 g, 30.15 mmol) and 2,4-dimethoxybenzaldehyde (5.03 g, 30.27 mmol) were combined in a 250 mL round bottom flask. Absolute ethanol (20 mL) and piperidine (0.10 eq, 0.30 mL, 3.0 mmol) were added and the mixture heated to between 80 and 85 ° C. The reaction was monitored by TLC (silica gel, hexane-ethyl acetate (1:1 v/v) and methylene chloride-ethyl acetate-acetone (5:5:1 v/v)) and analytical HPLC. After 20 hours (>95% completion) the reaction mixture was cooled to room temperature to provide 3-[3-(2,4-dimethoxy-phenyl)-acryloyl]-4-hydroxy-6-methyl-pyran-2-one as a bright orange crystalline precipitate. MS M$^+$317. NMR (CDCl$_3$-TMS): d 8.31 (m, 2H), 7.69 (d, 1H, J=9 Hz), 6.54 (d, 1H, J=9 Hz), 6.45 (s, 1H), 5.93 (s, 1H), 3.91 (s, 3H), 3.87 (s, 3H), 2.26 (s, 3H) NMR (DMSO-d$_6$): d 8.11 (s, 2H), 7.62 (d, 1H, J=9 Hz), 6.63 (bs, 2H), 6.23 (s, 1H), 3.87 (s, 3H), 3.82 (s, 3H), 2.28 (s, 3H).

Step 5.2

The crude reaction mixture prepared in Step 5.1 was diluted with absolute ethanol (5 mL). 2-Aminoethanethiol (2.31 g, 30 mmol fresh dry material) was added and the mixture heated to 75° C. The reaction was monitored by TLC (silica gel, hexane-ethyl acetate (1:1 v/v) and methylene chloride-ethyl acetate-acetone (5:5:1 v/v)) and analytical HPLC. After 1.5 hours (>90% completion) the reaction was allowed to cool to room temperature to form a yellow crystalline solid. The solid material was collected by filtration and washed with ethanol-diethyl ether (1:1 v/v) and then hexane. Product was purified by column chromatography and then crystallization (methylene chloride-ethanol) to provide 3-[7-(2,4-dimethoxyphenyl)-2,3,6,7-tetrahydro-[1,4]thiazepin-5-yl]-4-hydroxy-6-methyl-pyran-2-one (6.81 g, 61%). LCMS: MH$^+$375.6. Elemental Analysis: Calc: C 60.78, H 5.64, N 3.73 Found: 60.73, H 5.66, N 3.73. $^1$H NMR (CDCl$_3$-TMS): d 14.3 (bs, 1H), 7.23 (m, 1H), 6.46 (m, 2H), 5.69 (s, 1H), 4.76 (d, 1H, J=13 Hz), 4.47 (d, 1H, J=11 Hz), 4.17 (m, 1H), 4.00 (m, 1H), 3.83 (s, 3H), 3.79 (s, 3H), 3.52 (t, 1H, J=11.5 Hz), 3.00 (t, 1H, J=11.5 Hz), 2.78 (dd, 1H, J=11.5,5 Hz), 2.09 (s, 3H). $^1$H NMR (DMSO-d$_6$): d 13.7 (bs, 1H), 7.23 (dd, 1H, J=9, 3 Hz), 6.5 (m, 2H), 5.7 (s, 1H), 4.37 (d, 1H, J=13 Hz), 4.28 (d, 1H, J=10 Hz), 4.08 (m, 2H), 3.73 (s, 6H), 3.61 (t, 1H, J=11 Hz), 2.79 (m, 2H), 2.03 (s, 3H). $^{13}$C NMR JEOL, (DMSO-d$_6$): d 183.84, 178.36, 163.42, 162.89, 160.32, 157.33, 128.28, 123.29, 107.76, 105.46, 99.16, 95.78, 56.26, 55.77, 46.0, 38.90, 34.19, 29.07, 19.68.

Proceeding as in Reference 5, Step 5.1, but substituting 3-acetyl-4-hydroxy-6-methyl-5,6-dihydro-pyran-2-one for 3-acetyl-4-hydroxy-6-methyl-pyran-2-one, provided 3-[(E)-3-(2,4-dimethoxy-phenyl)-acryloyl]-4-hydroxy-6-methyl-5,6-dihydro-pyran-2-one.

Proceeding as in Reference 5, Step 5.1, but substituting 2-acetyl-3-hydroxy-cyclohex-2-enone for 3-acetyl-4-hydroxy-6-methyl-pyran-2-one, provided 2-[3-(2,4-dimethoxy-phenyl)-acryloyl]-3-hydroxy-cyclohex-2-enone.

Proceeding as in Reference 5, Step 5.1, but substituting 3-acetyl-4-hydroxy-1H-quinolin-2-one for 3-acetyl-4-hydroxy-6-methyl-pyran-2-one, provided 3-[(E)-3-(2,4-dimethoxy-phenyl)-acryloyl]-4-hydroxy-1H-quinolin-2-one.

Proceeding as in Reference 5, Step 5.1, but substituting 2-methoxy-4-methylsulfanyl-benzaldehyde for 2,4-dimethoxybenzaldehyde, provided 4-hydroxy-3-[(E)-3-(2-methoxy-4-methylsulfanyl-phenyl)-acryloyl]-6-methyl-pyran-2-one.

Proceeding as in Reference 5, Step 5.1, but substituting 3-phenyl-1H-pyrazole-4-carbaldehyde for 2,4-dimethoxybenzaldehyde, provided 4-hydroxy-6-methyl-3-[(E)-3-(3-phenyl-1H-pyrazol-4-yl)-acryloyl]-pyran-2-one.

Proceeding as in Reference 5, Step 5.1, but substituting 3-acetyl-4-methoxy-6-methyl-pyran-2-one for 3-acetyl-4-hydroxy-6-methyl-pyran-2-one, provided 3-[(E)-3-(2,4-dimethoxy-phenyl)-acryloyl]4-methoxy-6-methyl-pyran-2-one.

Proceeding as in Reference 5, Step 5.1, but substituting 5-ethylthiene-2-carbaldehyde for 2,4-dimethoxybenzaldehyde, provided 3-[(E)-3-(5-ethyl-thien-2-yl)-acryloyl]-4-hydroxy-6-methyl-pyran-2-one.

Proceeding as in Reference 5, Step 5.1, but substituting 1-benzyl-1H-indole-3-carbaldehyde for 2,4-dimethoxybenzaldehyde, provided 3-[(E)-3-(1-benzyl-1H-indol-3-yl)acryloyl]-4-hydroxy-6-methyl-pyran-2-one.

Proceeding as in Reference 5, Step 5.1, but substituting 2-trifluormethylsulfanyl-benzaldehyde for 2,4-dimethoxybenzaldehyde, provided 4-hydroxy-6-methyl-3-[(E)-3-(2-trifluoromethylsulfanyl-phenyl)-acryloyl]-pyran-2-one.

Proceeding as in Reference 5, Step 5.1, but substituting 3-trifluoromethylsulfanyl-benzaldehyde for 2,4-dimethoxybenzaldehyde, provided 4-hydroxy-6-methyl-3-[(E)-3-(3-trifluoromethylsulfanyl-phenyl)-acryloyl]-pyran-2-one.

Proceeding as in Reference 5, Step 5.1, but substituting 4-trifluoromethylsulfanyl-benzaldehyde for 2,4-dimethoxybenzaldehyde, provided 4-hydroxy-6-methyl-3-[(E)-3-(4-trifluoromethylsulfanyl-phenyl)-acryloyl]-pyran-2-one.

Proceeding as in Reference 5, Step 5.1, but substituting 3-(3-trifluoromethyl-phenoxy)-benzaldehyde for 2,4-dimethoxybenzaldehyde, provided 4-hydroxy-6-methyl-3-{(E)-3-[3-(3-trifluoromethyl-phenoxy)-phenyl]-acryloyl}-pyran-2-one.

Proceeding as in Reference 5, Step 5.1, but substituting 3-(3,4-dichloro-phenoxy)-benzaldehyde for 2,4-dimethoxybenzaldehyde, provided 3-{(E)-3-[3-(3,4-dichloro-phenoxy)-phenyl]-acryloyl}-4-hydroxy-6-methyl-pyran-2-one.

Proceeding as in Reference 5, Step 5.1, but substituting 3-(3,5-dichloro-phenoxy)-benzaldehyde for 2,4-dimethoxybenzaldehyde, provided 3-{(E)-3-[3-(3,5-dichloro-phenoxy)-phenyl]-acryloyl}-4-hydroxy-6-methyl-pyran-2-one.

Proceeding as in Reference 5, Step 5.1, but substituting 5-(3-trifluoromethyl-phenyl)-furan-2-carbaldehyde for 2,4-dimethoxybenzaldehyde, provided 4-hydroxy-6-methyl-3-{(E)-3-[5-(3-trifluoromethyl-phenyl)-furan-2-yl]-acryloyl}-pyran-2-one.

Proceeding as in Reference 5, Step 5.1, but substituting 5-(2-chloro-phenyl)-furan-2-carbaldehyde for 2,4-dimethoxybenzaldehyde, provided 3-{(E)-3-[5-(2-chloro-phenyl)-furan-2-yl]-acryloyl}-4-hydroxy-6-methyl-pyran-2-one.

Proceeding as in Reference 5, Step 5.1, but 5-(3-chloro-phenyl)-furan-2-carbaldehyde substituting for 2,4-dimethoxybenzaldehyde, provided 3-{(E)-3-[5-(3-chloro-phenyl)-furan-2-yl]-acryloyl }-4-hydroxy-6-methyl-pyran-2-one.

Proceeding as in Reference 5, Step 5.1, but substituting 5-(4-chloro-phenyl)-furan-2-carbaldehyde for 2,4-dimethoxybenzaldehyde, provided 3-{(E)-3-[5-(4-chloro-phenyl)-furan-2-yl]-acryloyl}-4-hydroxy-6-methyl-pyran-2-one.

Proceeding as in Reference 5, Step 5.1, but substituting 5-(chloro-trifluoromethyl-phenyl)-furan-2-carbaldehyde for 2,4-dimethoxybenzaldehyde, provided 3-{(E)-3-[5-(chloro-trifluoromethyl-phenyl)-furan-2-yl]-acryloyl}-4-hydroxy-6-methyl-pyran-2-one.

Proceeding as in Reference 5, Step 5.1, but substituting 4-bromo-thiene-2-carbaldehyde for 2,4-dimethoxybenzaldehyde, provided 3-[(E)-3-(4-bromo-thien-2-yl)-acryloyl]-4-hydroxy-6-methyl-pyran-2-one.

Proceeding as in Reference 5, Step 5.1, but substituting 5-bromo-thiene-2-carbaldehyde for 2,4-dimethoxybenzaldehyde, provided 3-[(E)-3-(5-bromo-thien-2-yl)-acryloyl]-4-hydroxy-6-methyl-pyran-2-one.

Proceeding as in Reference 5, Step 5.1, but 1-benzenesulfonyl-1H-pyrrole-2-carbaldehyde substituting for 2,4-dimethoxybenzaldehyde, provided 3-[(E)-3-(1-benzenesulfonyl-1H-pyrrol-2-yl)-acryloyl]-4-hydroxy-6-methy-pyran-2-one.

Proceeding as in Reference 5, Step 5.1, but substituting 3-methyl-thiene-2-carbaldehyde for 2,4-dimethoxybenzaldehyde, provided 4-hydroxy-6-methyl-3-[(E)-3-(3-methyl-thien-2-yl)-acryloyl]-pyran-2-one.

Proceeding as in Reference 5, Step 5.1, but substituting 5-methyl-thiene-2-carbaldehyde for 2,4-dimethoxybenzaldehyde, provided 4-hydroxy-6-methyl-3-[(E)-3-(5-methyl-thien-2-yl)-acryloyl]-pyran-2-one.

Proceeding as in Reference 5, Step 5.1, but substituting 1-methyl-1H-indole-3-carbaldehyde for 2,4-dimethoxybenzaldehyde, provided 4-hydroxy-6-methyl-3-[(E)-3-(1-methyl-1H-indol-3-yl)-acryloyl]-pyran-2-one.

Proceeding as in Reference 5, Step 5.1, but substituting chloro-methyl-trifluoromethyl-1H-pyrazole-4-carbaldehyde for 2,4-dimethoxybenzaldehyde, provided 3-[(E)-3-(chloro-methyl-trifluoromethyl-1H-pyrazol-4-yl)-acryloyl]-4-hydroxy-6-methyl-pyran-2-one.

Proceeding as in Reference 5, Step 5.1, but substituting 1-(2,4-difluoro-benzenesulfonyl)-1H-pyrrole-2-carbaldehyde for 2,4-dimethoxybenzaldehyde, provided 3-{(E)-3-[1-(2,4-difluoro-benzenesulfonyl)-1H-pyrrol-2-yl]-acryloyl}-4-hydroxy-6-methyl-pyran-2-one.

Proceeding as in Reference 5, Step 5.1, but substituting [2,2']bithienyl-5-carbaldehyde for 2,4-dimethoxybenzaldehyde, provided 3-((E)-3-[2,2']bithienyl-5-yl-acryloyl)-4-hydroxy-6-methyl-pyran-2-one.

Proceeding as in Reference 5, Step 5.1, but substituting 1-(3,5-dichloro-phenyl)-1H-pyrrole-2-carbaldehyde for 2,4-dimethoxybenzaldehyde, provided 3-{(E)-3-[1-(3,5-dichloro-phenyl)-1H-pyrrol-2-yl]-acryloyl}-4-hydroxy-6-methyl-pyran-2-one.

Proceeding as in Reference 5, Step 5.1, but substituting 1-(4-chloro-phenyl)-1H-pyrrole-2-carbaldehyde for 2,4-dimethoxybenzaldehyde, provided 3-{(E)-3-[1-(4-chloro-phenyl)-1H-pyrrol-2-yl]-acryloyl}-4-hydroxy-6-methy-pyran-2-one.

Proceeding as in Reference 5, Step 5.1, but substituting 5-chloro-1H-indole-3-carbaldehyde for 2,4-dimethoxybenzaldehyde, provided 3-[(E)-3-(5-chloro-1H-indol-3-yl)-acryloyl]-4-hydroxy-6-methyl-pyran-2-one.

Proceeding as in Reference 5, Step 5.1, but substituting 6-p-tolylsulfanyl-imidazo[2,1-b]thiazole-5-carbaldehyde for 2,4-dimethoxybenzaldehyde, provided 4-hydroxy-6-methyl-3-[(E)-3-(6-p-tolylsulfanyl-imidazo[2,1-b]thiazol-5-yl)-acryloyl]-pyran-2-one.

Proceeding as in Reference 5, Step 5.1, but substituting 4,5-dibromo-thiene-2-carbaldehyde for 2,4-dimethoxybenzaldehyde, provided 3-[(E)-3-(4,5-dibromo-thien-2-yl)-acryloyl]-4-hydroxy-6-methyl-pyran-2-one.

Proceeding as in Reference 5, Step 5.1, but substituting chloro-trifluoromethyl-benzaldehyde for 2,4-dimethoxybenzaldehyde, provided 3-[(E)-3-(chloro-trifluoromethyl-phenyl)-acryloyl]-4-hydroxy-6-methyl-pyran-2-one.

Proceeding as in Reference 5, Step 5.1, but substituting 3-acetyl-4-hydroxy-6-methyl-5,6-dihydro-pyran-2-one for 3-acetyl-4-hydroxy-6-methyl-pyran-2-one, provided 3-[(E)-3-(2,4-dimethoxy-phenyl)-acryloyl]-4-hydroxy-6-methyl-5,6-dihydro-pyran-2-one.

Proceeding as in Reference 5, Step 5.1, but substituting 5-methylsulfanyl-thiene-2-carbaldehyde for 2,4-dimethoxybenzaldehyde, provided 4-hydroxy-6-methyl-3-[(E)-3-(5-methylsulfanyl-thien-2-yl)-acryloyl]-pyran-2-one.

Proceeding as in Reference 5, Step 5.1, but substituting 5-chloro-1-methyl-3-phenyl-1H-pyrazole-4-carbaldehyde for 2,4-dimethoxybenzaldehyde, provided 3-[(E)-3-(5-chloro-1-methyl-3-phenyl-1H-pyrazol-4-yl)-acryloyl]-4-hydroxy-6-methyl-pyran-2-one.

Proceeding as in Reference 5, Step 5.1, but substituting 2-acetyl-3-hydroxy-cyclohex-2-enone for 3-acetyl-4-hydroxy-6-methyl-pyran-2-one, provided 2-[3-(2,4-dimethoxy-phenyl)-acryloyl]-3-hydroxy-cyclohex-2-enone.

Proceeding as in Reference 5, Step 5.1, but substituting 1-(3-fluoro-4-methoxy-phenyl)-ethanone for 3-acetyl-4-hydroxy-6-methyl-pyran-2-one, provided (E)-1-(3-fluoro-4-methoxy-phenyl)-3-(2-hydroxy-4-methoxy-phenyl)-propenone.

Proceeding as in Reference 5, Step 5.1, but substituting 4-dimethylamino-benzaldehyde for 2,4-dimethoxybenzaldehyde, provided 3-[(E)-3-(4-dimethylamino-phenyl)-acryloyl]-4-hydroxy-6-methyl-pyran-2-one.

Proceeding as in Reference 5, Step 5.1, but substituting 3-acetyl-4-hydroxy-1H-quinolin-2-one for 3-acetyl-4-hydroxy-6-methyl-pyran-2-one, provided 3-[(E)-3-(2,4-dimethoxy-phenyl)-acryloyl]-4-hydroxy-1H-quinolin-2-one.

Proceeding as in Reference 5, Step 5.1, but substituting 4-trifluoromethoxy-benzaldehyde for 2,4-dimethoxybenzaldehyde, provided 4-hydroxy-6-methyl-3-[(E)-3-(4-trifluoromethoxy-phenyl)-acryloyl]-pyran-2-one.

Proceeding as in Reference 5, Step 5.1, but substituting bis-trifluoromethyl-benzaldehyde for 2,4-dimethoxybenzaldehyde, provided 3-[(E)-3-(bis-trifluoromethyl-phenyl)-acryloyl]-4-hydroxy-6-methyl-pyran-2-one.

Proceeding as in Reference 5, Step 5.1, but substituting 4-dimethylamino-2-methoxy-benzaldehyde for 2,4-dimethoxybenzaldehyde, provided 3-[(E)-3-(4-dimethylamino-2-methoxy-phenyl)-acryloyl]-4-hydroxy-6-methyl-pyran-2-one.

Proceeding as in Reference 5, Step 5.1, but substituting 4-methanesulfonyl-benzaldehyde for 2,4-dimethoxybenzaldehyde, provided 4-hydroxy-3-[(E)-3-(4-methanesulfonyl-phenyl)-acryloyl]-6-methyl-pyran-2-one.

Proceeding as in Reference 5, Step 5.1, but substituting 2,4-diethoxy-benzaldehyde for 2,4-dimethoxybenzaldehyde, provided 3-[(E)-3-(2,4-diethoxy-phenyl)-acryloyl]-4-hydroxy-6-methyl-pyran-2-one.

Proceeding as in Reference 5, Step 5.1, but substituting 2,4-diethoxy-benzaldehyde for 2,4-dimethoxybenzaldehyde and 3-acetyl-4-hydroxy-6-methyl-5,6-dihydro-pyran-2-one for 3-acetyl-4-hydroxy-6-methyl-pyran-2-one, provided 3-[(E)-3-(2,4-diethoxy-phenyl)-acryloyl]-4-hydroxy-6-methyl-5,6-dihydro-pyran-2-one.

Proceeding as in Reference 5, Step 5.1, but substituting 4-dimethylamino-benzaldehyde for 2,4-dimethoxybenzaldehyde and 3-acetyl-4-hydroxy-6-methyl-5,6-dihydro-pyran-2-one for 3-acetyl-4-hydroxy-6-methyl-pyran-2-one, provided 3-[(E)-3-(4-dimethylamino-phenyl)-acryloyl]-4-hydroxy-6-methyl-5,6-dihydro-pyran-2-one.

Proceeding as in Reference 5, Step 5.1, but substituting 2,4-diethoxy-benzaldehyde for 2,4-dimethoxybenzaldehyde and 2-acetyl-3-hydroxy-cyclohex-2-enone for 3-acetyl-4-hydroxy-6-methyl-pyran-2-one, provided 2-[(E)-3-(2,4-diethoxy-phenyl)-acryloyl]-3-hydroxy-cyclohex-2-enone.

Proceeding as in Reference 5, Step 5.1, but substituting 2,4-diethoxy-benzaldehyde for 2,4-dimethoxybenzaldehyde and 2-acetyl-3-hydroxy-cyclohex-2-enone for 3-acetyl-4-hydroxy-6-methyl-pyran-2-one, provided 2-[(E)-3-(2,4-diethoxy-phenyl)-acryloyl]-3-hydroxy-cyclohex-2-enone.

Proceeding as in Reference 5, Step 5.1, but substituting 2,3,4-trimethoxy-benzaldehyde for 2,4-dimethoxybenzaldehyde and 2-acetyl-3-hydroxy-cyclohex-2-enone for 3-acetyl-4-hydroxy-6-methyl-pyran-2-one, provided 3-hydroxy-2-[(E)-3-(2,3,4-trimethoxy-phenyl)-acryloyl]-cyclohex-2-enone.

Proceeding as in Reference 5, Step 5.1, but substituting 2-methoxy-4-methylsulfanyl-benzaldehyde for 2,4-dimethoxybenzaldehyde, provided 4-hydroxy-3-[(E)-3-(2-methoxy-4-methylsulfanyl-phenyl)-acryloyl]-6-methyl-pyran-2-one.

Proceeding as in Reference 5, Step 5.1, but substituting 2,3,4-timethoxy-benzaldehyde for 2,4-dimethoxybenzaldehyde and 3-acetyl-4-hydroxy-6-methyl-5,6-dihydro-pyran-2-one for 3-acetyl-4-hydroxy-6-methyl-pyran-2-one, provided 4-hydroxy-6-methyl-3-[(E)-3-(2,3,4-trimethoxy-phenyl)-acryloyl]-5,6-dihydro-pyran-2-one.

Example 1

3-[4-Acetyl-7-(2,4-dimethoxy-phenyl)-[1,4]thiazepan-5-yl]-4-hydroxy-6-methyl-pyran-2-one Compound 1

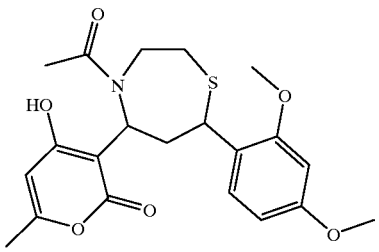

3-[7-(2,4-Dimethoxyphenyl)-2,3,6,7-tetrahydro-[1,4]thiazepin-5-yl]-4-hydroxy-6-methyl-pyran-2-one (187 mg, 0.5 mmol), prepared as in Reference 5, was combined with absolute ethanol (5 mL) and sodium borohydride (20 mg, 0.526 mmol) and the mixture was warmed on a hot plate to form a solution. The progress of the reaction was followed by analytical HPLC and LCMS and when complete (5 hours) acetic anhydride (1.5 ml. 30 eq) and DIPEA (0.6 mmol, 0.1 mL) were added. The reaction was stirred at room temperature overnight. Product was isolated by preparative HPLC (RPC$_{18}$ column, acetonitrile/water containing 0.1% HCl) to provide 3-[4-acetyl-7-(2,4-dimethoxy-phenyl)-[1,4]thiazepan-5-yl]-4-hydroxy-6-methyl-pyran-2-one (25 mg). LCMS: MH$^+$ 420.2.

Proceeding as in Example 1, but substituting trifluoroacetic anhydride for acetic anhydride, provided 3-[7-(2,4-dimethoxy-phenyl)-4-(2,2,2-trifluoro-ethanoyl)-[1,4]thiazepan-5-yl]-4-hydroxy-6-methyl-pyran-2-one (Compound 2); LCMS: MH$^+$ 474.0.

Proceeding as in Example 1, but substituting 7-(2,4-dimethoxy-phenyl)-5-(3-fluoro-4-methoxy-phenyl)-2,3,6,7-tetrahydro-[1,4]thiazepine for 3-[7-(2,4-dimethoxyphenyl)-2,3,6,7-tetrahydro-[1,4]thiazepin-5-yl]-4-hydroxy-6-methyl-pyran-2-one, provided 1-[7-(2,4-dimethoxy-phenyl)-5-(3-fluoro-4-methoxy-phenyl)-[1,4]thiazepan4-yl]-ethanone (Compound 3); LCMS: MH$^+$ 420.2.

Example 2

4-Hydroxy-3-[7-(2-methoxy-4-methylsulfanyl-phenyl)-2,3,6,7-tetrahydro-[1,4]thiazepin-5-yl]-6-methyl-pyran-2-one Compound 4

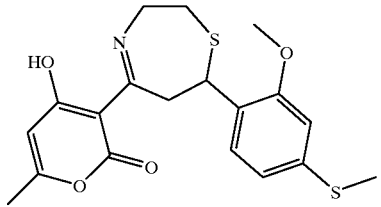

4-Hydroxy-3-[(E)-3-(2-methoxy-4-methylsulfanyl-phenyl)-acryloyl]-6-methyl-pyran-2-one (41.8 mg, 0.126 mmol), prepared as in Reference 5, Step 5.1, was dissolved in absolute ethanol (5 mL) and then 2-aminoethanethiol (9.8 mg, 0.126 mmol) was added to the solution. The mixture was stirred at 80° C. The progress of the reaction was followed by analytical HPLC and when complete (approximately 12 hours) the solvent was removed in vacuo. Product was purified by silica flash column chromatography to provide 4-hydroxy-3-[7-(2-methoxy-4-methylsulfanyl-phenyl)-2,3,6,7-tetrahydro-[1,4]thiazepin-5-yl]-6-methyl-pyran-2-one (20.5 mg) as a pale, yellow solid. LCMS: MH$^+$ 392.6.

Proceeding as in Example 2, but substituting 4-hydroxy-6-methyl-3-[(E)-3-(3-phenyl-1H-pyrazol-4-yl)-acryloyl]-pyran-2-one for 4-hydroxy-3-[(E)-3-(2-methoxy-4-methylsulfanyl-phenyl)-acryloyl]-6-methyl-pyran-2-one, provided 4-hydroxy-6-methyl-3-[7-(3-phenyl-1H-pyrazol-4-yl)-2,3,6,7-tetrahydro-[1,4]thiazepin-5-yl]-pyran-2-one (Compound 5); LCMS: MH$^+$ 383.

Proceeding as in Example 2, but substituting 3-[(E)-3-(2,4-dimethoxy-phenyl)-acryloyl]-4-methoxy-6-methyl-pyran-2-one for 4-hydroxy-3-[(E)-3-(2-methoxy-4-methylsulfanyl-phenyl)-acryloyl]-6-methyl-pyran-2-one, provided 3-[7-(2,4-dimethoxy-phenyl)-2,3,6,7-tetrahydro-[1,4]thiazepin-5-yl]4-methoxy-6-methyl-pyran-2-one (Compound 6); MS MH$^+$ 390.

Proceeding as in Example 2, but substituting 3-[(E)-3-(5-ethyl-thien-2-yl)-acryloyl]-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-[7-(5-ethyl-thien-2-yl)-2,3,6,7-tetrahydro-[1,4]thiazepin-5-yl]-4-hydroxy-6-methyl-pyran-2-one (Compound 7); LCMS: MH$^+$ 349.9.

Proceeding as in Example 2, but substituting 3-[(E)-3-(1-benzyl-1H-indol-3-yl)acryloyl]-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-[7-(1-benzyl-1H-indol-3-yl)-2,3,6,7-tetrahydro-[1,4]thiazepin-5-yl]4-hydroxy-6-methyl-pyran-2-one (Compound 8); LCMS: MH$^+$ 445.2.

Proceeding as in Example 2, but substituting 4-hydroxy-6-methyl-3-[(E)-3-(2-trifluoromethylsulfanyl-phenyl)-acryloyl]-pyran-2-one for 4-hydroxy-3-[(E)-3-(2-methoxy-4-methylsulfanyl-phenyl)-acryloyl]-6-methyl-pyran-2-one, provided 4-hydroxy-6-methyl-3-[7-(2-trifluoromethylsulfanyl-phenyl)-2,3,6,7-tetrahydro-[1,4]thiazepin-5-yl]-pyran-2-one (Compound 9); LCMS: MH$^+$ 416.4.

Proceeding as in Example 2, but substituting 4-hydroxy-6-methyl-3-[(E)-3-(3-trifluoromethylsulfanyl-phenyl)-acryloyl]-pyran-2-one for 4-hydroxy-3-[(E)-3-(2-methoxy-4-methylsulfanyl-phenyl)-acryloyl]-6-methyl-pyran-2-one, provided 4-hydroxy-6-methyl-3-[7-(3-trifluoromethylsulfanyl-phenyl)-2,3,6,7-tetrahydro-[1,4]thiazepin-5-yl]-pyran-2-one (Compound 10); LCMS: MH$^+$ 416.6.

Proceeding as in Example 2, but substituting 4-hydroxy-6-methyl-3-[(E)-3-(4-trifluoromethylsulfanyl-phenyl)-acryloyl]-pyran-2-one for 4-hydroxy-3-[(E)-3-(2-methoxy-4-methylsulfanyl-phenyl)-acryloyl]-6-methyl-pyran-2-one, provided 4-hydroxy-6-methyl-3-[7-(4-trifluoromethylsulfanyl-phenyl)-2,3,6,7-tetrahydro-[1,4]thiazepin-5-yl]-pyran-2-one (Compound 11); LCMS: MH$^+$ 416.5.

Proceeding as in Example 2, but substituting 4-hydroxy-6-methyl-3-{(E)-3-[3-(3-trifluoromethyl-phenoxy)-phenyl]-acryloyl}-pyran-2-one for 4-hydroxy-3-[(E)-3-(2-methoxy-4-methylsulfanyl-phenyl)-acryloyl]-6-methyl-pyran-2-one, provided 4-hydroxy-6-methyl-3-{7-[3-(3-trifluoromethyl-phenoxy)-phenyl]-2,3,6,7-tetrahydro-[1,4]thiazepin-5-yl}-pyran-2-one (Compound 12); LCMS: MH$^+$ 476.2.

Proceeding as in Example 2, but substituting 3-{(E)-3-[3-(3,4-dichloro-phenoxy)-phenyl]-acryloyl}-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-{7-[3-(3,4-dichloro-phenoxy)-phenyl]-2,3,6,7-tetrahydro-[1,4]thiazepin-5-yl}-4-hydroxy-6-methyl-pyran-2-one (Compound 13); LCMS: MH$^+$ 475.8.

Proceeding as in Example 2, but substituting 3-{(E)-3-[3-(3,5-dichloro-phenoxy)-phenyl]-acryloyl}-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-{7-[3-(3,5-dichloro-phenoxy)-phenyl]-2,3,6,7-tetrahydro-[1,4]thiazepin-5-yl}-4-hydroxy-6-methyl-pyran-2-one (Compound 14); LCMS: MH$^+$ 475.9.

Proceeding as in Example 2, but substituting 4-hydroxy-6-methyl-3-{(E)-3-[5-(3-trifluoromethyl-phenyl)-furan-2-yl]-acryloyl}-pyran-2-one for 4-hydroxy-3-[(E)-3-(2-methoxy-4-methylsulfanyl-phenyl)-acryloyl]-6-methyl-pyran-2-one, provided 4-hydroxy-6-methyl-3-{7-[5-(3- trifluoromethyl-phenyl)-furan-2-yl]-2,3,6,7-tetrahydro-[1,4]thiazepin-5-yl}-pyran-2-one (Compound 15); LCMS: MH+ 450.1.

Proceeding as in Example 2, but substituting 3-{(E)-3-[5-(2-chloro-phenyl)-furan-2-yl]-acryloyl}-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-{7-[5-(2-chloro-phenyl)-furan-2-yl]-2,3,6,7-tetrahydro-[1,4]thiazepin-5-yl}-4-hydroxy-6-methyl-pyran-2-one (Compound 16); LCMS: MH+ 416.1.

Proceeding as in Example 2, but substituting 3-{(E)-3-[5-(3-chloro-phenyl)-furan-2-yl]-acryloyl}-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-{7-[5-(3-chloro-phenyl)-furan-2-yl]-2,3,6,7-tetrahydro-[1,4]thiazepin-5-yl}-4-hydroxy-6-methyl-pyran-2-one (Compound 17); LCMS: MH+ 416.1.

Proceeding as in Example 2, but substituting 3-{(E)-3-[5-(4-chloro-phenyl)-furan-2-yl]-acryloyl}-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-{7-[5-(4-chloro-phenyl)-furan-2-yl]-2,3,6,7-tetrahydro-[1,4]thiazepin-5-yl}-4-hydroxy-6-methyl-pyran-2-one (Compound 18); LCMS: MH+ 416.1.

Proceeding as in Example 2, but substituting 3-{(E)-3-[5-(2-chloro-5-trifluoromethyl-phenyl)-furan-2-yl]-acryloyl}-4-hydroxy-6-methyl-pyran-2-one for 4-hydroxy-3-[(E)-3-(2-methoxy4-methylsulfanyl-phenyl)-acryloyl]-6-methyl-pyran-2-one, provided 3-{7-[5-(2-chloro-5-trifluoromethyl-phenyl)-furan-2-yl]-2,3,6,7-tetrahydro-[1,4]thiazepin-5-yl}-4-hydroxy-6-methyl-pyran-2-one (Compound 19); LCMS: MH+ 483.9.

Proceeding as in Example 2, but substituting 3-[(E)-3-(4-bromo-thien-2-yl)-acryloyl]-4-hydroxy-6-methyl-pyran-2-one for 4-hydroxy-3-[(E)-3-(2-methoxy4-methylsulfanyl-phenyl)-acryloyl]-6-methyl-pyran-2-one, provided 3-[7-(4-bromo-thien-2-yl)-2,3,6,7-tetrahydro-[1,4]thiazepin-5-yl]-4-hydroxy-6-methyl-pyran-2-one (Compound 20); LCMS: MH+ 401.8.

Proceeding as in Example 2, but substituting 3-[(E)-3-(5-bromo-thien-2-yl)-acryloyl]-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-[7-(5-bromo-thien-2-yl)-2,3,6,7-tetrahydro-[1,4]thiazepin-5-yl]-4-hydroxy-6-methyl-pyran-2-one (Compound 21); LCMS: MH+ 401.8.

Proceeding as in Example 2, but substituting 3-[(E)-3-(1-benzenesulfonyl-1H-pyrrol-2-yl)-acryloyl]-4-hydroxy-6-methyl-pyran-2-one for4-hydroxy-3-[(E)-3-(2-methoxy-4-methylsulfanyl-phenyl)-acryloyl]-6-methyl-pyran-2-one, provided 3-[7-(1-benzenesulfonyl-1H-pyrrol-2-yl)-2,3,6,7-tetrahydro-[1,4]thiazepin-5-yl]-4-hydroxy-6-methyl-pyran-2-one (Compound 22); LCMS: MH+ 445.5.

Proceeding as in Example 2, but substituting 4-hydroxy-6-methyl-3-[(E)-3-(3-methyl-thien-2-yl)-acryloyl]-pyran-2-one for 4-hydroxy-3-[(E)-3-(2-methoxy-4-methylsulfanyl-phenyl)-acryloyl]-6-methyl-pyran-2-one, provided 4-hydroxy-6-methyl-3-[7-(3-methyl-thien-2-yl)-2,3,6,7-tetrahydro-[1,4]thiazepin-5-yl]-pyran-2-one (Compound 23); LCMS: MH+ 336.0.

Proceeding as in Example 2, but substituting 4-hydroxy-6-methyl-3-[(E)-3-(5-methyl-thien-2-yl)-acryloyl]-pyran-2-one for 4-hydroxy-3-[(E)-3-(2-methoxy-4-methylsulfanyl-phenyl)-acryloyl]-6-methyl-pyran-2-one, provided 4-hydroxy-6-methyl-3-[7-(5-methyl-thien-2-yl)-2,3,6,7-tetrahydro-[1,4]thiazepin-5-yl]-pyran-2-one (Compound 24); LCMS: MH+ 336.0.

Proceeding as in Example 2, but substituting 4-hydroxy-6-methyl-3-[(E)-3-(1-methyl-1H-indol-3-yl)-acryloyl]-pyran-2-one for 4-hydroxy-3-[(E)-3-(2-methoxy-4-methylsulfanyl-phenyl)-acryloyl]-6-methyl-pyran-2-one, provided 4-hydroxy-6-methyl-3-[7-(1-methyl-1H-indol-3-yl)-2,3,6,7-tetrahydro-[1,4]thiazepin-5-yl]-pyran-2-one (Compound 25); LCMS: MH+ 369.2.

Proceeding as in Example 2, but substituting 3-[(E)-3-(chloro-methyl-trifluoromethyl-1H-pyrazol4-yl)-acryloyl]-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-[7-(chloro-methyl-trifluoromethyl-1H-pyrazol-4-yl)-2,3,6,7-tetrahydro-[1,4]thiazepin-5-yl]-4-hydroxy-6-methyl-pyran-2-one (Compound 26); LCMS: MH+ 421.8.

Proceeding as in Example 2, but substituting 3-{(E)-3-[1-(2,4-difluoro-benzenesulfonyl)-1H-pyrrol-2-yl]-acryloyl}-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-{7-[1-(2,4-difluoro-benzenesulfonyl)-1H-pyrrol-2-yl]-2,3,6,7-tetrahydro-[1,4]thiazepin-5-yl}-4-hydroxy-6-methyl-pyran-2-one (Compound 28); LCMS: MH+ 480.8.

Proceeding as in Example 2, but substituting 3-((E)-3-[2,2']bithienyl-5-yl-acryloyl)-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-(7-[2,2']bithienyl-5-yl-2,3,6,7-tetrahydro-[1,4]thiazepin-5-yl)-4-hydroxy-6-methyl-pyran-2-one (Compound 29); LCMS: MH+ 404.0.

Proceeding as in Example 2, but substituting 3-{(E)-3-[1-(3,5-dichloro-phenyl)-1H-pyrrol-2-yl]-acryloyl}-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-{7-[1-(3,5-dichloro-phenyl)-1H-pyrrol-2-yl]-2,3,6,7-tetrahydro-[1,4]thiazepin-5-yl}-4-hydroxy-6-methyl-pyran-2-one (Compound 30); LCMS: MH+ 449.0.

Proceeding as in Example 2, but substituting 3-{(E)-3-[1-(4-chloro-phenyl)-1H-pyrrol-2-yl]-acryloyl}-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-{7-[1-(4-chloro-phenyl)-1H-pyrrol-2-yl]-2,3,6,7-tetrahydro-[1,4]thiazepin-5-yl}-4-hydroxy-6-methyl-pyran-2-one (Compound 31); LCMS: MH+ 415.2.

Proceeding as in Example 2, but substituting 3-[(E)-3-(5-chloro-1H-indol-3-yl)-acryloyl]-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-[7-(5-chloro-1H-indol-3-yl)-2,3,6,7-tetrahydro-[1,4]thiazepin-5-yl]-4-hydroxy-6-methyl-pyran-2-one (Compound 32); LCMS: MH+ 389.0.

Proceeding as in Example 2, but substituting 4-hydroxy-6-methyl-3-[(E)-3-(6-p-tolylsulfanyl-imidazo[2,1-b]thiazol-5-yl)-acryloyl]-pyran-2-one for 4-hydroxy-3-[(E)-3-(2-methoxy-4-methylsulfanyl-phenyl)-acryloyl]-6-methyl-pyran-2-one, provided 4-hydroxy-6-methyl-3-[7-(6-p-tolylsulfanyl-imidazo[2,1-b]thiazol-5-yl)-2,3,6,7-tetrahydro-[1,4]thiazepin-5-yl]-pyran-2-one (Compound 33); LCMS: MH+ 484.4.

Proceeding as in example 2, but substituting 3-[(E)-3-(4,5-dibromo-thien-2-yl)-acryloyl]-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-[7-(4,5-dibromo-thien-2-yl)-2,3,6,7-tetrahydro-[1,4]thiazepin-5-yl]-4-hydroxy-6-methyl-pyran-2-one (Compound 34); LCMS: MH+ 479.6.

Proceeding as in Example 2, but substituting 3-[(E)-3-(2-chloro-5-trifluoromethyl-phenyl)-acryloyl]-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-[7-(2-chloro-5-trifluoromethyl-phenyl)-2,3,6,7-tetrahydro-[1,4]thiazepin-5-yl]-4-hydroxy-6-methyl-pyran-2-one (Compound 35) 418.1.

Proceeding as in Example 2, but substituting 3-[(E)-3-(2,4-dimethoxy-phenyl)-acryloyl]-4-hydroxy-6-methyl-5,6-dihydro-pyran-2-one for 3-[3-(2,4-dimethoxy-phenyl)-acryloyl]-4-hydroxy-6-methyl-pyran-2-one, provided 3-[7-(2,4-dimethoxy-phenyl)-2,3,6,7-tetrahydro-[1,4]thiazepin-5-yl]-4-hydroxy-6-methyl-5,6-dihydro-pyran-2-one (Compound 36); MS M$^+$378.0; NMR (CDCl$_3$-TMS): d 13.00 (bs, 1H), 7.2 (d, 1H, J=9 Hz), 6.45 (m, 2H), 4.36 (d, 1H, J=9 Hz), 4.35 (m, 1H), 4.96–3.91 (m, 2H), 3.84 (s, 3H), 3.8 (m, 1H), 3.78 (s, 3H), 3.52 (dd, 1H, J=10 Hz), 2.98 (m, 1H), 2.77 (m, 1H), 2.55–2.36 (m, 2H), 1.35 (d, 3H, J=6.5 Hz).

Proceeding as in Example 2, but substituting 4-hydroxy-6-methyl-3-[(E)-3-(5-methylsulfanyl-thien-2-yl)-acryloyl]-pyran-2-one for 4-hydroxy-3-[(E)-3-(2-methoxy4-methylsulfanyl-phenyl)-acryloyl]-6-methyl-pyran-2-one, provided 4-hydroxy-6-methyl-3-[7-(5-methylsulfanyl-thien-2-yl)-2,3,6,7-tetrahydro-[1,4]thiazepin-5-yl]-pyran-2-one (Compound 37); LCMS: MH$^+$ 367.4.

Proceeding as in Example 2, but substituting 3-[(E)-3-(5-chloro-1-methyl-3-phenyl-1H-pyrazol-4-yl)-acryloyl]-4-hydroxy-pyran-2-one for 4-hydroxy-3-[(E)-3-(2-methoxy-4-methylsulfanyl-phenyl)-acryloyl]-6-methyl-pyran-2-one, provided 3-[7-(5-chloro-1-methyl-3-phenyl-1H-pyrazol-4-yl)-2,3,6,7-tetrahydro-[1,4]thiazepin-5-yl]-4-hydroxy-6-methyl-pyran-2-one (Compound 38); LCMS: MH$^+$ 430.0.

Proceeding as in Example 2, but substituting 2-[3-(2,4-dimethoxy-phenyl)-acryloyl]-3-hydroxy-cyclohex-2-enone for 3-[3-(2,4-dimethoxy-phenyl)-acryloyl]-4-hydroxy-6-methyl-pyran-2-one, provided 2-[7-(2,4-dimethoxy-phenyl)-2,3,6,7-tetrahydro-[1,4]thiazepin-5-yl]-3-hydroxy-cyclohex-2-enone (Compound 39); MS M$^+$ 361.8.

Proceeding as in Example 2, but substituting benzene-1,2-diamine for 2-aminoethanethiol, provided 3-[4-(2,4-dimethoxy-phenyl)-4,5-dihydro-3H-benzo[b][1,4]diazepin-2-yl]-4-hydroxy-6-methyl-pyran-2-one (Compound 40); LCMS: MH$^+$ 407.2.

Proceeding as in Example 2, but substituting 3-[(E)-3-(4-dimethylamino-phenyl)-acryloyl]-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-[7-(4-dimethylamino-phenyl)-2,3,6,7-tetrahydro-[1,4]thiazepin-5-yl]-4-hydroxy-6-methyl-pyran-2-one (Compound 42); MS M$^+$ 359.0.

Proceeding as in Example 2, but substituting 3-[(E)-3-(2,4-dimethoxy-phenyl)-acryloyl]-4-hydroxy-1H-quinolin-2-one for 3-[3-(2,4-dimethoxy-phenyl)-acryloyl]-4-hydroxy-6-methyl-pyran-2-one, provided 3-[7-(2,4-dimethoxy-phenyl)-2,3,6,7-tetrahydro-[1,4]thiazepin-5-yl]-4-hydroxy-1H-quinolin-2-one (Compound 43); MS M$^+$ 411.0.

Proceeding as in Example 2, but substituting 4-hydroxy-6-methyl-3-[(E)-3-(4-trifluoromethoxy-phenyl)-acryloyl]-pyran-2-one for 4-hydroxy-3-[(E)-3-(2-methoxy4-methylsulfanyl-phenyl)-acryloyl]-6-methyl-pyran-2-one, provided 4-hydroxy-6-methyl-3-[7-(4-trifluoromethoxy-phenyl)-2,3,6,7-tetrahydro-[1,4]thiazepin-5-yl]-pyran-2-one (Compound 44); MS M$^+$ 399.8.

Proceeding as in Example 2, but substituting 3-[(E)-3-(bis-trifluoromethyl-phenyl)-acryloyl]-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-[7-(bis-trifluoromethyl-phenyl)-2,3,6,7-tetrahydro-[1,4]thiazepin-5-yl]-4-hydroxy-6-methyl-pyran-2-one (Compound 45); MS M$^+$ 452.0.

Proceeding as in Example 2, but substituting 3-[(E)-3-(4-dimethylamino-2-methoxy-phenyl)-acryloyl]-4-hydroxy-6-methyl-pyran-2-one for 4-hydroxy-3-[(E)-3-(2-methoxy-4-methylsulfanyl-phenyl)-acryloyl]-6-methyl-pyran-2-one, provided 3-[7-(4-dimethylamino-2-methoxy-phenyl)-2,3,6,7-tetrahydro-[1,4]thiazepin-5-yl]-4-hydroxy-6-methyl-pyran-2-one (Compound 46); MS M$^+$ 389.0.

Proceeding as in Example 2, but substituting 4-hydroxy-3-[(E)-3-(4-methanesulfonyl-phenyl)-acryloyl]-6-methyl-pyran-2-one for 4-hydroxy-3-[(E)-3-(2-methoxy4-methylsulfanyl-phenyl)-acryloyl]-6-methyl-pyran-2-one, provided 4-hydroxy-3-[7-(4-methanesulfonyl-phenyl)-2,3,6,7-tetrahydro-[1,4]thiazepin-5-yl]-6-methyl-pyran-2-one (Compound 47); MS M$^+$ 393.8.

Proceeding as in Example 2, but substituting 3-[(E)-3-(2,4-diethoxy-phenyl)-acryloyl]4-hydroxy-6-methyl-pyran-2-one for 4-hydroxy-3-[(E)-3-(2-methoxy-4-methylsulfanyl-phenyl)-acryloyl]-6-methyl-pyran-2-one and 2-aminobenzenethiol for 2-aminoethanethiol, provided 3-[2-(2,4-diethoxy-phenyl)-2,3-dihydro-benzo[b][1,4]thiazepin-4-yl]-4-hydroxy-6-methyl-pyran-2-one (Compound 48); MS M$^+$ 452.0.

Proceeding as in Example 2, but substituting 3-[(E)-3-(2,4-diethoxy-phenyl)-acryloyl]-4-hydroxy-6-methyl-5,6-dihydro-pyran-2-one for4-hydroxy-3-[(E)-3-(2-methoxy-4-methylsulfanyl-phenyl)-acryloyl]-6-methyl-pyran-2-one, provided 3-[7-(2,4-diethoxy-phenyl)-2,3,6,7-tetrahydro-[1,4]thiazepin-5-yl]-4-hydroxy-6-methyl-5,6-dihydro-pyran-2-one (Compound 49); MS M$^+$ 406.2.

Proceeding as in Example 2, but substituting 3-[(E)-3-(4-dimethylamino-phenyl)-acryloyl]-4-hydroxy-6-methyl-5,6-dihydro-pyran-2-one for 4-hydroxy-3-[(E)-3-(2-methoxy-4-methylsulfanyl-phenyl)-acryloyl]-6-methyl-pyran-2-one, provided 3-[7-(4-dimethylamino-phenyl)-2,3,6,7-tetrahydro-1,4]thiazepin-5-yl]-4-hydroxy-6-methyl-5,6-dihydro-pyran-2-one (Compound 50); MS M$^+$ 361.0.

Proceeding as in Example 2, but substituting 2-[(E)-3-(2,4-diethoxy-phenyl)-acryloyl]-3-hydroxy-cyclohex-2-enone for 4-hydroxy-3-[(E)-3-(2-methoxy-4-methylsulfanyl-phenyl)-acryloyl]-6-methyl-pyran-2-one, provided 2-[7-(2,4-diethoxy-phenyl)-2,3,6,7-tetrahydro-[1,4]thiazepin-5-yl]-3-hydroxy-cyclohex-2-enone (Compound 51); MS M$^+$ 390.0.

Proceeding as in Example 2, but substituting 3-hydroxy-2-[(E)-3-(2,3,4-trimethoxy-phenyl)-acryloyl]-cyclohex-2-enone for 4-hydroxy-3-[(E)-3-(2-methoxy-4-methylsulfanyl-phenyl)-acryloyl]-6-methyl-pyran-2-one, provided 3-hydroxy-2-[7-(2,3,4-trimethoxy-phenyl)-2,3,6,7-tetrahydro-[1,4]thiazepin-5-yl]-cyclohex-2-enone (Compound 52); MS M$^+$ 392.2.

Proceeding as in Example 2, but substituting 2-[(E)-3-(2,4-diethoxy-phenyl)-acryloyl]-3-hydroxy-cyclohex-2-enone for 4-hydroxy-3-[(E)-3-(2-methoxy-4-methylsulfanyl-phenyl)-acryloyl]-6-methyl-pyran-2-one and 2-aminobenzenethiol for 2-aminoethanethiol, provided 2-[2-(2,4-diethoxy-phenyl)-2,3-dihydro-benzo[b][1,4]thiazepin-4-yl]-3-hydroxy-cyclohex-2-enone (Compound 53); MS M$^+$ 438.4.

Proceeding as in Example 2, but substituting 3-hydroxy-2-[(E)-3-(2,3,4-trimethoxy-phenyl)-acryloyl]-cyclohex-2-enone for 4-hydroxy-3-[(E)-3-(2-methoxy-4- methylsulfanyl-phenyl)-acryloyl]-6-methyl-pyran-2-one and 2-amino-benzenethiol for 2-aminoethanethiol, provided 3-hydroxy-2-[2-(2,3,4-trimethoxy-phenyl)-2,3-dihydro-benzo[b][1,4]thiazepin-4-yl]-cyclohex-2-enone (Compound 54); MS M+ 439.8.

Proceeding as in Example 2, but substituting 3-[3-(2,4-dimethoxy-phenyl)-acryloyl]-4-hydroxy-6-methyl-pyran-2-one for 4-hydroxy-3-[(E)-3-(2-methoxy-4-methylsulfanyl-phenyl)-acryloyl]-6-methyl-pyran-2-one and 2-amino-3-mercapto-3-methyl-butyric acid for 2-aminoethanethiol, provided 7-(2,4-dimethoxy-phenyl)-5-(4-hydroxy-6-methyl-2-oxo-2H-pyran-3-yl)-2,2-dimethyl-2,3,6,7-tetrahydro-[1,4]thiazepine-3-carboxylic acid (Compound 55); MS M+ 448.0.

Proceeding as in Example 2, but 4-hydroxy-6-methyl-3-[(E)-3-(2,3,4-trimethoxy-phenyl)-acryloyl]-5,6-dihydro-pyran-2-one substituted for 4-hydroxy-3-[(E)-3-(2-methoxy-4-methylsulfanyl-phenyl)-acryloyl]-6-methyl-pyran-2-one and 2-amino-benzenethiol for 2-aminoethanethiol, provided 4-hydroxy-6-methyl-3-[2-(2,3,4-trimethoxy-phenyl)-2,3-dihydro-benzo[b][1,4]thiazepin-4-yl]-5,6-dihydro-pyran-2-one (Compound 56); MS M+ 456.2.

Proceeding as in Example 2, but substituting 4-hydroxy-6-methyl-3-[(E)-3-(2,3,4-trimethoxy-phenyl)-acryloyl]-5,6-dihydro-pyran-2-one for 4-hydroxy-3-[(E)-3-(2-methoxy-4-methylsulfanyl-phenyl)-acryloyl]-6-methyl-pyran-2-one, provided 4-hydroxy-6-methyl-3-[7-(2,3,4-trimethoxy-phenyl)-2,3,6,7-tetrahydro-[1,4]thiazepin-5-yl]-5,6-dihydro-pyran-2-one (Compound 57); MS M+ 408.4.

Example 3

3-[7-(2,4-Dimethoxy-phenyl)-1-oxo-2,3,6,7-tetrahydro-1H-1$\lambda^4$-[1,4]thiazepin-5-yl]-4-hydroxy-6-methyl-pyran-2-one Compound 58

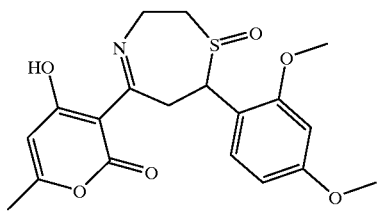

3-[7-(2,4-Dimethoxyphenyl)-2,3,6,7-tetrahydro-[1,4]thiazepin-5-yl]-4-hydroxy-6-methyl-pyran-2-one (0.12 g, 0.32 mmol), prepared as in Reference 5, was dissolved in acetic acid (2 mL) and then hydrogen peroxide (0.3 ml, 35 wt % in water) was added at room temperature. The reaction was monitored by analytical HPLC. After 2 hours the solvent was removed in vacuo. Product was purified by preparative HPLC (RPC$_{18}$ column, 2–60% acetonitrile/water containing 0.1% HCl) to provide a diasteromeric mixture of 3-[7-(2,4-dimethoxy-phenyl)-1-oxo-2,3,6,7-tetrahydro-1H-1$\lambda^4$-[1,4]thiazepin-5-yl]-4-hydroxy-6-methyl-pyran-2-one (4.4 mg) as a yellow powder. LCMS: MH+ 392.0.

Example 4

10-(2,4-Dimethoxy-phenyl)-3-methyl-7,8-dihydro-10H-2,5-dioxa-9-thia-6a-aza-cyclohepta[a]naphthalene-1,6-dione Compound 59

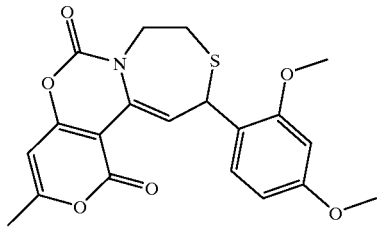

3-[7-(2,4-Dimethoxyphenyl)-2,3,6,7-tetrahydro-[1,4]thiazepin-5-yl]-4-hydroxy-6-methyl-pyran-2-one (63 mg, 0.168 mmol), prepared as in Reference 5, was dissolved in ethylene dichloride (2 mL) and then 4-(dimethylamino)pyridine (0.020 g), di-iso-propylethylamine (0.5 mL) and phosgene (0.4 ml, 2 M in toluene) were added at room temperature. The reaction was monitored by analytical HPLC. After stirring at room temperature for 30 minutes, the solvent was removed in vacuo. Product was purified by HPLC (RPC$_{18}$ column, 2–70% acetonitrile/water containing 0.1% HCl) to provide 10-(2,4-dimethoxy-phenyl)-3-methyl-7,8-dihydro-10H-2,5-dioxa-9-thia-6a-aza-cyclohepta[a]naphthalene-1,6-dione (20 mg) as an off-white powder. LCMS: M+ 401.0.

Example 5

3-[7-(2,4-Dimethoxy-phenyl)-1,1-dioxo-2,3,6,7-tetrahydro-1H-1$\lambda^6$[1,4]thiazepin-5-yl]4-hydroxy-6-methyl-pyran-2-one Compound 60

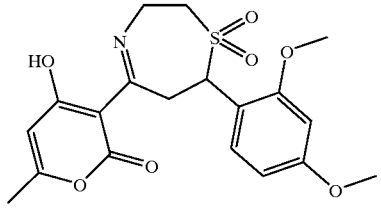

3-[7-(2,4-Dimethoxyphenyl)-2,3,6,7-tetrahydro-[1,4]thiazepin-5-yl]-4-hydroxy-6-methyl-pyran-2-one (190 mg, 0.5 mmol), prepared as in Reference 5, was dissolved in acetic acid (2 ml) and hydrogen peroxide (0.3 ml, 35 wt % in water) was added to the solution at room temperature. The clear solution was stirred at 70° C. The reaction was monitored by analytical HPLC. After 2 hours the solvent was removed in vacuo. Product was purified by preparative HPLC (RPC$_{18}$ column, 2–60% acetonitrile/water containing 0.1% HCl) to provide 3-[7-(2,4-dimethoxy-phenyl)-1,1-dioxo-2,3,6,7-tetrahydro-1H-1$\lambda^6$[1,4]thiazepin-5-yl]-4-hydroxy-6-methyl-pyran-2-one (10 mg) as a yellow powder. LCMS: MH+ 408.0.

Example 6

3-[7-(2,4-Dimethoxy-phenyl)-2,3-dihydro-[1,4]
thiazepin-5-yl]-4-hydroxy-6-methyl-pyran-2-one Compound 61

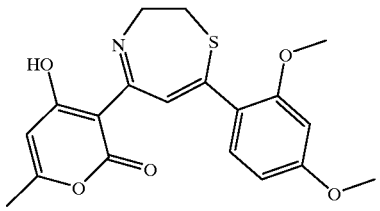

3-[7-(2,4-Dimethoxyphenyl)-2,3,6,7-tetrahydro-[1,4]
thiazepin-5-yl]-4-hydroxy-6-methyl-pyran-2-one (150 mg, 0.39 mmol), prepared as in Reference 5, was dissolved in toluene (2 ml) and 2,3-dichloro-5,6-dicyano-1,4-benzoquinone (0.3 mL, 35 wt % in water) was added to the solution. The mixture was stirred at 80° C. The reaction was monitored by analytical HPLC and after reaction was complete (20 minutes) the solvent was then removed in vacuo. Product was purified by preparative HPLC (RPC$_{18}$ column, 2–80% acetonitrile/water containing 0.1% HCl) to provide 3-[7-(2,4-dimethoxy-phenyl)-2,3-dihydro-[1,4]thiazepin-5-yl]-4-hydroxy-6-methyl-pyran-2-one (35 mg) as an orange powder. LCMS: MH$^+$ 373.0.

Proceeding as in Example 6, but substituting 3-[7-(2,4-diethoxy-phenyl)-2,3,6,7-tetrahydro-[1,4]thiazepin-5-yl]-4-hydroxy-6-methyl-pyran-2-one for 3-[7-(2,4-dimethoxyphenyl)-2,3,6,7-tetrahydro-[1,4]thiazepin-5-yl]-4-hydroxy-6-methyl-pyran-2-one, provided 3-[7-(2,4-diethoxy-phenyl)-2,3-dihydro-[1,4]thiazepin-5-yl]-4-hydroxy-6-methyl-pyran-2-one (Compound 62); MS M$^+$ 402.0.

Proceeding as in Example 6, but substituting 3-(7-[2,2']bithienyl-5-yl-2,3,6,7-tetrahydro-[1,4]thiazepin-5-yl)-4-hydroxy-6-methyl-pyran-2-one for 3-[7-(2,4-dimethoxyphenyl)-2,3,6,7-tetrahydro-[1,4]thiazepin-5-yl]-4-hydroxy-6-methyl-pyran-2-one, provided 3-(7-[2,2']bithienyl-5-yl-2,3-dihydro-[1,4]thiazepin-5-yl)-4-hydroxy-6-methyl-pyran-2-one (Compound 63); MS M$^+$ 402.2.

Proceeding as in Example 6, but substituting 2-[7-(2,4-diethoxy-phenyl)-2,3,6,7-tetrahydro-[1,4]thiazepin-5-yl]-3-hydroxy-cyclohex-2-enone for 3-[7-(2,4-dimethoxyphenyl)-2,3,6,7-tetrahydro-[1,4]thiazepin-5-yl]-4-hydroxy-6-methyl-pyran-2-one, provided 2-[7-(2,4-diethoxy-phenyl)-2,3-dihydro-[1,4]thiazepin-5-yl]-3-hydroxy-cyclohex-2-enone (Compound 64); MS M$^+$ 388.4.

Proceeding as in Example 6, but substituting 3-[7-(2,4-diethoxy-phenyl)-2,3,6,7-tetrahydro-[1,4]thiazepin-5-yl]4-hydroxy-6-methyl-5,6-dihydro-pyran-2-one for 3-[7-(2,4-dimethoxyphenyl)-2,3,6,7-tetrahydro-[1,4]thiazepin-5-yl]-4-hydroxy-6-methyl-pyran-2-one, provided 3-[7-(2,4-diethoxy-phenyl)-2,3-dihydro-[1,4]thiazepin-5-yl]-4-hydroxy-6-methyl-5,6-dihydro-pyran-2-one (Compound 65); MS M$^+$ 404.4.

Example 7

2-({1-[7-(2,4-Dimethoxy-phenyl)-5-(4-hydroxy-6-
methyl-2-oxo-2H-pyran-3-yl)-2,2-dimethyl-2,3,6,7-
tetrahydro-[1,4]thiazepin-3-yl]-methanoyl}-amino)-
propionic acid tert-butyl ester Compound 66

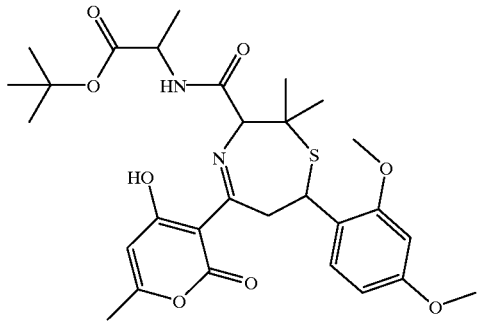

7-(2,4-Dimethoxy-phenyl)-5-(4-hydroxy-6-methyl-2-oxo-2H-pyran-3-yl)-2,2-dimethyl-2,3,6,7-tetrahydro-[1,4]thiazepine-3-carboxylic acid (0.03 g), prepared as in Example 2, was dissolved in DMF (2 mL) and 2-aminopropionic acid tert-butyl ester (0.012 g), N-methylmorpholine (0.2 ml) and PyBOP (0.034 g) were added to the solution at room temperature. The mixture was stirred while the progress of the reaction was followed by analytical HPLC and when complete (16 hours) the solvent was removed in vacuo. Purification of product by preparative HPLC (RPC$_{18}$ column, 2–70% acetonitrile/water containing 0.1% HCl) provided 2-({1-[7-(2,4-dimethoxy-phenyl)-5-(4-hydroxy-6-methyl-2-oxo-2H-pyran-3-yl)-2,2-dimethyl-2,3,6,7-tetrahydro-[1,4]thiazepin-3-yl]-methanoyl }-amino)-propionic acid tert-butyl ester (18 mg) as an off-white powder. LCMS: M$^+$ 575.0.

Proceeding by methods analogous to those described in the application the following compounds can be made:

4-hydroxy-6-methyl-3-[7-(4-methylsulfanyl-phenyl)-2,3,6,7-tetrahydro-[1,4]thiazepin-5-yl]-pyran-2-one (Compound 70), 3-[7-(4-ethoxy-phenyl)-2,3,6,7-tetrahydro-[1,4]thiazepin-5-yl]-4-hydroxy-6-methyl-pyran-2-one (Compound 71), 4-hydroxy-3-[7-(3-methoxy-phenyl)-2,3,6,7-tetrahydro-[1,4]thiazepin-5-yl]-6-methyl-pyran-2-one (Compound 72), 3-[7-(2-bromo-phenyl)-2,3,6,7-tetrahydro-[1,4]thiazepin-5-yl]4-hydroxy-6-methyl-pyran-2-one (Compound 74), 3-[7-(3,4-dichloro-phenyl)-2,3,6,7-tetrahydro-[1,4]thiazepin-5-yl]-4-hydroxy-6-methyl-pyran-2-one (Compound 79), 3-[7-(2,3-dichloro-phenyl)-2,3,6,7-tetrahydro-[1,4]thiazepin-5-yl]-4-hydroxy-6-methyl-pyran-2-one (Compound 82), 4-hydroxy-6-methyl-3-[7-(2,3,4-trimethoxy-phenyl)-2,3,6,7-tetrahydro-[1,4]thiazepin-5-yl]-pyran-2-one (Compound 83), 4-hydroxy-6-methyl-3-(2-p-tolyl-2,3-dihydro-benzo[b][1,4]thiazepin-4-yl)-pyran-2-one (Compound 85) and 4-hydroxy-6-methyl-3-[2-(4-methylsulfanyl-phenyl)-2,3-dihydro-benzo[b][1,4]thiazepin-4-yl]-pyran-2-one (Compound 86).

Example 8

Identification of Caspase Cascade Activators and Inducers of Apoptosis in Solid Tumor Cells Human breast cancer cell lines T-47D and ZR-75-1 were grown according to media component mixtures designated by American Type Culture Collection +10% fetal calf sera (FCS) (Life Technologies, Inc.) in a 5% $CO_2$-95% humidity incubator as 37° C. The T-47 and ZR-75-1 cells were maintained at a cell density between 30 and 80% confluency at a cell density of 0.1 to 0.6×10⁶ cells/mL. Cells were harvested at 600 xg and resuspended at 0.65×10⁶ cells/mL into appropriate media +10% FCS. An aliquot of 45 μL of cells was added to a well of a 96-well microtiter plate containing 5 μL of a 10% DMSO in RPMI-1640 media solution containing 1.6 to 100 μM of test compound (0.16 to 10 μM final).

An aliquot of 45 μL of cells was added to a well of a 96-well microtiter plate containing 5 μL of a 10% DMSO in RPMI-1640 media solution without test compound as the control sample. The samples were mixed by agitation and then incubated at 37° C. for 24 hours in a 5% $CO_2$-95% humidity incubator. After incubation, the samples were removed from the incubator and 50 μL of a solution w containing 20 μL of N-(Ac-DEVD)-N'-ethoxycarbonyl-R110 (SEQ ID NO:1) fluorogenic substrate (Cytovia, Inc.; WO99/18856), 20% sucrose (Sigma), 20 mM dithiothreitol (DTT) (Sigma), 200 mM NaCl (Sigma), 40 mM Na piperazine-N,N'-bis[2-ethanesulfonic acid] (PIPES) buffer pH 7.2 (Sigma), and 500 μg/mL lysolecithin (Calbiochem) was added. The samples were mixed by agitation and incubated at room temperature. Using a fluorescent plate reader (Model 1420 Wallac Instruments), an initial reading (T=0) was made approximately 1-2 minutes after addition of the substrate solution, employing excitation at 485 nm and emission at 530 nm, to determine the background fluorescence of the control sample. After the 3 hour incubation, the samples were read for fluorescence as above (T=3 hours).

Calculation:

The Relative Fluorescence Unit (RFU) values were used to calculate the sample readings as follows:

$RFU_{(T=3h)}$-Control $RFU_{(T=0)}$=Net $RFU_{(T=3h)}$

The level of caspase cascade activation was determined by the ratio of the net RFU value for the test compound to that of the control samples. The $EC_{50}$ (nM) was determined by a sigmoidal dose-response calculation (Prism 2.0, Graph-Pad Software, Inc.). The compounds of the invention were determined to have caspase cascade activating effects by proceeding as in Example 8.

TABLE I

| | Caspase Potency | |
|---|---|---|
| | $EC_{50}$ (nM) | |
| Compound # | T-47D | ZR-75-1 |
| 70 | 345 | 163 |
| 72 | 3050 | 1950 |
| 74 | 3270 | 2080 |
| 79 | 557 | 349 |
| 85 | 6930 | 4207 |

Example 9

Identification of Antineoplastic Activity in Cell Proliferation

T-47D and ZR-75-1 cells are grown and harvested by proceeding as in Example 8. An aliquot of 90 μL of cells (2.2×10⁴ cells/mL) is added to a well of a 96-well microtiter plate containing 10 μL of a 10% DMSO in PRMI-1640 media solution containing 1 mM to 100 μM of test compound. An aliquot of 90 μL of cells is added to a well of a 96-well microtiter plate containing 10 μL of a 10% DMSO in RPMI-1640 media solution without test compound as the control sample for maximal cell proliferation ($A_{max}$). The samples are mixed by agitation and then incubated at 37° C. for 48 hours in a 5% $CO_2$-95% humidity incubator. After incubation, the samples are removed from the incubator and 20 μL of CellTiter 96 Aqueous One Solution Cell Proliferation™ reagent (Promega) is added. The samples are mixed by agitation and incubated at 37° C. for 2-4 hours in a 5% $CO_2$-95% humidity incubator. Using an absorbance plate reader (Model 1420 Wallac Instruments), an initial reading (T=0) is made approximately 1-2 minutes after addition of the solution, employing absorbance at 490 nm, to determine any background absorbance of the test compound. After the 2-4 hours incubation, the samples are read for absorbance as above ($A_{test}$).

Baseline for the dose producing 50% inhibition of cell proliferation ($GI_{50}$) of initial cell numbers is determined by adding an aliquot of 90 μL of cells or 90 μL of media, respectively, to wells of a 96-well microtiter plate containing 10 μL of a 10% DMSO in RPMI-1640 media solution. The samples are mixed by agitation and then incubated at 37° C. for 0.5 hours in a 5% $CO_2$-95% humidity incubator. After incubation, the samples are removed from the incubator and 20 μL of CellTiter 96 Aqueous One Solution Cell Proliferation™ reagent (Promega) is added. The samples are mixed by agitation and incubated at 37° C. for 2-4 hours in a 5% $CO_2$-95% humidity incubator. Absorbance is read as above, ($A_{T=0}$) defining absorbance for initial cell number used as baseline $GI_{50}$ determinations.

Calculation:

$GI50(nM)=100\times[A_{test}-A_{T=0}/(A_{max}-A_{T=0})]$.

Example 10

Nuclear Fragmentation in T47D Cells

T47D cells are grown and harvested by proceeding as in Example 8 and treated with test compound followed by staining of the cell nuclei with Syto 16, a fluorescent DNA dye which stains nuclei. Shrunken and fragmented nuclei are hallmarks of caspase-mediated apoptosis. T47D cells treated with test compound for 48 hours exhibit shrunken and fragmented nuclei.

Example 11

Mitotic Arrest in Jurkat Cells

Jurkat cells are incubated with a range of concentrations of test compounds (0.02 μM to 5 μM) for 6 hours under normal growth conditions. Control cultures are treated with DMSO vehicle. The cells are then treated for 20 minutes with 800 nM Syto 16. Cytospin preparation are then prepared and the samples were viewed by fluorescent microscopy using a fluorescein filter set. For each concentration of test compound, the number of mitotic figures are counted and expressed as a percentage of the total number of cells. Three fields from each condition are evaluated and the mean and SEM were calculated and plotted as a function of drug concentration.

Example 12

Cell Cycle Arrest in Solid Tumor Cell Lines

T47D cells are grown and harvested by proceeding as in Example 8. Cells at 1×10⁶ are treated with test compound for 48 hours at 37° C. As a control, cells are also incubated with DMSO. Cells are harvested at 1200 rpm and washed twice with 5 mM EDTA/PBS. Cells are then resuspended in 300 μL of EDTA/PBS and 700 mL of 100% ethanol, vortexed and incubated at room temperature for 1 hour. Samples are spun down at 12000 rpm for 5 minutes and the supernatant is removed. A solution containing 100 μg/mL of propidium iodide and 1 mg/mL of RNAse A (fresh) is added to the samples and the samples are incubated for 1 hour at room temperature. Samples are then transferred to 12×75 mm polystyrene tubes and analyzed on a flow cytometer. All flow cytometry analyses are performed on FACScalibur (Becton Dickison) using Cell Quest analysis software.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound of Formula I:

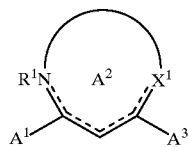

I in which:
the dashed lines indicate optional unsaturation without violating valency rules;
$R^1$ is hydrogen, $(C_{1-6})$alkyl or —C(O)$R^6$, wherein $R^6$ is as defined below, or $R^1$ is absent when a double bond exists between the nitrogen atom to which $R^1$ is attached and an adjacent ring atom;
$X^1$ is —S(O)$_n$—, wherein n is 0, 1, or 2;
$A^1$ is a monocyclic or fused polycyclic ring system selected from aryl containing a total of 6 to 14 ring atoms, heteroaryl containing a total of 5 to 14 ring atoms and unsaturated, partially unsaturated or saturated carbocycloalkyl or heterocycloalkyl each containing a total of 3 to 14 ring atoms, wherein $A^1$ may be substituted with a group selected from —$X^2R^3$, —$X^2OR^3$, —$X^2C(O)R^3$, —$X^2OC(O)R^3$, —$X^2C(O)OR^3$, —$X^2SR^3$, —$X^2S(O)R^3$, —$X^2S(O)_2R^3$, —$X^2NR^3R^4$, —$X^2NR^4C(O)R^3$, —$X^2NR^4C(O)OR^3$, —$X^2C(O)NR^3R^4$, —$X^2NR^4C(O)NR^3R^4$, —$X^2NR^4C(NR^4)NR^3R^4$, —$X^2NR^4S(O)_2R^3$ and —$X^2S(O)_2NR^3R^4$, wherein $X^2$ is a bond or $(C_{1-6})$alkylene, $R^3$ is —$X^2R^5$ wherein $X^2$ is as defined above and $R^5$ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and $R^4$ at each occurrence independently is hydrogen, $(C_{1-6})$alkyl or halo-substituted $(C_{1-6})$alkyl, wherein each ring within $A^1$ and $R^5$ contains from 3 to 8 ring atoms and may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR^4C(O)NR^4R^4$, —$X^2NR^4C(NR^4)NR^4R^4$, —$X^2NR^4S(O)_2R^6$ and —$X^2S(O)_2NR^4R^4$, wherein $X^2$ and $R^4$ are as defined above and $R^6$ is $(C_{1-6})$alkyl or halo-substituted $(C_{1-6})$alkyl, and wherein any said carbocycloalkyl and heterocycloalkyl rings within $A^1$ and $R^5$ may be substituted further with 1 to 2 groups independently selected from $(C_{1-6})$alkylidene, oxo, imino and thioxo, with the proviso that only one of $A^1$ and $R^5$ is a fused polycyclic ring system;

$A^2$ is a monocyclic ring selected from heteroarylene or unsaturated, partially unsaturated or saturated heterocycloalkylene containing a total of 7 ring atoms, wherein $A^2$ may be substituted with a group selected from —$X^2R^8$, —$X^2OR^8$, —$X^2C(O)R^8$, —$X^2OC(O)R^8$, —$X^2C(O)OR^8$, —$X^2SR^8$, —$X^2S(O)R^8$, —$X^2S(O)_2R^8$, —$X^2NR^4R^8$, —$X^2NR^4C(O)R^8$, —$X^2NR^4C(O)OR^8$, —$X^2C(O)NR^4R^8$, —$X^2NR^4C(O)NR^4R^8$, —$X^2NR^4C(NR^4)NR^4R^8$, —$X^2NR^4S(O)_2R^8$ and —$X^2S(O)_2NR^4R^8$, wherein $X^2$ is a bond or $(C_{1-6})$alkylene, $R^8$ is —$X^2R^9$ wherein $X^2$ is as defined above and $R^9$ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and $R^4$ at each occurrence independently is hydrogen, $(C_{1-6})$alkyl or halo-substituted $(C_{1-6})$alkyl, wherein each ring within $A^2$ and $R^8$ contains from 3 to 8 ring atoms and may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR^4C(O)NR^4R^4$, —$X^2NR^4C(NR^4)NR^4R^4$, —$X^2C(O)NR^4X^2C(O)OR^4$, —$X^2NR^2S(O)_2R^6$ and —$X^2S(O)_2NR^4R^4$, wherein $X^2$ and $R^4$ are as defined above and $R^6$ is $(C_{1-6})$alkyl or halo-substituted $(C_{1-6})$alkyl, and wherein any said heterocycloalkylene, carbocycloalkyl and heterocycloalkyl rings within $A^2$ and $R^8$ may be substituted further with 1 to 2 groups independently selected from $(C_{1-6})$alkylidene, oxo, imino and thioxo; and $A^3$ is a monocyclic or fused polycyclic ring system selected from aryl containing a total of 6 to 14 ring atoms, heteroaryl containing a total of 5 to 14 ring atoms and unsaturated, partially unsaturated or saturated carbocycloalkyl or heterocycloalkyl each containing a total of 3 to 14 ring atoms, wherein $A^3$ may be substituted with a group selected from —$X^2R^{9'}$, —$X^2OR^{9'}$, —$X^2C(O)R^{9'}$, —$X^2OC(O)R^{9'}$, —$X^2C(O)OR^{9'}$, —$X^2SR^{9'}$, —$X^2S(O)R^{9'}$, —$X^2S(O)_2R^{9'}$, —$X^2NR^4R^{9'}$, —$X^2NR^4C(O)R^{9'}$, —$X^2NR^4C(O)OR^{9'}$, —$X^2C(O)NR^4R^{9'}$, —$X^2NR^4C(O)NR^4R^{9'}$, —$X^2NR^4C(NR^4)NR^4R^{9'}$, —$X^2NR^4S(O)_2R^{9'}$ and —$X^2S(O)_2NR^4R^{9'}$, wherein $X^2$ is a bond or $(C_{1-6})$alkylene, $R^{9'}$ is —$X^2R^{10}$ wherein $X^2$ is as defined above and $R^{10}$ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and $R^4$ at each occurrence independently is hydrogen, $(C_{1-6})$alkyl or halo-substituted $(C_{1-6})$alkyl, wherein each ring within $A^3$ and $R^{10}$ contains from 3 to 8 ring atoms and may be substituted with 1 to 3 groups independently selected from $(C_{1-6})$alkyl, cyano, halo, nitro, halo-substituted $(C_{1-6})$alkyl, —$X^2OR^4$, —$X^2C$ (O)R⁶, —X²OC(O)R⁶, —X²C(O)OR⁴, —X²SR⁴, —X²S(O)R⁶, —X²S(O)₂R⁶, —X²NR⁴R⁴, —X²NR⁴C(O)R⁶, —X²NR⁴C(O)OR⁴, —C(O)NR⁴R⁴, —X²NR⁴C(O)NR⁴R⁴, —X²NR⁴C(NR⁴)NR⁴R⁴, —X²NR⁴S(O)₂R⁶ and —X²S(O)₂NR⁴R⁴, wherein X² and R⁴ are as defined above and R⁶ is (C₁₋₆)alkyl or halo-substituted (C₁₋₆)alkyl, and wherein any said carbocycloalkyl and heterocycloalkyl rings within A³ and R¹⁰ may be substituted further with 1 to 2 groups independently selected from (C₁₋₆)alkylidene, oxo, imino and thioxo, with the proviso that only one of A³ and R¹⁰ is a fused polycyclic ring system; and the individual stereoisomers and mixtures of stereoisomers; and the pharmaceutically acceptable salts thereof; with the proviso that when said compound is Formulae II(a):

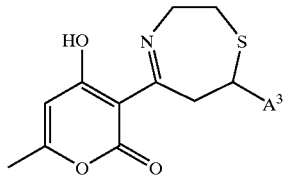

then A³ is other than:

unsubstituted pyridyl;

unsubstituted thienyl;

unsubstituted indolyl;

unsubstituted phenyl;

benzo[1,3]dioxolyl;

2,3-dihydro-benzo[1,4]dioxinyl;

phenyl which is mono-substituted by fluoro, bromo, iodo, nitro, methyl, isopropyl, ethoxy or methylsulfanyl; and phenyl which is substituted by at least one of chloro, hydroxy or methoxy.

2. The compound of claim 1, and the individual stereoisomers and mixtures of stereoisomers; and the pharmaceutically acceptable salts of said compound, with the further proviso that A³ is other than:

unsubstituted pyridyl;

unsubstituted thienyl;

unsubstituted indolyl;

unsubstituted phenyl;

benzo[1,3]dioxolyl;

2,3-dihydro-benzo[1,4]dioxinyl; and phenyl which is substituted by at least one of halogen, nitro, hydroxy, (C₁₃)alkyl, methoxy, ethoxy and methylsulfanyl.

3. The compound of claim 1, and the individual stereoisomers and mixtures of stereoisomers; and the pharmaceutically acceptable salts of said compound, with the further proviso that A¹ is not 4-hydroxy-6-methyl-2-oxo-2H-pyran-3-yl.

4. The compound of claim 1 in which said compound is of Formula I(A):

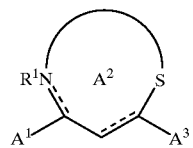

in which R¹, A¹, A² and A³ are as defined in claim 1; and the individual stereoisomers and mixtures of stereoisomers; and the pharmaceutically acceptable salts thereof.

5. The compound of claim 4 in which said compound is of Formula I(B):

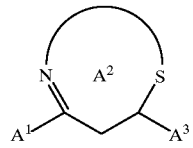

and the individual stereoisomers and mixtures of stereoisomers; and the pharmaceutically acceptable salts thereof.

6. The compound of claim 5 in which said A² is 2,3,6,7-tetrahydro-[1,4]thiazepin-5,7-ylene, that is the compound of Formula I(C):

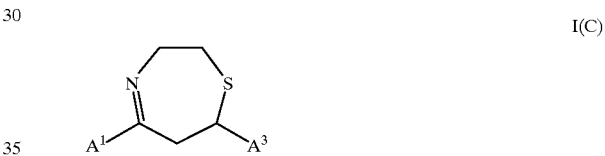

in which said 2,3,6,7-tetrahydro-[1,4]thiazepin-5,7-ylene may be substituted with 1 to 3 groups independently selected from (C₁₋₆)alkyl, cyano, halo, nitro, halo-substituted (C₁₋₆)alkyl, —X²OR⁴, —X²C(O)R⁶, —X²OC(O)R⁶, —X²C(O)OR⁴, —X²SR⁴, —X²S(O)R⁶, —X²S(O)₂R⁶, —X²NR⁴R⁴, —X²NR⁴C(O)R⁶, —X²NR⁴C(O)OR⁴, —X²C(O)NR⁴R⁴, —X²NR⁴C(O)NR⁴R⁴, —X²NR⁴C(NR⁴)NR⁴R⁴, —X²C(O)NR⁴X²C(O)OR⁴, —X²NR⁴S(O)₂R⁶ and —X²S(O)₂NR⁴R⁴, wherein X² is a bond or (C₁₋₆)alkylene, R⁴ at each occurrence independently is hydrogen, (C₁₋₆)alkyl or halo-substituted (C₁₋₆)alkyl, and R⁶ is (C₁₋₆)alkyl or halo-substituted (C₁₋₆)alkyl; and the individual stereoisomers and mixtures of stereoisomers; and the pharmaceutically acceptable salts thereof.

7. The compound of claim 6 in which A¹ is 4-hydroxy-6-methyl-2-oxo-2H-pyran-3-yl or 4-methoxy-6-methyl-2-oxo-2H-pyran-3-yl; and the individual stereoisomers and mixtures of stereoisomers; and the pharmaceutically acceptable salts thereof.

8. The compound of claim 7 in which said compound is selected from the group consisting of:

4-hydroxy-6-methyl-3-[7-(3-phenyl-1H-pyrazol-4-yl)-2,3,6,7-tetrahydro-[1,4]thiazepin-5-yl]-pyran-2-one;

3-[7-(5-ethyl-thien-2-yl)-2,3,6,7-tetrahydro-[1,4]thiazepin-5-yl]-4-hydroxy-6-methyl-pyran-2-one;

3-[7-(1-benzyl-1H-indol-3-yl)-2,3,6,7-tetrahydro-[1,4]thiazepin-5-yl]-4-hydroxy-6-methyl-pyran-2-one;

4-hydroxy-6-methyl-3[7-(2-trifluoromethylsulfanyl-phenyl)-2,3,6,7-tetrahydro-[1,4]thiazepin-5-yl]-pyran-2-one;

4-hydroxy-6-methyl-3[7-(3-trifluoromethylsulfanyl-phenyl)-2,3,6,7-tetrahydro-[1,4]thiazepin-5-yl]-pyran-2-one;

4-hydroxy-6-methyl-3[7-(4-trifluoromethylsulfanyl-phenyl)-2,3,6,7-tetrahydro-[1,4]thiazepin-5-yl]-pyran-2-one;

4-hydroxy-6-methyl-3-[7-[3-(3-trifluoromethyl-phenoxy)-phenyl]-2,3,6,7-tetrahydro-[1,4]thiazepin-5-yl]-pyran-2-one;

3-[7-[3-(3,4-dichloro-phenoxy)-phenyl]-2,3,6,7-tetrahydro-[1,4]thiazepin-5-yl]-4-hydroxy-6-methyl-pyran-2-one;

3-[7-[3-(3,5-dichloro-phenoxy)-phenyl]-2,3,6,7-tetrahydro-[1,4]thiazepin-5-yl]-4-hydroxy-6-methyl-pyran-2-one;

4-hydroxy-6-methyl-3-{7-[5-(3-trifluoromethyl-phenyl)-furan-2-yl]-2,3,6,7-tetrahydro-[1,4]thiazepin-5-yl}-pyran-2-one;

3-{7-[5-(2-chloro-phenyl)-furan-2-yl]-2,3,6,7-tetrahydro-[1,4]thiazepin-5-yl}-4-hydroxy-6-methyl-pyran-2-one;

3-{7-[5-(3-chloro-phenyl)-furan-2-yl]-2,3,6,7-tetrahydro-[1,4]thiazepin-5-yl}-4-hydroxy-6-methyl-pyran-2-one;

3-{7-[5-(4-chloro-phenyl)-furan-2-yl]-2,3,6,7-tetrahydro-[1,4]thiazepin-5-yl}-4-hydroxy-6-methyl-pyran-2-one;

4-hydroxy-6-methyl-3-{7-[5-(2-chloro-5-trifluoromethyl-phenyl)-furan-2-yl]-2,3,6,7-tetrahydro-[1,4]thiazepin-5-yl}-pyran-2-one;

3-[7-(4-bromo-thien-2-yl)-2,3,6,7-tetrahydro-[1,4]thiazepin-5-yl]-4-hydroxy-6-methyl-pyran-2-one;

3-[7-(5-bromo-thien-2-yl)-2,3,6,7-tetrahydro-[1,4]thiazepin-5-yl]-4-hydroxy-6-methyl-pyran-2-one;

3-[7-(1-benzenesulfonyl-1H-pyrrol-2-yl)-2,3,6,7-tetrahydro-[1,4]thiazepin-5-yl]-4-hydroxy-6-methyl-pyran-2-one;

4-hydroxy-6-methyl-3-[7-(3-methyl-thien-2-yl)-2,3,6,7-tetrahydro-[1,4]thiazepin-5-yl]-pyran-2-one;

4-hydroxy-6-methyl-3-[7-(5-methyl-thien-2-yl)-2,3,6,7-tetrahydro-[1,4]thiazepin-5-yl]-pyran-2-one;

4-hydroxy-6-methyl-3-[7-(1-methyl-1H-indol-3-yl)-2,3,6,7-tetrahydro-[1,4]thiazepin-5-yl]-pyran-2-one;

3-[7-(3-chloro-2-methyl-5-trifluoromethyl-1H-pyrazol-4-yl)-2,3,6,7-tetrahydro-[1,4]thiazepin-5-yl]-4-hydroxy-6-methyl-pyran-2-one;

3-{7-[1-(2,4-difluoro-benzenesulfonyl)-1H-pyrrol-2-yl]-2,3,6,7-tetrahydro-[1,4]thiazepin-5-yl}-4-hydroxy-6-methyl-pyran-2-one;

3-(7-[2,2']bithienyl-5-yl-2,3,6,7-tetrahydro-[1,4]thiazepin-5-yl)-4-hydroxy-6-methyl-pyran-2-one;

3-{7-[1-(3,5-dichloro-phenyl)-1H-pyrrol-2-yl]-2,3,6,7-tetrahydro-[1,4]thiazepin -5-yl}-4-hydroxy-6-methyl-pyran-2-one;

3-{7-[1-(4-chloro-phenyl)-1H-pyrrol-2-yl]-2,3,6,7-tetrahydro-[1,4]thiazepin-5-yl}-4-hydroxy-6-methyl-pyran-2-one;

3-[7-(5-chloro-1H-indol-3-yl)-2,3,6,7-tetrahydro-[1,4]thiazepin-5-yl]-4-hydroxy-6-methyl-pyran-2-one;

4-hydroxy-6-methyl-3-[7-(6-p-tolylsulfanyl-imidazo[2,1-b]thiazol-5-yl)-2,3,6,7-tetrahydro-[1,4]thiazepin-5-yl]-pyran-2-one;

3-[7-(4,5-dibromo-thien-2-yl)-2,3,6,7-tetrahydro-[1,4]thiazepin-5-yl]-4-hydroxy-6-methyl-pyran-2-one;

4-hydroxy-6-methyl-3-[7-(5-methylsulfanyl-thien-2-yl)-2,3,6,7-tetrahydro-[1,4]thiazepin-5-yl]-pyran-2-one;

3-[7-(5-chloro-1-methyl-3-phenyl-1H-pyrazol-4-yl)-2,3,6,7-tetrahydro-[1,4]thiazepin-5-yl]-4-hydroxy-6-methyl-pyran-2-one;

3-[7-(4-dimethylamino-phenyl)-2,3,6,7-tetrahydro-[1,4]thiazepin-5-yl]-4-hydroxy-6-methyl-pyran-2-one;

4-hydroxy-6-methyl-3-[7-(4-trifluoromethoxy-phenyl)-2,3,6,7-tetrahydro-[1,4]thiazepin-5-yl]-pyran-2-one;

3-[7-(bis-trifluoromethyl-phenyl)-2,3,6,7-tetrahydro-[1,4]thiazepin-5-yl]-4-hydroxy-6-methyl-pyran-2-one;

4-hydroxy-3-[7-(4-methanesulfonyl-phenyl)-2,3,6,7-tetrahydro-[1,4]thiazepin-5-yl]-6-methyl-pyran-2-one; and 3-[7-(2,4-dimethoxy-phenyl)-2,3,6,7-tetrahydro-[1,4]thiazepin-5-yl]-4-methoxy-6-methyl-pyran-2-one; and the pharmaceutically acceptable salts thereof.

9. The compound of claim 6 in which $A^1$ is 4-hydroxy-6-methyl-2-oxo-5,6-dihydro-2H-pyran-3-yl or 4-methoxy-6-methyl-2-oxo-5,6-dihydro-2H-pyran-3-yl; and the individual stereoisomers and mixtures of stereoisomers; and the pharmaceutically acceptable salts thereof.

10. The compound of claim 9 in which said compound is selected from the group consisting of:

3-[7-(2,4-dimethoxy-phenyl)-2,3,6,7-tetrahydro-[1,4]thiazepin-5-yl]-4-hydroxy-6-methyl-5,6-dihydro-pyran-2-one;

3-[7-(2,4-diethoxy-phenyl)-2,3,6,7-tetrahydro-[1,4]thiazepin-5-yl]-4-hydroxy-6-methyl-5,6-dihydro-pyran-2-one;

3-[7-(4-dimethylamino-phenyl)-2,3,6,7-tetrahydro-[1,4]thiazepin-5-yl]-4-hydroxy-6-methyl-5,6-dihydro-pyran-2-one; and 3-[7-(2,3,4-trimethoxy-phenyl)-2,3,6,7-tetrahydro-[1,4]thiazepin-5-yl]-4-hydroxy-6-methyl-5,6-dihydro-pyran-2-one; and the pharmaceutically acceptable salts thereof.

11. The compound of claim 6 in which $A^1$ is 2-hydroxy-6-oxo-cyclohex-1-enyl or 2-methoxy-6-oxo-cyclohex-1-enyl; and the individual stereoisomers and mixtures of stereoisomers; and the pharmaceutically acceptable salts thereof.

12. The compound of claim 11 in which said compound is selected from the group consisting of:

2-[7-(2,4-dimethoxy-phenyl)-2,3,6,7-tetrahydro-[1,4]thiazepin-5-yl]-3-hydroxy-cyclohex-2-enone;

2-[7-(2,4-diethoxy-phenyl)-2,3,6,7-tetrahydro-[1,4]thiazepin-5-yl]-3-hydroxy-cyclohex-2-enone; and 3-hydroxy-2-[7-(2,3,4-trimethoxy-phenyl)-2,3,6,7-tetrahydro-[1,4]thiazepin-5-yl]-cyclohex-2-enone; and the pharmaceutically acceptable salts thereof.

13. The compound of claim 6 in which $A^1$ is a group of Formula (c):

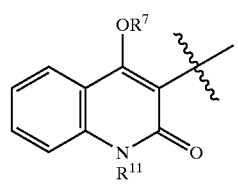

(c)

in which $R^7$ is hydrogen or methyl, $R^{11}$ is hydrogen or $(C_{1-6})$alkyl and the free valence is attached to $A^2$; and the individual stereoisomers and mixtures of stereoisomers; and the pharmaceutically acceptable salts thereof.

14. The compound of claim 13 which is:
3-[7–2,4-dimethoxy-phenyl)-2,3,6,7-tetrahydro-[1,4] thiazepin-5-yl]-4-hydroxy-1H-quinolin-2-one;
and the pharmaceutically acceptable salts thereof.

15. The compound of claim 4 in which said $A^2$ is a group of Formula (k):

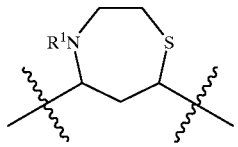

in which said group of Formula (k) may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR^4C(O)NR^4R^4$, —$X^2NR^4C(NR^4)NR^4R^4$, —$X^2C(O)NR^4X^2C(O)OR^4$, —$X^2NR^4S(O)_2R^6$ and —$X^2S(O)_2NR^4R^4$, wherein $X^2$ is a bond or $(C_{1-6})$alkylene, $R^4$ at each occurrence independently is hydrogen, $(C_{1-6})$alkyl or halo-substituted $(C_{1-6})$alkyl, and $R^6$ is $(C_{1-6})$alkyl or halo-substituted $(C_{1-6})$alkyl; and the individual stereoisomers and mixtures of stereoisomers; and the pharmaceutically acceptable salts thereof.

16. The compound of claim 15 in which $R^1$ is hydrogen; and the individual stereoisomers and mixtures of stereoisomers; and the pharmaceutically acceptable salts thereof.

17. The compound of claim 15 in which $A^1$ is 4-hydroxy-6-methyl-2-oxo-2H-pyran-3-yl or 4-methoxy-6-methyl-2-oxo-2H-pyran-3-yl; and the individual stereoisomers and mixtures of stereoisomers; and the pharmaceutically acceptable salts thereof.

18. The compound of claim 17 in which said compound is selected from the group consisting of:
3-[4-acetyl-7-(2,4-dimethoxy-phenyl)-[1,4]thiazepan-5-yl]-4-hydroxy-6-methyl -pyran-2-one; and
3-[7-(2,4-dimethoxy-phenyl)-4-(2,2,2-trifluoro-ethanoyl)-[1,4]thiazepan-5-yl]-4-hydroxy-6-methyl-pyran-2-one;
and the pharmaceutically acceptable salts thereof.

19. The compound of claim 15 in which $A^1$ is optionally substituted phenyl.

20. The compound of claim 19 which is:
1-[7-(2,4-dimethoxy-phenyl)-5-(3-fluoro-4-methoxyphenyl)-[1,4]thiazepan-4-yl]-ethanone;
and the pharmaceutically acceptable salts thereof.

21. The compound of claim 4 in which said $A^2$ is 2,3-dihydro-[1,4]thiazepin-5,7-ylene that is the compound of Formula I(F):

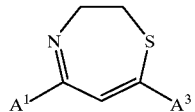

in which said 2,3-dihydro-[1,4]thiazepin-5,7-ylene may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR^4C(O)NR^4R^4$, —$X^2NR^4C(NR^4)NR^4R^4$, —$X^2C(O)NR^4X^2C(O)OR^4$, —$X^2NR^4S(O)_2R^6$ and —$X^2S(O)_2NR^4R^4$, wherein $X^2$ is a bond or $(C_{1-6})$alkylene, $R^4$ at each occurrence independently is hydrogen, $(C_{1-6})$alkyl or halo-substituted $(C_{1-6})$alkyl, and $R^6$ is $(C_{1-6})$alkyl or halo-substituted $(C_{1-6})$alkyl; and the individual stereoisomers and mixtures of stereoisomers; and the pharmaceutically acceptable salts thereof.

22. The compound of claim 21 in which $A^1$ is 4-hydroxy-6-methyl-2-oxo-2H-pyran-3-yl or 4-methoxy-6-methyl-2-oxo-2H-pyran-3-yl; and the individual stereoisomers and mixtures of stereoisomers; and the pharmaceutically acceptable salts thereof.

23. The compound of claim 22 in which said compound is selected from the group consisting of:
3-[7-(2,4-dimethoxy-phenyl)-2,3-dihydro-[1,4]thiazepin-5-yl]-4-hydroxy-6-methyl-pyran-2-one;
3-[7-(2,4-diethoxy-phenyl)-2,3-dihydro-[1,4]thiazepin-5-yl]-4-hydroxy-6-methyl -pyran-2-one; and
3-(7-[2,2']bithienyl-5-yl-2,3-dihydro-[1,4]thiazepin-5-yl)-4-hydroxy-6-methyl-pyran-2-one;
and the pharmaceutically acceptable salts thereof.

24. The compound of claim 21 in which $A^1$ is 4-hydroxy-6-methyl-2-oxo-5,6-dihydro-2H-pyran-3-yl or 4-methoxy-6-methyl-2-oxo-5,6-dihydro-2H-pyran-3-yl; and the individual stereoisomers and mixtures of stereoisomers; and the pharmaceutically acceptable salts thereof.

25. The compound of claim 24 which is:
3-[7-(2,4-diethoxy-phenyl)-2,3-dihydro-[1,4]thiazepin-5-yl]-4-hydroxy-6-methyl -5,6-dihydro-pyran-2-one;
and the pharmaceutically acceptable salts thereof.

26. The compound of claim 26 in which $A^1$ is 2-hydroxy-6-oxo-cyclohex-1-enyl or 2-methoxy-6-oxo-cyclohex-1-enyl; and the individual stereoisomers and mixtures of stereoisomers; and the pharmaceutically acceptable salts thereof.

27. The compound of claim 26 which is:
2-[7-(2,4-diethoxy-phenyl)-2,3-dihydro-[1,4]thiazepin-5-yl]-3-hydroxy-cyclohex-2-enone;
and the individual stereoisomers and mixtures of stereoisomers; and the pharmaceutically acceptable salts thereof.

28. The compound of claim 1 in which said compound is of Formula I(G):

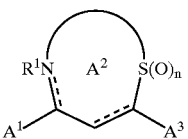

in which n, $R^1$, $A^1$, $A^2$ and $A^3$ are defined as in claim 1; and the individual stereoisomers and mixtures of stereoisomers; and the pharmaceutically acceptable salts thereof.

29. The compound of claim 28 in which $A^2$ is a group of Formula (1):

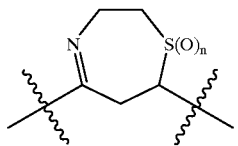
(I)

in which said group of Formula (1) may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —$X^2S(O)_2R^6$, —$X^2NR^4R^4$, —$X^2NR^4C(O)R^6$, —$X^2NR^4C(O)OR^4$, —$X^2C(O)NR^4R^4$, —$X^2NR^4C(O)NR^4R^4$, —$X^2NR^4C(NR^4)NR^4R^4$, —$X^2C(O)NR^4X^2C(O)OR^4$, —$X^2NR^4S(O)_2R^6$ and —$X^2S(O)_2NR^4R^4$, wherein $X^2$ is a bond or $(C_{1-6})$alkylene, $R^4$ at each occurrence independently is hydrogen, $(C_{1-6})$alkyl or halo-substituted $(C_{1-6})$alkyl, and $R^6$ is $(C_{1-6})$alkyl or halo-substituted $(C_{1-6})$alkyl; and the individual stereoisomers and mixtures of stereoisomers; and the pharmaceutically acceptable salts thereof.

30. The compound of claim 29 in which n is 1 and $A^1$ is 4-hydroxy-6-methyl-2-oxo-2H-pyran-3-yl or 4-methoxy-6-methyl-2-oxo-2H-pyran-3-yl; and the individual stereoisomers and mixtures of stereoisomers; and the pharmaceutically acceptable salts thereof.

31. The compound of claim 30 which is:
3-[7-(2,4-dimethoxy-phenyl)-1-oxo-2,3,6,7-tetrahydro-1H-1$\lambda^4$-[1,4]thiazepin-5-yl]-4-hydroxy-6-methyl-pyran-2-one;
and the pharmaceutically acceptable salts thereof.

32. The compound of claim 29 in which n is 2 and $A^1$ is 4-hydroxy-6-methyl-2-oxo-2H-pyran-3-yl or 4-methoxy-6-methyl-2-oxo-2H-pyran-3-yl; and the individual stereoisomers and mixtures of stereoisomers; and the pharmaceutically acceptable salts thereof.

33. The compound of claim 32 which is:
3-[7-(2,4-dimethoxy-phenyl)-1,1-dioxo-2,3,6,7-tetrahydro-1H-1$\lambda^6$-[1,4]thiazepin-5-yl]-4-hydroxy-6-methyl-pyran-2-one;
and the individual stereoisomers and mixtures of stereoisomers; and the pharmaceutically acceptable salts thereof.

34. A compound selected from the group consisting of:
4-hydroxy-3-[7-(2-methoxy-4-methylsulfanyl-phenyl)-2,3,6,7-tetrahydro-[1,4]thiazepin-5-yl]-6-methyl-pyran-2-one;
3-[7-(2-chloro-5-trifluoromethyl-phenyl)-2,3,6,7-tetrahydro-[1,4]thiazepin-5-yl]-4-hydroxy-6-methyl-pyran-2-one;
3-[7-(4-dimethylamino-2-methoxy-phenyl)-2,3,6,7-tetrahydro-[1,4]thiazepin-5-yl]-4-hydroxy-6-methyl-pyran-2-one;
4-hydroxy-3-[7-(4-chloro-2-methoxy-phenyl)-2,3,6,7-tetrahydro-[1,4]thiazepin-5-yl]-6-methyl-pyran-2-one; and
4-hydroxy-3-[7-(2,4-diethoxy-phenyl)-2,3,6,7-tetrahydro-[1,4]thiazepin-5-yl]-6-methyl-pyran-2-one;
or
an individual stereoisomer and mixtures of stereoisomers; or the pharmaceutically acceptable salt thereof.

35. A compound selected from the group consisting of:
7-(2,4-dimethoxy-phenyl)-5-(4-hydroxy-6-methyl-2-oxo-2H-pyran-3-yl)-2,2-dimethyl-2,3,6,7-tetrahydro-[1,4]thiazepine-3-carboxylic acid; and 2-({1-[7-(2,4-dimethoxy-phenyl)-5-(4-hydroxy-6-methyl-2-oxo-2H-pyran-3-yl)-2,2-dimethyl-2,3,6,7-tetrahydro-[1,4]thiazepin-3-yl]-methanoyl}-amino)-propionic acid tert-butyl ester;
and the pharmaceutically acceptable salts thereof.

36. The compound of claim 1 in which $A^1$ is a group selected from Formulae (b), (c), (d), (e) and (f):

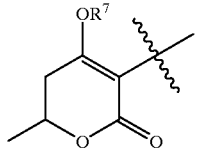
(b)

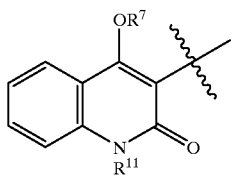
(c)

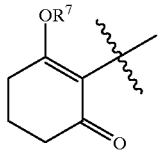
(d)

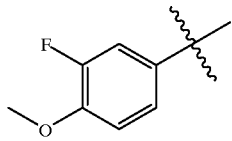
(e)

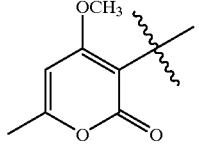
(f)

in which $R^7$ is hydrogen or methyl, $R^{11}$ is hydrogen or $(C_{1-6})$alkyl and the free valance is attached to $A^2$; and $A^2$ is as defined in claim 1 or is a monocyclic ring from heteroarylene or unsaturated, partially unsaturated or saturated heterocycloalkylene containing a total of 7 ring atoms, wherein $A^2$ may be substituted with a group selected from —$X^2R^8$, —$X^2OR^8$, —$X^2C(O)R^8$, —$X^2OC(O)R^8$, —$X^2C(O)OR^8$, —$X^2SR^8$, —$X^2S(O)R^8$, —$X^2S(O)_2R^8$, —$X^2NR^4R^8$, —$X^2NR^4C(O)R^8$, —$X^2NR^4C(O)OR^8$, —$X^2C(O)NR^4R^8$, —$X^2NR^4C(O)NR^4R^8$, —$X^2NR^4C(NR^4)NR^4R^8$, —$X^2NR^4S(O)_2R^8$ and —$X^2S(O)_2NR^4R^8$, wherein $X^2$ is a bond or $(C_{1-6})$alkylene, $R^8$ is —$X^2R^9$ wherein $X^2$ is as defined above and $R^9$ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and $R^4$ at each occurrence independently is hydrogen, $(C_{1-6})$alkyl or halo-substituted $(C_{1-6})$alkyl, wherein each ring within $A^2$ and $R^8$ that contains from 3 to 8 ring atoms and may be substituted with 1 to 3 groups independently selected from $(C_{1-6})$alkyl, cyano, halo, nitro, halo-substituted $(C_{1-6})$alkyl, —$X^2OR^4$, —$X^2C(O)R^6$, —$X^2OC(O)R^6$, —$X^2C(O)OR^4$, —$X^2SR^4$, —$X^2S(O)R^6$, —X²S(O)₂R⁶, —X²NR⁴R⁴, —X²NR⁴C(O)R⁶, —X²NR⁴C(O)OR⁶, —X²C(O)NR⁴R⁴, —X²NR⁴C(O)NR⁴R⁴, —X²NR⁴C(NR⁴)NR⁴R⁴, —X²C(O)NR⁴X²C(O)OR⁴, —X²NR⁴S(O)₂R⁶ and —X²S(O)₂NR⁴R⁴, wherein X² and R⁴ are as defined above and R⁶ is (C₁₋₆)alkyl or halo-substituted (C₁₋₆)alkyl, and wherein any said heteroalkylene, carbocycloalkyl and heterocycloalkyl rings within A² and R⁸ may be substituted further with 1 to 2 groups independently selected from (C₁₋₆)alkylidene, oxo, imino and thioxo; and the individual stereoisomers and mixtures of stereoisomers; and the pharmaceutically acceptable salts thereof.

37. The compound of claim 36 in which A² is a group selected from Formulae (h), (i), (j), (k), (l) and (m):

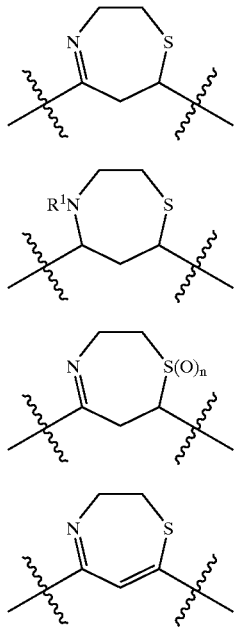

(h)

(k)

(l)

(m)

in which n is 1 or 2 and R¹ is acetyl or trifluoroacetyl; and the individual stereoisomers and mixtures of stereoisomers; and the pharmaceutically acceptable salts thereof.

38. A compound of Formula II:

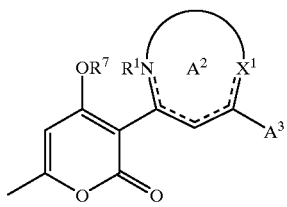

II in which:
  the dashed lines indicate optional unsaturation without violating valency rules;
  R¹ is hydrogen, (C₁₋₆)alkyl or —C(O)R⁶, wherein R⁶ is as defined below, or R¹ is absent when a double bond exists between the nitrogen atom to which R¹ is attached and an adjacent ring atom;
  R⁷ is hydrogen;
  X¹ is —S(O)ₙ—, wherein n is 0, 1, or 2;
  A² is a monocyclic ring selected from heteroarylene or unsaturated, partially unsaturated or saturated heterocycloalkylene containing a total of 7 ring atoms, wherein A² may be substituted with a group selected from —R⁸, —X²OR⁸, —X²C(O)R⁸, —X²OC(O)R⁸, —X²C(O)OR⁸, —X²SR⁸, —X²S(O)R⁸, —X²S(O)₂R⁸, —X²NR⁴R⁸, —X²NR⁴C(O)R⁸, —X²NR⁴C(O)OR⁸, —X²C(O)NR⁴R⁸, —X²NR⁴C(O)NR⁴R⁸, —X²NR⁴C(NR⁴)NR⁴R⁸, —X²NR⁴S(O)₂R⁸ and —X²S(O)₂NR⁴R⁸, wherein X² is a bond or (C₁₋₆)alkylene, R⁸ is —X²R⁹ wherein X² is as defined above and R⁹ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and R⁴ at each occurrence independently is hydrogen, (C₁₋₆)alkyl or halo-substituted (C₁₋₆)alkyl, wherein each ring within A² and R⁸ contains from 3 to 8 ring atoms and may be substituted with 1 to 3 groups independently selected from (C₁₋₆)alkyl, cyano, halo, nitro, halo-substituted (C₁₋₆)alkyl, —X²OR⁴, —X²C(O)R⁶, —X²OC(O)R⁶, —X²C(O)OR⁴, —X²SR⁴, —X²S(O)R⁶, —X²S(O)₂R⁶, —X²NR⁴R⁴, —X²NR⁴C(O)R⁶, —X²C(O)NR⁴R⁴, —X²NR⁴C(O)NR⁴R⁴, —X²NR⁴C(NR⁴)NR⁴R⁴, —X²C(O)NR⁴X²C(O)OR⁴, —X²NR⁴S(O)₂R⁶ and —X²S(O)₂NR⁴R⁴, wherein X² and R⁴ are as defined above and R⁶ is (C₁₋₆)alkyl or halo-substituted (C₁₋₆)alkyl, and wherein any said heteroalkylene, carbocycloalkyl and heterocycloalkyl rings within A² and R⁸ may be substituted further with 1 to 2 groups independently selected from (C₁₋₆)alkylidene, oxo, imino and thioxo; and A³ is a monocyclic or fused polycyclic ring system selected from aryl containing a total of 6 to 14 ring atoms, heteroaryl containing a total of 5 to 14 ring atoms and unsaturated, partially unsaturated or saturated carbocycloalkyl or heterocycloalkyl each containing a total of 3 to 14 ring atoms, wherein A³ may be substituted with a group selected from —²R⁹', —X²OR⁹', —X²C(O)R⁹', —X²OC(O)R⁹', —X²C(O)OR⁹', —X²SR⁹', —X²S(O)R⁹', —X²S(O)₂R⁹', —X²NR⁴R⁹', —X²NR⁴C(O)R⁹', —X²NR⁴C(O)OR⁹', —X²C(O)NR⁴R⁹', —X²NR⁴C(O)NR⁴R⁹', —X²NR⁴C(NR⁴)NR⁴R⁹', —X²NR⁴S(O)₂R⁹ and —X²S(O)₂NR⁴R⁹', wherein X² is a bond or (C₁₋₆)alkylene, R⁹' is —X²R¹⁰ wherein X² is as defined above and R¹⁰ is aryl containing a total of 6 to 10 ring atoms, heteroaryl containing a total of 5 to 10 ring atoms or unsaturated, partially unsaturated or saturated carbocycloalkyl or heterocycloalkyl each containing a total of 3 to 10 ring atoms, and R⁴ at each occurrence independently is hydrogen, (C₁₋₆)alkyl or halo-substituted (C₁₋₆)alkyl, wherein each ring within A³ and R¹⁰ contains from 3 to 8 ring atoms and may be substituted with 1 to 3 groups independently selected from (C₁₋₆)alkyl, cyano, halo, nitro, halo-substituted (C₁₋₆)alkyl, —X²OR⁴, —X²C(O)R⁶, —X²OC(O)R⁶, —X²C(O)OR⁴, —X²SR⁴, —X²S(O)R⁶, —X²S(O)₂R⁶, —X²NR⁴R⁴, —X²NR⁴C(O)R⁶, —X²NR⁴C(O)OR⁴, —X²C(O)NR⁴R⁴, —X²NR⁴C(O)NR⁴R⁴, —X²NR⁴C(NR⁴)NR⁴R⁴, —X²NR⁴S(O)₂R⁶ and —X²S(O)₂NR⁴R⁴, wherein X² and R⁴ are as defined above and R⁶ is (C₁₋₆)alkyl or halo-substituted (C₁₋₆)alkyl, and wherein any said carbocycloalkyl and heterocycloalkyl rings within A³ and R¹⁰ may be substituted further with 1 to 2 groups independently selected from (C₁₋₆)alkylidene, oxo, imino and thioxo with the proviso that only one of A³ and R¹⁰ is a fused polycyclic ring system; and the individual stereoisomers and mixtures of stereoisomers; and the pharmaceutically acceptable salts thereof;

provided, however, Formula II does not represent a compound wherein A² is 2,3,6,7-tetrahydro-[1,4]thiazepinylene and A³ is benzo[1,3]dioxolyl, indolyl, phenyl, pyridyl or thienyl, wherein said phenyl may be substituted with 1 to 3 groups independently selected from halo, nitro, hydroxy, ($C_{1-4}$)alkyl, ($C_{1-4}$)alkylsulfanyl and ($C_{1-4}$)alkyloxy or any individual stereoisomer or mixture of stereoisomers, or pharmaceutically acceptable salt thereof.

39. The compound of claim 38 in which A² is a group selected from Formulae (h), (k), (l) and (m):

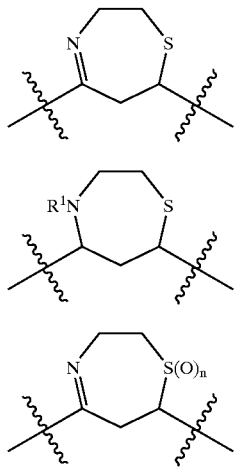

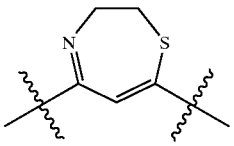

in which n is 1 or 2 and R¹ is acetyl or trifluoroacetyl; and the individual stereoisomers and mixtures of stereoisomers; and the pharmaceutically acceptable salts thereof.

40. The compound of claim 39 in which A³ is phenyl or heteroaryl containing a total of 5 to 9 ring atoms, wherein A³ may be substituted with a group selected from —R⁹', —X²OR⁹', —X²SR⁹' and —X²S(O)₂R⁹', wherein R⁹' is —X²R¹⁰, X² is a bond or ($C_{1-6}$)alkylene and R¹⁰ is phenyl or heteroaryl containing a total 5 to 6 ring atoms, wherein each ring within A³ and R¹⁰ may be substituted with 1 to 3 groups independently selected from ($C_{1-6}$)alkyl, halo, halo-substituted ($C_{1-6}$)alkyl, —X²OR⁴, —X²SR⁴, —X²S(O)₂R⁶ and —X²NR⁴R⁴, wherein R⁴ at each occurrence independently is hydrogen, ($C_{1-6}$)alkyl or halo-substituted ($C_{1-6}$)alkyl and R⁶ is ($C_{1-6}$)alkyl or halo-substituted ($C_{1-6}$)alkyl; and the individual stereoisomers and mixtures of stereoisomers; and the pharmaceutically acceptable salts thereof.

\* \* \* \* \*

UNITED STATES PATENT AND TRADEMARK OFFICE
CERTIFICATE OF CORRECTION

PATENT NO.        : 6,861,419 B2 Page 1 of 1
APPLICATION NO. : 09/836548
DATED             : March 1, 2005
INVENTOR(S)       : Drewe et al.

It is certified that error appears in the above-identified patent and that said Letters Patent is hereby corrected as shown below:

On the title page (73) add the following Assignee --Axys Pharmaceuticals, Inc., South San Francisco, Ca. (US)--

Signed and Sealed this

Twenty-eighth Day of August, 2007

JON W. DUDAS
*Director of the United States Patent and Trademark Office*